US012611415B2

(12) United States Patent
Trevaskis et al.

(10) Patent No.: US 12,611,415 B2
(45) Date of Patent: Apr. 28, 2026

(54) METHODS AND COMPOUNDS FOR TREATMENT OF METABOLIC DISEASE

(71) Applicant: Monash University, Clayton (AU)

(72) Inventors: Natalie Trevaskis, Newington (AU); Christopher John Porter, Clayton (AU); Tim Quach, Southbank (AU); Sifei Han, Bundoora (AU); Enyuan Cao, Clayton (AU); Luojuan Hu, Bundoora (AU); Matthew Watt, Clayton (AU)

(73) Assignee: MONASH UNIVERSITY, Clayton (AU)

( * ) Notice: Subject to any disclaimer, the term of this patent is extended or adjusted under 35 U.S.C. 154(b) by 1035 days.

(21) Appl. No.: 17/753,936

(22) PCT Filed: Sep. 21, 2020

(86) PCT No.: PCT/AU2020/050997

§ 371 (c)(1),
(2) Date: Mar. 18, 2022

(87) PCT Pub. No.: WO2021/051172

PCT Pub. Date: Mar. 25, 2021

(65) Prior Publication Data

US 2022/0339168 A1 Oct. 27, 2022

Related U.S. Application Data

(60) Provisional application No. 62/902,600, filed on Sep. 19, 2019.

(51) Int. Cl.
*A61K 31/635* (2006.01)
*A61K 31/404* (2006.01)
*A61P 3/04* (2006.01)

(52) U.S. Cl.
CPC .......... *A61K 31/635* (2013.01); *A61K 31/404* (2013.01); *A61P 3/04* (2018.01)

(58) Field of Classification Search
CPC ........ A61K 31/635; A61K 31/404; A61P 3/04
See application file for complete search history.

(56) References Cited

U.S. PATENT DOCUMENTS

| | | | | |
|---|---|---|---|---|
| 11,738,087 B2 * | 8/2023 | Porter | .................. | C07D 489/12 514/171 |
| 11,883,497 B2 * | 1/2024 | Bonner | ................ | C07D 209/08 |
| 2004/0204472 A1 | 10/2004 | Briggs et al. | | |
| 2004/0248965 A1 | 12/2004 | Chirchin et al. | | |
| 2013/0030007 A1 | 1/2013 | Penninger et al. | | |
| 2018/0243425 A1 | 8/2018 | Porter et al. | | |
| 2019/0105299 A1 | 4/2019 | Porter et al. | | |

FOREIGN PATENT DOCUMENTS

CN 105287552 A 2/2016

OTHER PUBLICATIONS

International Search Report and Written Opinion for corresponding PCT/AU2020/050997, mailed Dec. 1, 2020, 14 pages.
Hsieh, P.-S., et al., "Selective COX2 inhibition improves whole body and muscular insulin resistance in fructose-fed rats", European Journal of Clinical Investigation, vol. 38(11), pp. 812-819 (2008).
Hu, L., et al., "Glyceride-Mimetic Prodrugs Incorporating Self-Immolative Spacers Promote Lymphatic Transport, Avoid First-Pass Metabolism, and Enhance Oral Bioavailability", Angewandte Chemie International Edition, vol. 55, pp. 13700-13705 (2016).
Belin De Chantemele, E.J., et al., "Cyclooxygenase-2 preserves flow-mediated remodelling in old obese Zucker rat mesenteric arteries", Cardiovascular Research, vol. 86, pp. 516-525 (2010).
International Preliminary Report of Patentability for corresponding PCT/AU2020/050997, mailed Mar. 15, 2022, 7 pages.

* cited by examiner

*Primary Examiner* — Kevin E Weddington
(74) *Attorney, Agent, or Firm* — WOMBLE BOND DICKINSON (US) LLP; Danielle L. Herritt; Mark R. DeLuca

(57) ABSTRACT

The present invention provides methods of treating metabolic diseases including obesity, insulin resistance and type 2 diabetes with inhibitors of COX-2 or VEGFR and lipid prodrugs of COX-2 inhibitors, in particular celecoxib lipid prodrugs, that promote transport of the pharmaceutical agent to the lymphatic system and which enhance release of the parent agent.

10 Claims, 26 Drawing Sheets a b c d e f g h i f g a b

METHODS AND COMPOUNDS FOR TREATMENT OF METABOLIC DISEASE

CROSS-REFERENCE TO RELATED APPLICATIONS

This application is a 371 National Phase Application of International Application No. PCT/AU2020/050997, filed Sep. 21, 2020, which claims the benefit of U.S. Provisional Patent Application No. 62/902,600, filed Sep. 19, 2019; the entire contents of each of which is hereby incorporated by reference.

TECHNICAL FIELD OF THE INVENTION

The present invention relates to methods of treating metabolic diseases, such as obesity, insulin resistance, and type 2 diabetes. The invention also provides compounds and pharmaceutically acceptable compositions useful in the disclosed methods.

BACKGROUND

Obesity is a major health burden worldwide and increases the risk of developing metabolic diseases including type 2 diabetes (T2D), complications of which include pathologies in the macrovasculature (e.g. atherosclerosis), microvasculature (retinopathy and nephropathy), and the central nervous system. The progression of metabolic disease such as T2D is also commonly underpinned by the development of insulin resistance (IR).

Current treatments directed at IR and T2D, however, including lifestyle modification, surgical intervention and drug treatment, have failed to control the epidemic of obesity and metabolic disease. Lifestyle modifications, such as diet and physical exercise, suffer from difficulties in long-term patient compliance. Bariatric surgery is resource-intensive and limited to patients who are healthy enough to undergo surgery. Existing drug treatments (e.g. metformin, thiazolidinediones, incretin mimetics, and dipeptidyl peptidase-4 inhibitors) can have undesired side effects and do not always adequately control blood glucose levels.

Excess adipose tissue around the abdomen (visceral adipose tissue or VAT) increases the risk of IR. In contrast, subcutaneous adipose tissue (SAT) is less well correlated with the onset of IR (and in some instances appears protective against IR and metabolic disease). VAT expansion is also known to lead to pathogenic inflammatory and metabolic changes that promote IR. The underlying mechanisms that drive these inflammatory changes, however, are poorly understood. changes that promote IR. The underlying mechanisms that drive these inflammatory changes, however, are poorly understood.

Lymphatic vessels and nodes throughout the body are surrounded by adipose tissue and the VAT surrounds the lymphatics that drain the internal organs. This includes the intestinal lymphatic vessels that transport fluid, lipids, immune cells and other factors from the intestine and mesentery through the VAT. In transgenic mouse models resulting in lymphatic defects, adipose tissue accumulates around the sites of lymphatic dysfunction.

Accordingly, there is a need to enhance fundamental understanding of the pathogenic drivers of obesity, IR, T2D, and related metabolic diseases, particularly regarding the potential role of lymphatic defects, and to design novel and more effective treatments for these pathologies.

SUMMARY OF THE INVENTION

In one aspect, the present invention provides a method of treating a metabolic disease, disorder or condition (such as one of those disclosed herein, e.g., obesity, insulin resistance, or type 2 diabetes) in a patient in need thereof, comprising reducing an aspect of obesity-associated mesenteric lymphatic dysfunction in the patient.

In another aspect, the present invention provides a method of treating a metabolic disease, disorder or condition in a patient in need thereof, comprising reducing dysfunctional lymphangiogenesis in the patient.

In another aspect, the present invention provides a method of treating a metabolic disease, disorder or condition in a patient in need thereof, comprising administering to the patient an effective amount of a lipid prodrug of Formula I:

I

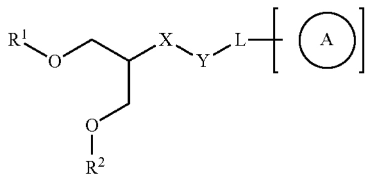

or a pharmaceutically acceptable salt thereof, wherein each variable is as defined herein. In some embodiments, the lipid prodrug is Compound I-1:

I-1

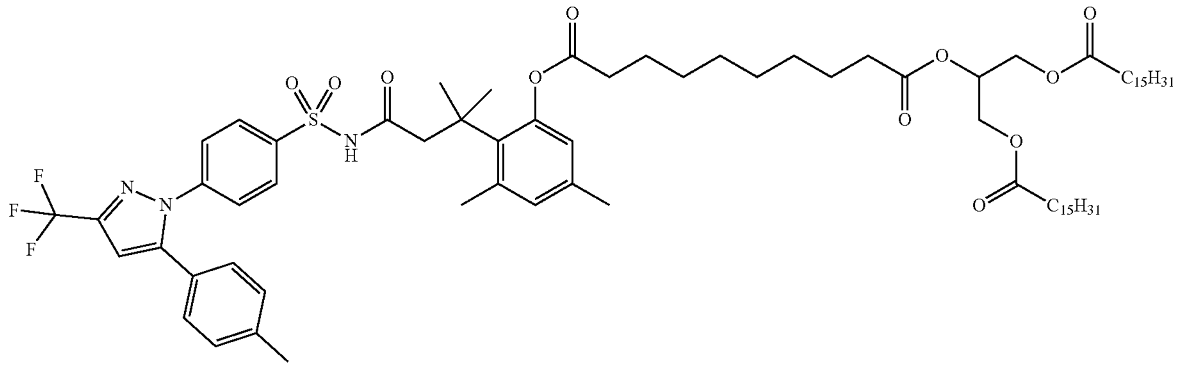

or a pharmaceutically acceptable salt thereof.

DETAILED DESCRIPTION OF THE INVENTION

Figure 1:
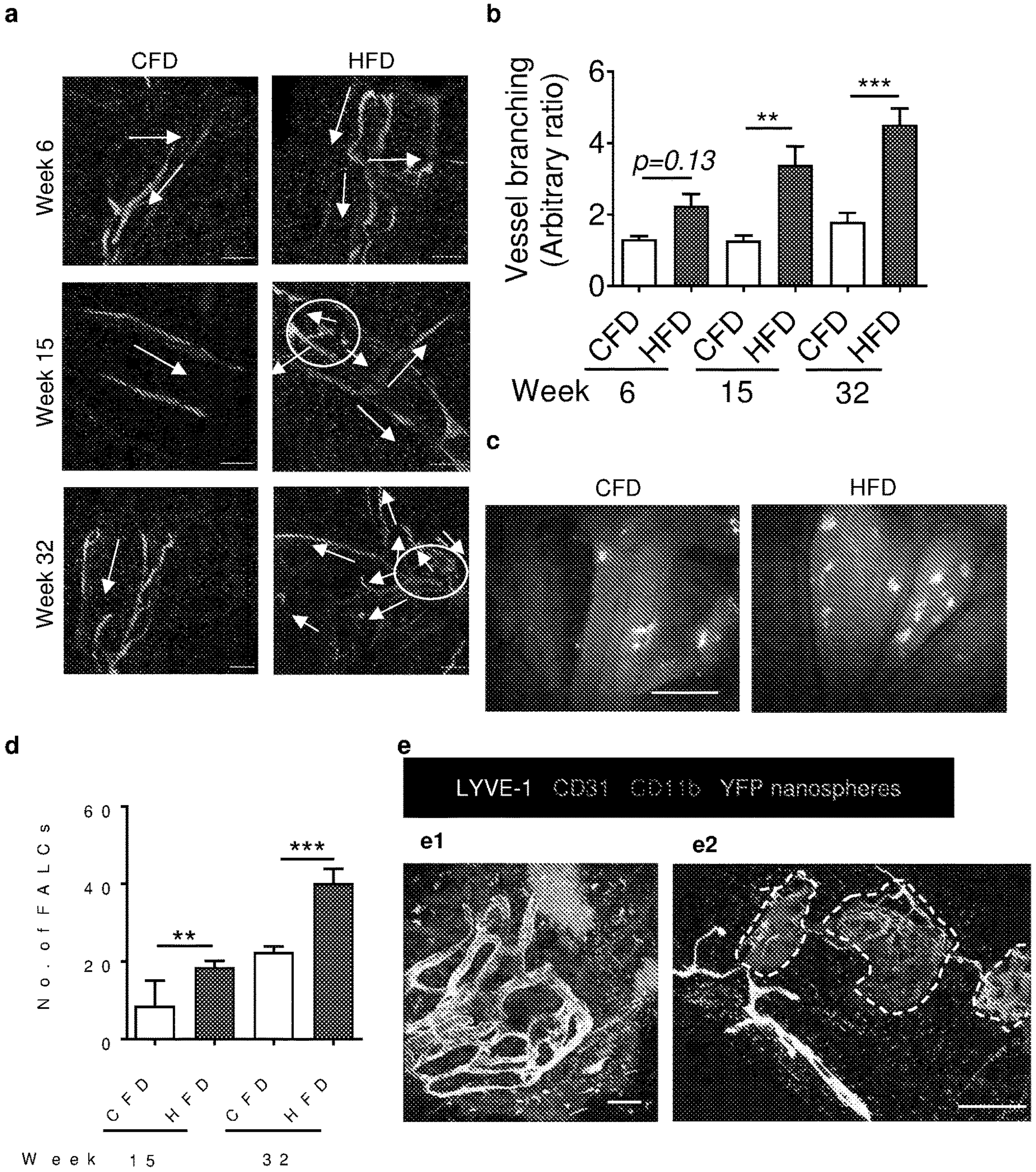
FIG. 1 shows progressive remodelling of the mesenteric lymphatics in C57BL/6 mice fed a high fat diet (HFD). (a) Representative whole mount immunofluorescence images of the mesenteric afferent lymph vessels (LYVE-1 (green)) and cell nuclei (Hoechst (blue)) in VAT of mice fed HFD or CFD for 6, 15 or 32 weeks. Scale bars, 500 μm. (b) Quantification of mesenteric lymph vessel branching in VAT after 6, 15 or 32 weeks of CFD or HFD feeding. Data for a-b are n=2 or n=3 for week 6, n=6 or n=7 for week 15 and n=4 or n=5 for week 32. b shows mean+s.e.m except for CFD at week 6 which is mean+range. (c) Fluorescent images showing fat-associated lymphoid clusters (FALCs) in VAT as identified by uptake of IP administered YFP fluorescent nanospheres (seen as white dots). (d) Total number of FALCs in VAT of mice fed HFD or CFD for 15 or 32 weeks. Mean+s.e.m for n=5 or 6 mice for week 15 and n=9 or 10 mice for week 32. (e) Representative whole mount immunofluorescence images of FALCs showing LYVE-1+ lymph vessels (yellow), CD31+ blood vessels (pink), CD11b+ myeloid cells (blue) and YFP fluorescent nanospheres (green). (e1) Lymphatic vessels (yellow) and blood vessels (pink) in a single FALC. (e2) Three separate FALCs (circled by white dots) that are connected by an extensive lymphatic network (yellow vessels). Scale bars, 100 μm (e1) and 500 μm (e2). Statistical differences, $p<0.01$ and $*p<0.005$ from Student's t-test.

Various aspects of the invention are set forth below in sections; however, aspects of the invention described in one particular section are not to be limited to any particular section.

General Description of Certain Aspects of the Invention

As described herein, it has now been found that obesity leads to mesenteric lymphatic dysfunction, which in turn stimulates the accumulation of VAT, inflammatory and metabolic changes that promote insulin resistance and metabolic disease. The composition, structure and function of key components of the mesenteric lymphatic system was found to undergo profound and progressive remodelling in C57BL/6 mice fed a high fat diet (HFD) for 6, 15, 23 or 33 weeks. High-fat-diet-modified lymph was found to contain elevated levels of pro-inflammatory cells and pro-lymphangiogenic factors (e.g. VEGFc), which was found to stimulate dysfunctional lymphangiogenesis, leading to the formation of highly branched mesenteric lymphatic vessels in VAT that ‘leak’ HFD-modified lymph into VAT. Lymph leakage to VAT subsequently triggers metabolic and inflammatory changes that promote insulin resistance. Mesenteric lymphatic branching and lymph leakage were found to be mediated by the COX2 and VEGFc/d-VEGFR3 pathways, suggesting a novel mechanism for the effects of COX-2 inhibitors on metabolic disease. Furthermore, a lymph-targeted inhibitor of COX-2 (Compound I-1) was found to reverse, more effectively than a corresponding non-lymph-targeted COX-2 inhibitor, the mesenteric lymphatic dysfunction, visceral obesity, inflammation, glucose intolerance, and insulin resistance associated with obesity.

Accordingly, in one aspect, the present invention provides a method of treating a metabolic disease, disorder or condition in a patient in need thereof, comprising reducing an aspect of obesity-associated mesenteric lymphatic dysfunction in the patient. In another aspect, the present invention provides a method of treating a metabolic disease, disorder or condition in a patient in need thereof, comprising administering to the patient an effective amount of a pharmaceutical agent or lipid prodrug thereof that reduces an aspect of obesity-associated mesenteric lymphatic dysfunction in the patient. In some embodiments, the aspect of obesity-associated mesenteric lymphatic dysfunction is dysfunctional lymphangiogenesis. In some embodiments, the aspect of obesity-associated mesenteric lymphatic dysfunction is leakage of lymph. In some embodiments, the aspect of obesity-associated mesenteric lymphatic dysfunction is leakage of lymph into nearby tissue. In some embodiments, the aspect of obesity-associated mesenteric lymphatic dysfunction is leakage of lymph into proximal VAT. In some embodiments, the aspect of obesity-associated mesenteric lymphatic dysfunction is elevated levels of pro-inflammatory mediators in the lymph. In some embodiments, the aspect of obesity-associated mesenteric lymphatic dysfunction is elevated levels of pro-inflammatory cells in the lymph. In some embodiments, the aspect of obesity-associated mesenteric lymphatic dysfunction is elevated levels of pro-lymphangiogenic factors in the lymph. In some embodiments, the aspect of obesity-associated mesenteric lymphatic dysfunction is elevated levels of VEGFc in the lymph. In some embodiments, the aspect of obesity-associated mesenteric lymphatic dysfunction is elevated levels of sphingolipids, ceramides, sterols, and/or phospholipids. In some embodiments, the aspect of obesity-associated mesenteric lymphatic dysfunction is elevated levels of ceramides and/or sphingomyelins.

In another aspect, the present invention provides a method of treating a metabolic disease, disorder or condition in a patient in need thereof, comprising reducing dysfunctional lymphangiogenesis in the patient. In some embodiments, the dysfunctional lymphangiogenesis comprises excessive lymphatic branching. In some embodiments, the dysfunctional lymphangiogenesis comprises growth of lymph vessels in random directions (i.e. rather than in the direction of lymph flow). In some embodiments, the dysfunctional lymphangiogenesis comprises leakage of lymph. In some embodiments, the dysfunctional lymphangiogenesis comprises leakage of lymph into nearby tissue. In some embodiments, the dysfunctional lymphangiogenesis comprises leakage of lymph into proximal VAT.

In some embodiments, the methods of the present invention comprise administering to the patient an inhibitor of the COX2 and/or VEGFc/d-VEGFR3 pathways. In some embodiments, the method comprises administering to the patient a VEGFR3 kinase inhibitor. In some embodiments, the VEGFR3 kinase inhibitor is MAZ51. MAZ51 is described in, for example, WO2003/007943, which is hereby incorporated by reference in its entirety. The synthesis of the VEGFR3 inhibitor MAZ51 is described in Kirkin et al., *Eur J Biochem* 268: 5530-5540, the contents of which is herein incorporated by reference in its entirety. The compound has been shown to potently inhibit both VEGF-C-dependent and VEGF-C-independent VEGF receptor (VEGFR)-3 phosphorylation in endothelial cell lines (Park et al., *PLoS One.* 2014; 9(9): e109055, and references therein), including cultured lymphatic endothelial cell lines (Breslin et al., *Lymphat Res Biol.* 2007; 5(2): 105-113).

In some embodiments, the method comprises administering to the patient a COX-2 inhibitor. In some embodiments, the COX-2 inhibitor is celecoxib. In some embodiments, the COX-2 inhibitor is Compound I-1:

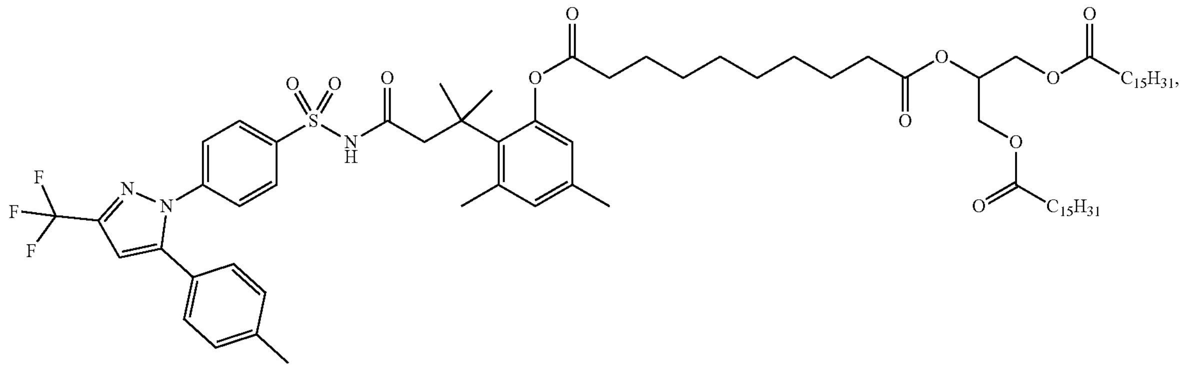

or a pharmaceutically acceptable salt thereof. Compound I-1 is described in, for example, WO2016/023082, which is hereby incorporated by reference in its entirety. In some embodiments, the COX-2 inhibitor is a lipid prodrug described herein. In some embodiments, the inhibitor is delivered selectively to the lymphatic system of the patient. In some embodiments, the inhibitor is administered orally.

In another aspect, the present invention provides a method of treating a metabolic disease, disorder or condition in a patient in need thereof, comprising administering to the patient an effective amount of Compound I-1, or a pharmaceutically acceptable salt thereof. In another aspect, the present invention provides a method of preventing a metabolic disease, disorder or condition in a patient in need thereof, comprising administering to the patient an effective amount of Compound I-1, or a pharmaceutically acceptable salt thereof. In some embodiments, an aspect of obesity-associated mesenteric lymphatic dysfunction is reduced in the patient after receiving treatment. In some embodiments, dysfunctional lymphangiogenesis is reduced in the patient after receiving treatment.

In another aspect, the present invention provides a method of treating a metabolic disease, disorder, or condition in a patient in need thereof, comprising administering to the patient an effective amount of a lipid prodrug described herein.

In another aspect, the present invention provides a method of preventing a metabolic disease, disorder, or condition in a patient in need thereof, comprising administering to the patient an effective amount of a lipid prodrug described herein.

In another aspect, the present invention provides a method of treating a metabolic disease, disorder, or condition in a patient in need thereof, comprising administering to the patient an effective amount of a lipid prodrug of Formula I:

I

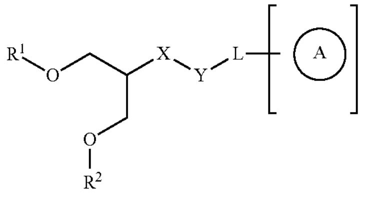

or a pharmaceutically acceptable salt thereof, wherein:

$R^1$ and $R^2$ are each independently hydrogen, an acid-labile group, a lipid, or —C(O)$R^3$;

each $R^3$ is independently a saturated or unsaturated, straight or branched, optionally substituted $C_{1-37}$ hydrocarbon chain;

X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

Y is absent or is —C(O)—, —C(NR)—, or —C(S)—;

L is a covalent bond or a bivalent, saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

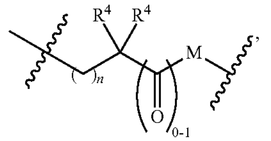

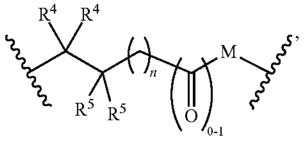

or

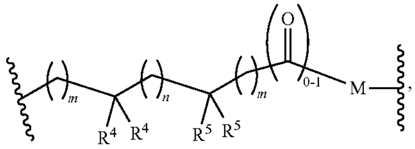

wherein either the right-hand side or left-hand side of L is attached to A;

each -Cy- is independently an optionally substituted 3-6 membered bivalent saturated, partially unsaturated, or aromatic ring having 0-4 heteroatoms independently selected from nitrogen, oxygen, or sulfur;

each $R^4$ and $R^5$ is independently hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;

-M- is a self-immolative group;

n is 0-18;

each m is independently 0-6; and

A is a COX-2 inhibitor.

In another aspect, the present invention provides a method of preventing a metabolic disease, disorder, or condition in a patient in need thereof, comprising administering to the patient an effective amount of a lipid prodrug of Formula I, or a pharmaceutically acceptable salt thereof.

In some embodiments, $R^1$ and $R^2$ are —C(O)$R^3$. In some embodiments, each $R^3$ is independently a saturated or unsaturated, unbranched $C_{2-37}$ hydrocarbon chain. In some embodiments, X is —O—. In some embodiments, Y is —C(O)—. In some embodiments, the lipid prodrug is of Formula IX-c:

IX-c

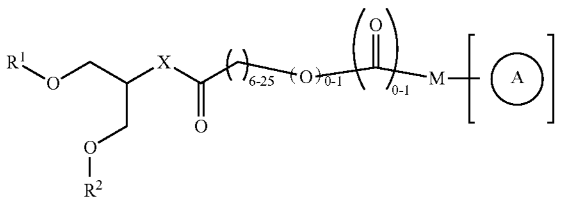

or a pharmaceutically acceptable salt thereof.

In some embodiments, A is

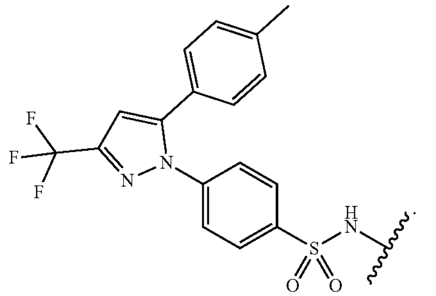 [SMILES: *NS(=O)(=O)c1ccc(-n2nc(C(F)(F)F)cc2-c2ccc(C)cc2)cc1]

In some embodiments, the lipid prodrug is Compound I-1:

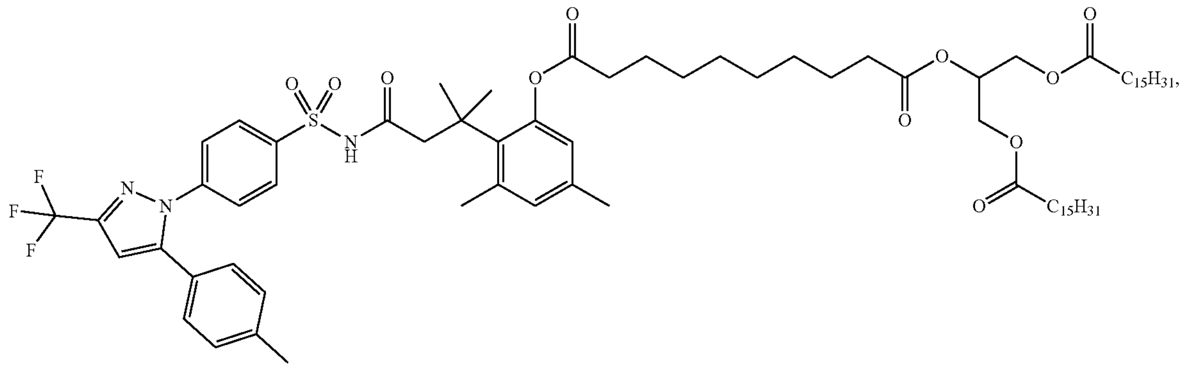

or a pharmaceutically acceptable salt thereof.

In some embodiments, the lipid prodrug is delivered selectively to the lymphatic system of the patient. In some embodiments, the lipid prodrug is administered orally. In some embodiments, the lipid prodrug is selectively taken up into the lymphatic system after oral administration.

In some embodiments, the method further comprises a reduction in mesenteric lymphatic dysfunction, visceral obesity, inflammation, glucose intolerance, and/or insulin resistance associated with obesity. In some embodiments, the method further comprises reducing an aspect of obesity-associated mesenteric lymphatic dysfunction in the patient. In some embodiments, the aspect of obesity-associated mesenteric lymphatic dysfunction is dysfunctional lymphangiogenesis, leakage of lymph into proximal visceral adipose tissue (VAT), elevated levels of pro-inflammatory cells in the lymph, elevated levels of pro-lymphangiogenic factors in the lymph, and/or elevated levels of VEGFc in the lymph.

In some embodiments, the metabolic disease, disorder, or condition is obesity, glucose intolerance, insulin resistance, hyperinsulinemia, type 2 diabetes, or non-alcoholic fatty liver disease. In some embodiments, the metabolic disease, disorder, or condition is obesity, glucose intolerance, insulin resistance, hyperinsulinemia, or type 2 diabetes. In some embodiments, the metabolic disease, disorder, or condition is obesity, insulin resistance, or type 2 diabetes. In some embodiments, the metabolic disease, disorder, or condition is obesity. In some embodiments, the metabolic disease, disorder, or condition is visceral obesity. In some embodiments, the metabolic disease, disorder, or condition is glucose intolerance. In some embodiments, the metabolic disease, disorder, or condition is insulin resistance. In some embodiments, the metabolic disease, disorder, or condition is hyperinsulinemia. In some embodiments, the metabolic disease, disorder, or condition is type 2 diabetes. In some embodiments, the metabolic disease, disorder, or condition is non-alcoholic fatty liver disease. In some embodiments, the metabolic disease, disorder, or condition is non-alcoholic steatohepatitis.

The methods of the present invention can be characterized by therapeutic improvements experienced by the patient after receiving treatment. In some embodiments, the patient gains weight more slowly after receiving treatment. In some embodiments, the patient loses weight after receiving treatment. In some embodiments, the patient has decreased adiposity after receiving treatment. In some embodiments, the patient has decreased VAT after receiving treatment. In some embodiments, the patient has decreased SAT after receiving treatment.

In some embodiments, the patient has decreased fasting blood glucose levels after receiving treatment. In some embodiments, the patient has improved oral glucose tolerance after receiving treatment. In some embodiments, the patient has improved insulin sensitivity after receiving treatment. In some embodiments, the patient has decreased fasting hyperinsulinemia after receiving treatment. In some embodiments, the patient has decreased hyperinsulinemia after glucose challenge after receiving treatment.

In some embodiments, the patient has decreased levels of sphingolipids, ceramides, sterols, and/or phospholipids after receiving treatment. In some embodiments, the patient has decreased levels of ceramides and/or sphingomyelins after receiving treatment. In some embodiments, the patient has decreased systemic inflammation after receiving treatment.

In some embodiments, the patient is a human. In some embodiments, the patient is a mammal.

Definitions

While the terms used herein are believed to be well understood by one of ordinary skill in the art, definitions are set forth herein to facilitate explanation of the presently-disclosed subject matter.

As used herein, the term "about," when referring to a numerical value or range of a parameter such as mass, weight, volume, time, concentration, biological activity, clogP, or percentage, is meant to encompass variations of, e.g., ±20%, in some embodiments ±10%, in some embodiments ±5%, in some embodiments ±1%, in some embodiments ±0.5%, and in some embodiments ±0.1% from the specified value or range.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "inhibitor" is meant to refer to an agent or compound that decreases, reduces, lessens, or blocks an activity or phenomenon, e.g., completely or partially. As used herein, the term "inhibition" and its derivatives (e.g., inhibiting, inhibited, etc.) is meant to refer to a decrease, reduction, lessening, or blocking of an activity or phenomenon, e.g., completely or partially. The inhibition is meant to encompass various degrees of decreasing, reducing, lessening, or blocking, and thus the terms "inhibitor" and "inhibition" do not imply any particular degree or amount of inhibition. For example, the "inhibitor" may decrease, reduce, lessen, or block the activity of an enzyme, hormone, receptor or other bioactive molecule and the "inhibition" may refer to a decrease, reduction, lessening, or blocking of the activity of an enzyme, hormone, receptor or other bioactive molecule.

The term "lipid," as used herein, refers to natural and non-natural hydrophobic and/or lipophilic fats, oils, polymers, hydrocarbons, and other such materials. In some embodiments, suitable lipids, when incorporated into a lipid prodrug, are processed or metabolized similarly to triglycerides in the GI tract or mimic such processing or metabolism. The term "glyceride" refers to an ester of glycerol (1,2,3-propanetriol) with acyl radicals of fatty acids or other lipids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being the ends of the glycerol.

Naturally occurring oils and fats consist largely of triglycerides wherein the 3 fatty acyl residues may or may not be identical. The term "long chain triglycerides" (or "LCT") means both a simple and mixed triglyceride containing fatty acids with more than 12 carbon atoms (long chain fatty acids, "LCFA"), whereas the term "medium chain triglycerides" (or "MCT") means both a simple and mixed triglyceride containing fatty acids with 4 to 12 carbon atoms.

The term "ECN" or "equivalent carbon number" means the sum of the number of carbon atoms in the acyl chains of a glyceride molecule. For example, tripalmitin (tripalmitic glycerol), which is a simple triglyceride containing 3 acyl radicals of 16 carbon atoms, has an ECN of 3×16=48. Conversely, a triglyceride with an ECN=40 may have "mixed" acyl chain lengths of 8, 16 and 16; 10, 14 and 16; 8, 14 and 18, etc. Naturally occurring oils are frequently "mixed" with respect to specific fatty acids, but tend not to contain LCFAs and MCFAs on the same glycerol backbone. Thus, triacylglycerols with ECNs of 24-30 typically contain predominately medium chain fatty acids, while triacylglycerols with ECNs of greater than 43 typically contain predominantly long chain fatty acids. Triacylglycerols having an ECNs of 32-42 typically contain one or two MCFA in combination with one or two LCFAs to "fill" the triglyceride. Triacylglycerols with ECNs in the range of greater than 30 to less than 48 typically represent mixed triacylglycerol species that are absent from or are present in significantly lower concentrations in physical mixtures. The fatty acids that occur in foods usually contain an even number of carbon atoms in an unbranched chain, e.g., lauric or dodecanoic acid.

The term "self-immolative group," as used herein, refers to a bivalent chemical moiety that comprises a covalent, scissile bond as one of its bivalent bonds and a stable, covalent bond with a therapeutic agent as its other bivalent bond, wherein the bond with the therapeutic agent becomes labile upon cleavage of the scissile bond. Examples of self-immolative groups include, but are not limited to, disulfide groups, hydrazones, acetal self-immolative groups, carboxyacetal self-immolative groups, carboxy(methylacetal) self-immolative groups, p-hydroxybenzyl self-immolative groups, para-hydroxybenzyl carbonyl self-immolative groups, flipped ester self-immolative groups, and trimethyl lock, or 2-hydroxyphenyl carbamate (2-HPC) self-immolative groups. A number of other suitable self-immolative groups are known in the art as described, for example, in C. A. Blencowe et al., Polym. Chem. 2011, 2, 773-790 and F. Kratz et al., Chem Med Chem. 2008, 3(1), 20-53; Huvelle, S. et al., *Org. Biomol. Chem.* 2017, 15(16), 3435-3443; and Alouane, A. et al., *Angewandte Chemie International Edition* 2015, 54 (26), 7492-7509; and Levine, M. N. et al., *Chem. Sci. VL-IS*-3 (8), 2412-2420; each of which is hereby incorporated by reference in its entirety.

As used herein, the term “therapeutic agent,” “active pharmaceutical agent,” “active agent,” or “pharmaceutical agent” includes any therapeutic agent or imaging (contrasting) agent which would benefit from transport via the intestinal lymphatic system, for example, to enable oral administration (e.g. of an intravenously administered therapeutic agent), to avoid first pass metabolism, avoid liver toxicity or other toxicity, or for targeted delivery within the lymphatic system. In some embodiments, the therapeutic agent is a small molecule. In some embodiments, the small molecule has a molecular weight of less than 800; or less than 700, 600, 500, 400, or 300. In some embodiments, the molecular weight is about 300 to about 800; or about 400-700, 300-600, or 400-500.

Lipid prodrug compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, Handbook of Chemistry and Physics, $98^{th}$ Ed. Additionally, general principles of organic chemistry are described in “Organic Chemistry,” Thomas Sorrell, University Science Books, Sausalito: 1999, and *March’s Advanced Organic Chemistry: Reactions, Mechanisms, and Structure*, M. B. Smith and J. March, $7^{th}$ Edition, John Wiley & Sons, 2013, the entire contents of which are hereby incorporated by reference.

The term “aliphatic” or “aliphatic group,” as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as “carbocycle,” “cycloaliphatic” or “cycloalkyl”), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, “cycloaliphatic” (or “carbocycle” or “cycloalkyl”) refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term “bicyclic ring” or “bicyclic ring system” refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term “heterobicyclic” is a subset of “bicyclic” that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphonates and phosphates), boron, etc. In some embodiments, a bicyclic group has 7-12 ring members and 0-4 heteroatoms independently selected from nitrogen, oxygen, or sulfur. As used herein, the term “bridged bicyclic” refers to any bicyclic ring system, i.e. carbocyclic or heterocyclic, saturated or partially unsaturated, having at least one bridge. As defined by IUPAC, a “bridge” is an unbranched chain of atoms or an atom or a valence bond connecting two bridgeheads, where a “bridgehead” is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

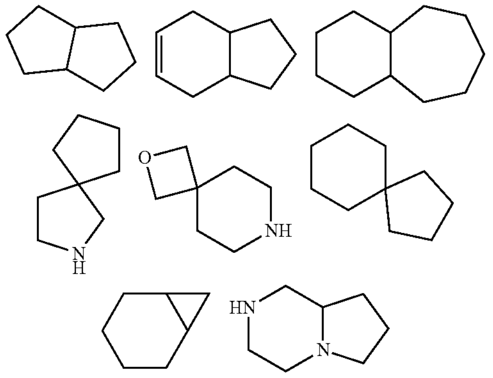

Exemplary bridged bicyclics include:

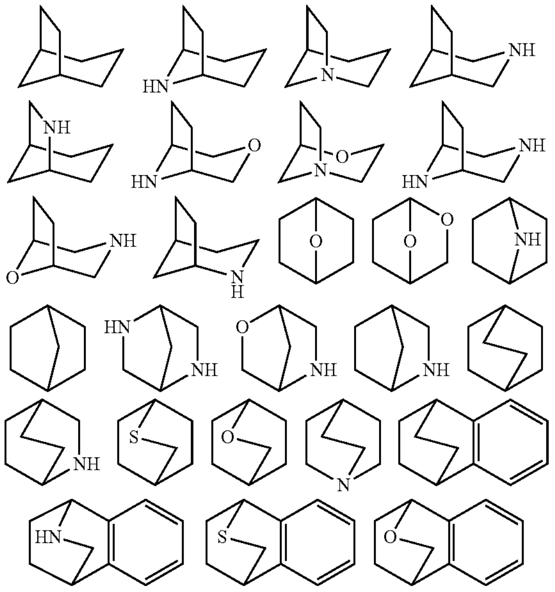

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of boron, oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain" refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR$—, $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$, —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$S(O)(NR^{\circ})R^{\circ}$; —$S(O)_2N$═$C(NR^{\circ}_2)_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —($C_{1-4}$ straight or branched alkylene)O—$N(R^{\circ})_2$; or —($C_{1-4}$ straight or branched)alkylene)C(O)O—$N(R^{\circ})_2$.

Each $R^{\circ}$ is independently hydrogen, $C_{1-6}$ aliphatic, —$CH_2Ph$, —$O(CH_2)_{0-1}Ph$, —$CH_2$— (5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^{\circ}$ selected from ═O and ═S; or each $R^{\circ}$ is optionally substituted with a monovalent substituent independently selected from halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)$C(O)OR^{\bullet}$, or —$SSR^{\bullet}$.

Each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens; or wherein an optional substituent on a saturated carbon is a divalent substituent independently selected from ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, or a divalent substituent bound to vicinal substitutable carbons of an "optionally substituted" group is —$O(CR^*_2)_{2-3}O$—, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

An optional substituent on a substitutable nitrogen is independently —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^{\dagger}$ is $C_{1-6}$ aliphatic, $R^{\dagger}$ is optionally substituted with halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of an amino group (or other basic group) formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid, or by using other methods used in the art such as ion exchange. Other pharmaceutically acceptable salts include adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Abbreviations $^{14}C$-2DG $^{14}C$-2-deoxy-glucose
2DG 2-deoxy-glucose
IBMX 3-isobutyl-1-methylxantine
ACN Acetonitrile
Ap2 Adipocyte protein 2, as known as fatty acid binding protein 4 (FABP4)
ATGL Adipose triglyceride lipase
CCR2 CC chemokine receptor 2
C/EBP CCAAT enhancer binding proteins
CP Celecoxib prodrug
CL Chain length
CCL Chemokine (C—C motif) ligand
CXCL Chemokine (C—X—C motif) ligand
Ch Cholesterol
CFD Chow fat diet
CM Chylomicron
COX-2 Cyclooxygenase 2
DCs Dendritic cells
DMEM Dulbecco's Modified Eagle Medium
FALC Fat-associated lymphoid cluster
FBS Fetal bovine serum
FGF2 Fibroblast growth factor 2
FMO Fluorescence minus one
FFA Free fatty acid
Glut4 Glucose transporter type 4
G3P Glycerol-3-phsophate
PC Glycerophosphocholine
PE Glycerophosphoethanolamine
PL Phospholipid
GAL Gut associated lymphatics
HCA Hierarchal Clustering Analysis
HEV High endothelial venule
HFD High fat diet
HSL Hormone-sensitive lipase
ELISA Immunosorbent assay
iNOS Inducible nitric oxide synthase
IBD Inflammatory bowel disease
IRS Insulin receptor substrate
IR Insulin resistance
IFNγ Interferon gamma
IL Interleukins
LEC Lymphatic endothelial cell
LYVE-1 Lymphatic vessel endothelial hyaluronan receptor 1
LTβR Lymphotoxin β receptor
LysoPC Lysoglycerophosphocholine
MHC Major histocompatibility complex
MAT Mesenteric adipose tissue
MCP-1 Monocyte chemoattractant protein 1
NK cells Natural killer cells
NRP Neuropilin
NO Nitric oxide
NF-κB Nuclear factor-kappa beta
OGTT Oral glucose tolerance test
PPARγ Peroxisome proliferator-activated receptor gamma
PMA Phorbol 12-myristate 13-acetate
PDE3 Phosphodiesterase 3
PL Phospholipid
PCR Polymerase chain reaction
PCA Principal Component Analysis
PGE2 Prostaglandin E 2
ROS Reactive oxygen species
RPMI 1640 Roswell Park Memorial Institute 1640
SEMA Semaphorin
S1P Sphingosine 1 phosphate
SAT Subcutaneous adipose tissue
Th cells T helper cells
TLO Tertiary lymphoid organ
TG Triglyceride
TNF Tumor necrosis factor
T2D Type 2 diabetes
VEGFc Vascular endothelial growth factor c
VEGFR3 Vascular endothelial growth factor receptor 3
VAT Visceral adipose tissue HFD-Induced Obesity is Associated with Progressive Remodelling of the Mesenteric Lymphatics It has now been found that HFD-induced obesity is associated with progressive remodelling of the mesenteric lymphatics. As further described herein, this remodelling leads to metabolic and inflammatory changes that promote insulin resistance. Accordingly, in one aspect, the present invention provides a method of treating a metabolic disease, disorder or condition in a patient in need thereof, comprising reducing an aspect of obesity-associated mesenteric lymphatic dysfunction in the patient. In another aspect, the present invention provides a method of treating a metabolic disease, disorder or condition in a patient in need thereof, comprising reducing dysfunctional lymphangiogenesis in the patient.

To determine how the key components of the intestinal and mesenteric lymphatic network are altered during the progression of HFD-induced obesity, the structure of the lacteals in the intestine, and the initial lymphatics, mesenteric lymphatic vessels in VAT, and fat-associated lymphoid clusters (FALCs) were evaluated in the VAT of male C57BL/6 mice fed a HFD or a control fat diet (CFD) for 6, 15, 23 or 32 weeks.

Both the intestinal villi and lacteals were significantly wider, and the villi, but not lacteals, were shorter after 15 weeks of HFD feeding (FIG. 10*a-e*). The lacteals therefore reached closer to the tip of the villi in the HFD fed animals. In VAT, the number of LYVE-1+ cells (lymphatic endothelial cells (LECs) and/or macrophages) and the size of adipocytes was significantly increased (FIG. 10*f-h*). Additionally, there was a positive correlation between adipocyte size and the increased density of LYVE-1+ cells in VAT.

Moreover, the mesenteric lymphatic vessels in VAT became progressively more branched with HFD feeding. The increase in vessel branches was not statistically significant at week 6, but became apparent at week 15, and was most pronounced after 32 weeks of HFD feeding (FIG. 1*a-b*). The new lymphatic vessel branches were disorganised (i.e. they grew in random directions rather than the direction of lymph flow) and many branches appeared blunt ended (FIG. 1*a*).

VAT associated lymphoid tissue (i.e. FALC) has not previously been evaluated in obesity. The FALC was identified via intraperitoneal injection of fluorescent nanospheres that concentrated in the FALC (FIG. 1*c*) and it was determined that the number of FALCs increased significantly after 15 and 32 weeks of HFD feeding (FIG. 1*d*). The FALCs were mainly concentrated in mesenteric and omental adipose tissue depots, relative to other fat depots in the peritoneal cavity. Notably, chronic HFD feeding also increased immune cell activity within FALCs. Thus, there were increased numbers of antigen presenting cells (CD11+ MHCII+), macrophages (F4/80+) and activated T cells (CD3+CD25+) in the FALC with HFD feeding.

Figure 2:
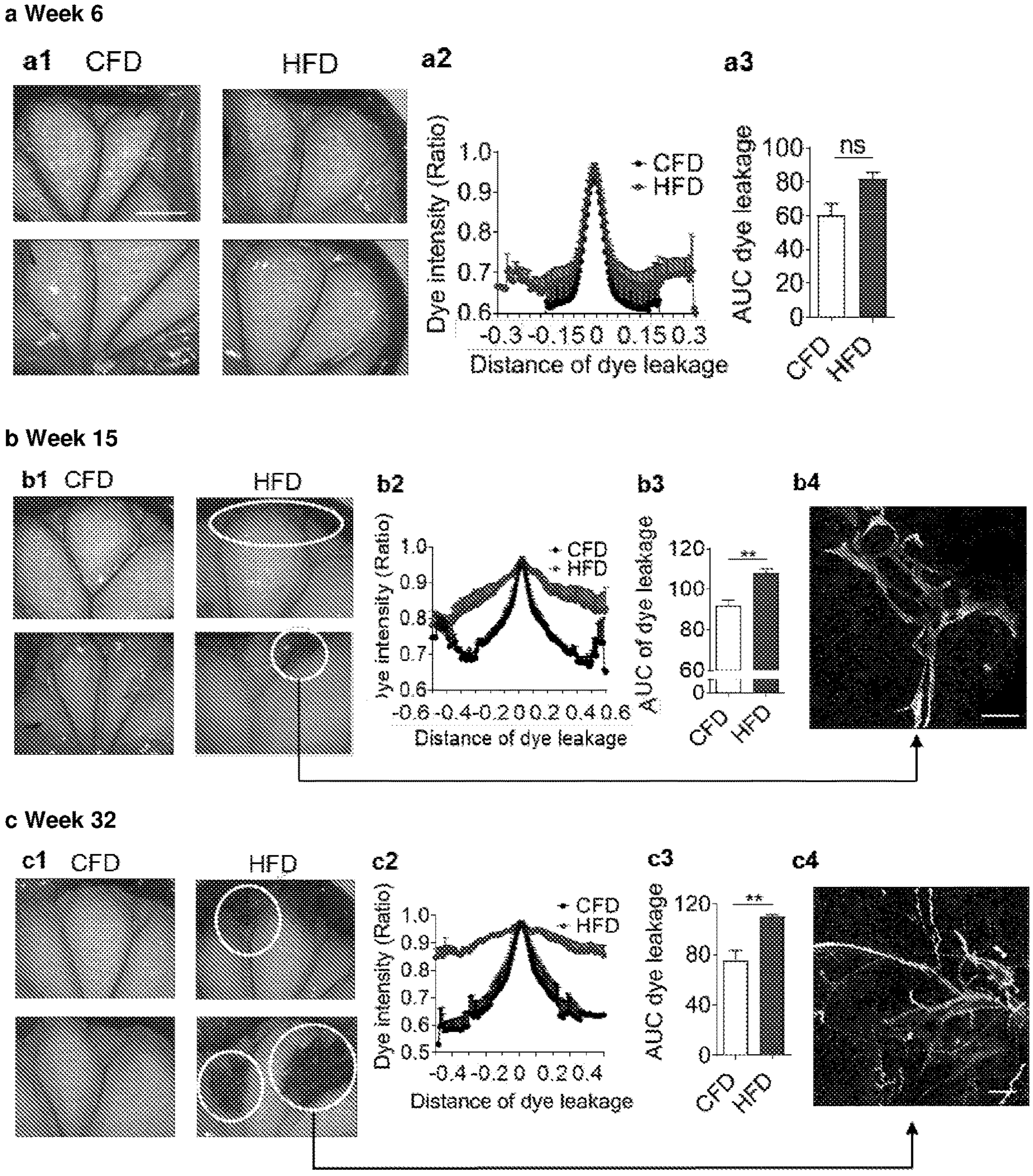
FIG. 2 shows lymph "leakage" into surrounding VAT due to HFD-induced remodelling of the mesenteric lymphatics, as measured by intramucosal injection of Evans blue dye and lymphangiography. Panel a, b and c show data for week 6, 15 or 32 of CFD or HFD feeding, respectively. (a1, b1, c1) Representative images of Evans blue dye passage through mesenteric lymph vessels and leakage to surrounding VAT 10 min after intramucosal dye injection. Scale bar, 5 mm. White circles show major sites of lymph leakage. (a2, b2, c2) Quantification of lymph leakage to VAT. Graphs show Evans blue dye intensity at the center of the vessel (peak of the lines) outward to VAT (lowest point of the lines). (a3, b3, c3) Area under the curve (AUC) of the blue dye intensity plots in a2, b2, c2. (b4 and c4) Representative immunofluorescence images of the mesenteric lymphatic vessels (LYVE-1 (grey)) in VAT showing that the lymphatic vessels are highly branched at sites of lymph leakage (region imaged in b4 and c4 is area circled in white in b1 and c1, respectively, and connected by black arrow). Scale bars in b4/c4, 100 μm. Mean+s.e.m for n=3 mice for week 6, and n=4 mice for week 15 and 32. Statistical differences, $**p<0.01$ from Student's t-test.

FALC in obesity maintained the basic structural characteristics reported previously (see, for example, Koenig, A. & Thaunat, O., "Lymphoid Neogenesis and Tertiary Lymphoid Organs in Transplanted Organs," *Front Immunol.* 7(2016) and Ruddle, N. H. "Lymphatic vessels and tertiary lymphoid organs," *J Clin Invest.* 124, 953-959 (2014)), including the presence of blood vessels, T cells, B cells and variable macrophages. However, while previous reports have noted that FALCs lack lymphatic vasculature, it was determined that some FALCs, particularly in obese mice, contained tortuous lymphatic vessels (FIG. 1*e*1) that occasionally interconnected to an adjacent FALC and/or to branched mesenteric lymphatic vessels in VAT to form a complex lymphatic network (FIGS. 1*e*2 and 8*f*). Taken together, these findings provide evidence of substantial remodelling of the lymphatics in VAT in HFD induced obesity.

Mesenteric Lymphatic Remodelling in HFD-Induced Obesity results in Lymph Leakage from the Mesenteric Lymphatic Vessels in VAT into the Surrounding VAT It has now been found that mesenteric lymphatic remodelling in HFD-induced obesity results in lymph leakage from the mesenteric lymphatic vessels in VAT into the surrounding VAT. As further described herein, this lymph leakage leads to metabolic and inflammatory changes that promote insulin resistance. Accordingly, in one aspect, the present invention provides a method of treating a metabolic disease, disorder or condition in a patient in need thereof, comprising reducing leakage of lymph. In another aspect, the present invention provides a method of treating a metabolic disease, disorder or condition in a patient in need thereof, comprising reducing leakage of lymph into nearby tissue. In another aspect, the present invention provides a method of treating a metabolic disease, disorder or condition in a patient in need thereof, comprising reducing leakage of lymph into proximal VAT. In some embodiments, the method comprises administering to the patient in need thereof an effective amount of a disclosed lipid prodrug.

To assess the drainage and transport function of the remodeled mesenteric lymphatic vessels, Evans blue dye lymphangiography experiments were conducted in mice that were fed a CFD or HFD for 6, 15 or 32 weeks. Evans blue dye was injected into the intestinal mucosa and dye clearance from the injection site via the initial lymphatic vessels, transport through the mesenteric lymphatic vessels in VAT, and leakage to surrounding VAT was visualised and quantified over time. After 6 weeks of HFD feeding, lymphatic drainage appeared efficient and there was no evidence of dye leakage from the lymphatic vessels (FIG. 2 a1-a3). However, in mice fed HFD for 15 weeks there was a significant increase in lymph leakage to VAT relative to CFD fed mice (FIG. 2 b1-b3). Lymphatic vessel leakage progressively worsened with obesity such that after 32 weeks of HFD feeding there was prominent lymph leakage to VAT (FIG. 2 c1-c3). Notably, although lymph leakage into VAT occurred at various points along the lymphatic vessels, it occurred most frequently around the branched and disorganized regions (FIG. 2 b4, c4). Indeed, there was a positive correlation between lymph vessel leakage and the complexity of the local lymph vasculature. These observations suggest that lymph leakage is a result of dysfunctional lymphangiogenesis.

In one aspect, the present invention provides a method of determining lymph leakage in a patient, comprising intramucosal injection of a dye into the gut wall followed by lymphangiography. In another aspect, the present invention provides a method of determining lymphatic integrity in a patient, comprising intra-mucosal injection of a dye into the gut wall followed by lymphangiography. In some embodiments, the dye is Evans blue dye. In some embodiments, the patient is a mammal. In some embodiments, the patient is a rodent. In some embodiments, the patient is a rat or mouse. In some embodiments, the patient is a human. In some embodiments, the patient is a cat or dog.

Leakage of HFD-Modified Lymph Promotes VAT Accumulation and Insulin Resistance

It has now further been found that leakage of HFD-modified lymph promotes VAT accumulation and insulin resistance. Accordingly, in one aspect, the present invention provides a method of treating a metabolic disease, disorder or condition in a patient in need thereof, comprising reducing leakage of lymph. In another aspect, the present invention provides a method of treating a metabolic disease, disorder or condition in a patient in need thereof, comprising reducing leakage of lymph into nearby tissue. In another aspect, the present invention provides a method of treating a metabolic disease, disorder or condition in a patient in need thereof, comprising reducing leakage of lymph into proximal VAT. In some embodiments, the method comprises administering to the patient in need thereof an effective amount of a disclosed lipid prodrug.

To probe the effect of exposure to HFD-modified lymph on adipocyte function, mature 3T3-L1 adipocytes were incubated in vitro with media containing 2% v/v mesenteric lymph fluid obtained from rats fed a HFD or CFD for 6-9 weeks (HFD-lymph or CFD-lymph, respectively). Incubation with HFD-lymph significantly increased intracellular accumulation of lipid droplets and triglycerides in adipocytes, relative to CFD-lymph and control media (FIG. 3*a-c*). The expression of adipogenic genes including PPARγ, leptin and GAPDH, but not ap2 and C/EBPα, were also significantly increased in 3T3-L1 cells when exposed during differentiation to HFD-lymph, but not CFD-lymph, relative to control lymph-free medium (FIG. 3*d*).

Figure 3:
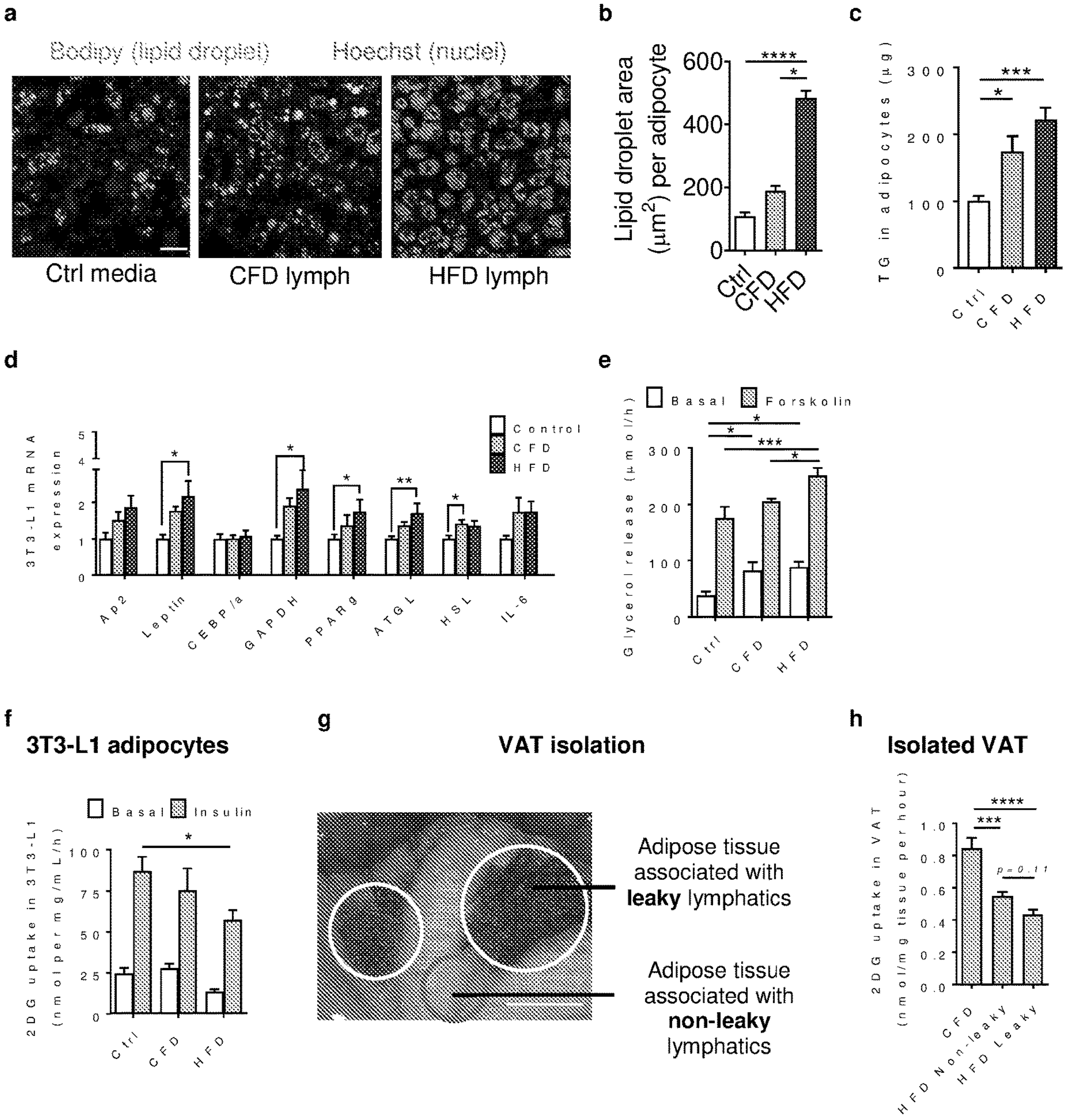
FIG. 3 shows adipocyte differentiation, lipid accumulation, and insulin resistance in VAT and adipocytes exposed to HFD-lymph. Panel a-f show data for 3T3-L1 adipocytes treated with control (ctrl) media or 2% v/v CFD-lymph or HFD-lymph in media. (a) Representative images of lipid droplets (Bodipy, green) in mature adipocytes (nuclei, blue). Scale bar, 100 μm. (b) Average adipocyte area occupied by lipid droplets. Mean±s.e.m for n=7 (ctrl), n=8 (CFD-lymph), n=8 (HFD-lymph) replicates, respectively. (c) Mass of intracellular triglyceride (TG) in mature adipocytes. Mean±s.e.m for n=6 (ctrl), n=6 (CFD-lymph), n=6 (HFD-lymph) replicates, respectively. (d) Real time PCR analysis of PPARγ, leptin, CEBP/a, GAPDH, leptin, Ap2 and IL-6 mRNA expression in adipocytes. Mean±s.e.m for n=6-9 replicates from N=3 independent experiments. (e) Lipolysis in mature adipocytes (from glycerol release) in basal and forskolin-stimulated conditions. Mean±s.e.m for n=6, 5, 6 (basal) and 5, 5, 5 (forskolin) replicates from N=2 independent experiments. (f) $^{14}C$-2-deoxyglucose (2DG) uptake into mature adipocytes in basal and insulin-stimulated conditions Mean+s.e.m. for n=6, 5, 5 (basal) and n=6, 6, 5 (insulin) replicates of N=2 independent experiments. (g) Microphotograph showing example sites where VAT was isolated adjacent to leaky (white circle) or non-leaky (red circle) lymphatics. Scale bar, 5 mm. (h) Insulin-stimulated 2DG uptake into VAT isolated from CFD mice or HFD mice adjacent to leaky lymphatics or non-leaky lymphatics. Mean±s.e.m for n=6, 7 or 9. Statistical differences, $*p<0.05$, $p<0.01$, $*p<0.005$, or $****p<0.0001$ from two-way ANOVA (e, f, h) and one-way ANOVA (b-c).

The mRNA expression of lipolysis enzymes (ATGL and HSL) was also higher following exposure of adipocytes to HFD-lymph or CFD-lymph during differentiation (FIG. 3*d*). Consistent with this, although exposure to either of CFD-lymph or HFD-lymph significantly increased basal lipolysis in adipocytes relative to control media, only HFD-lymph increased forskolin-stimulated lipolysis, suggesting HFD-lymph enhances the capacity for catecholamine/protein kinase A-stimulated lipolysis (FIG. 3*e*).

It has now further been found that lymph leakage into VAT impairs insulin sensitivity. This was achieved through examination of basal and insulin stimulated $^{14}C$-2-deoxy-glucose ($^{14}C$-2DG) uptake into 3T3-L1 adipocytes treated with CFD-lymph, HFD-lymph or control media in vitro and VAT segments isolated from around leaky lymphatics or non-leaky lymphatics in HFD-fed mice. $^{14}C$-2DG uptake into 3T3-L1 adipocytes was significantly impaired after treatment with HFD-lymph, but not CFD-lymph, compared to control media under insulin-stimulated conditions (FIG. 3*f*). Insulin-stimulated $^{14}C$-2DG uptake was also impaired in VAT isolated from HFD fed mice compared to CFD fed mice and was most impaired in VAT isolated from around leaky versus non-leaky lymphatics in HFD fed mice (FIG. 3*g-h*). Thus, HFD-lymph leakage to VAT causes insulin resistance in local VAT that would contribute to systemic insulin resistance.

Mesenteric Lymph Fluid from Mice with HFD Induced Obesity is Pro-Inflammatory and Pro-Lymphangiogenic Given the results described herein above, HFD-lymph contains factors that promote VAT accumulation and insulin resistance, and HFD-lymph was considered likely to contain factors that promote mesenteric lymphatic remodelling in obesity. Therefore, the inflammatory mediators and cells, and pro-lymphangiogenic factors, in HFD-lymph and CFD-lymph, which may regulate lymphatic vessel growth and VAT inflammation and metabolism were analysed. It has now been found that the concentration of both pro-inflammatory cells and pro-lymphangiogenic mediators in mesenteric lymph and lymph nodes is altered in HFD fed animals.

Accordingly, in some embodiments, the aspect of obesity-associated mesenteric lymphatic dysfunction is elevated levels of pro-inflammatory cells in the lymph. In some embodiments, the aspect of obesity-associated mesenteric lymphatic dysfunction is elevated levels of pro-inflammatory mediators in the lymph. In some embodiments, the aspect of obesity-associated mesenteric lymphatic dysfunction is elevated levels of pro-lymphangiogenic factors in the lymph. In some embodiments, the aspect of obesity-associated mesenteric lymphatic dysfunction is elevated levels of VEGFc in the lymph.

It has now further been found that leakage of HFD-modified lymph promotes VAT accumulation and insulin resistance. Accordingly, in one aspect, the present invention provides a method of treating a metabolic disease, disorder or condition in a patient in need thereof, comprising reducing leakage of lymph. In another aspect, the present invention provides a method of treating a metabolic disease, disorder or condition in a patient in need thereof, comprising reducing leakage of lymph into nearby tissue. In another aspect, the present invention provides a method of treating a metabolic disease, disorder or condition in a patient in need thereof, comprising reducing leakage of lymph into proximal VAT.

Figure 4:
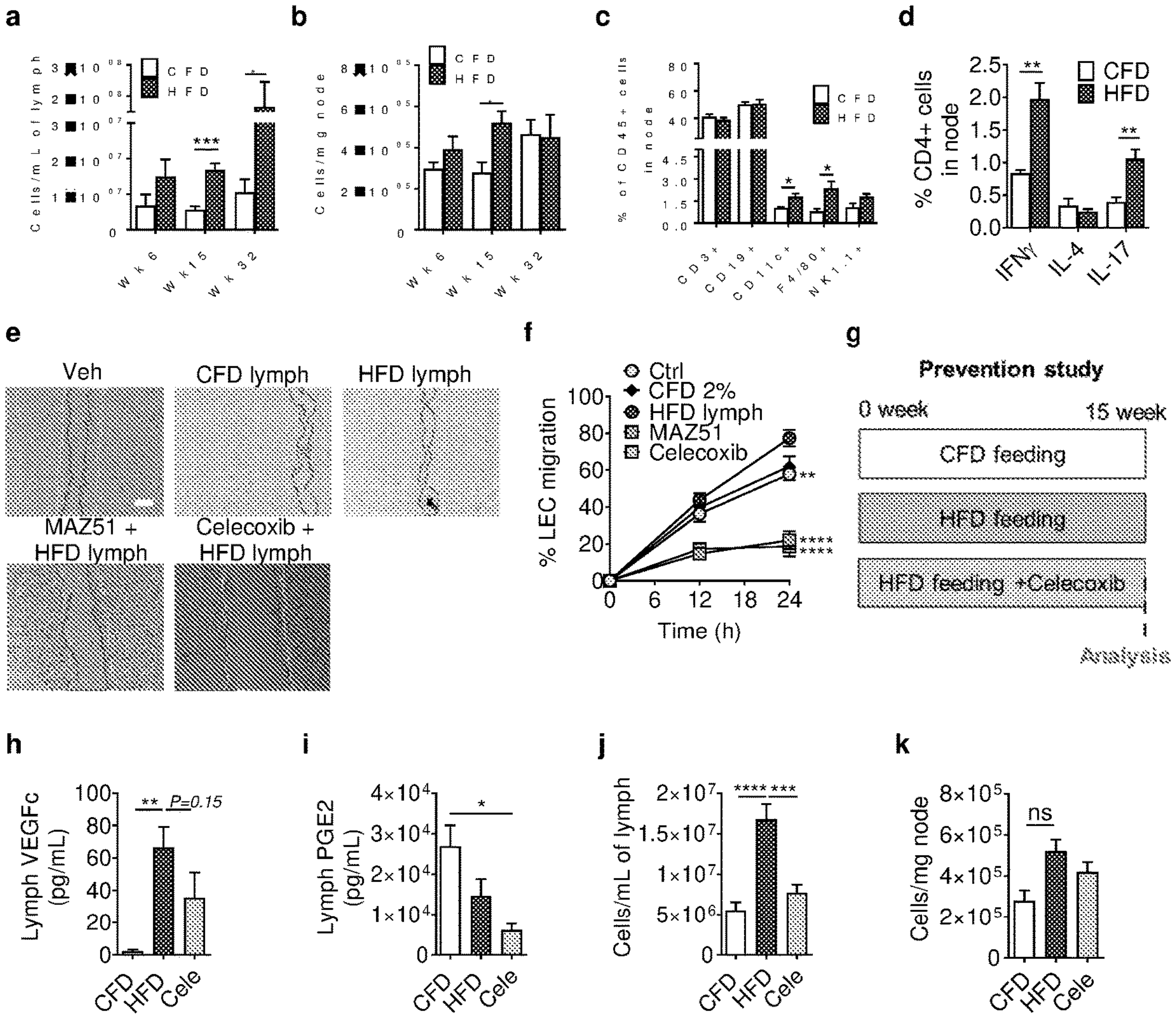
FIG. 4 shows that HFD-lymph is pro-inflammatory and promotes lymphangiogenesis via the COX2 and VEGFc/d-VEGFR3 pathways. (a-b) Total immune cells, (c) percent of CD45+ cells that were T cells (CD3+), B cells (CD19+), dendritic cells (CD11c+), macrophages (F4/80+) and NK cells (NK1.1), and (d) percent of T cells that were Th1 (IFNγ+), Th2 (IL-4+) and Th17 (IL-17+) cells in mesenteric lymph fluid and/or nodes of mice fed CFD or HFD for 6, 15 or 32 weeks. (e) Representative images of LEC migration (white, initial scratch; blue, 24 h) and (f) quantification of LEC migration over time on incubation with control media (ctrl) or 2% v/v HFD-lymph±VEGFR3 inhibitor MAZ51 or COX-2 inhibitor celecoxib. Scale bar, 100 Mean+s.e.m. of n=11, 9, 6 or n=5 for N=2-4 independent experiments. (g) Timeline for celecoxib prevention study. (h-i) VEGFc and PGE2 concentration in lymph. Mean+s.e.m. for n=4, 5 or 4 mice (VEGFc) and n=5, 6 or 5 mice (PGE2). (j-k) Total immune cells in mesenteric lymph or node. Statistical differences from Student's t-test (a-d) or one-way ANOVA (g-k), $*p<0.05$, $p<0.01$, $*p<0.001$, $****p<0.001$. (l) Representative immunofluorescence images (LYVE-1 (green), Hoechst (blue)) and (m) quantification of mesenteric lymphatic vessel branching. Scale bar, 500 μm. Mean+s.e.m. for n=6, 7, 6 mice. (n) Representative images of Evans blue lymphangiography with white circles showing sites of lymph leakage, and (o) quantification (AUC) of lymph leakage into VAT. Scale bar, 5 mm. Mean+s.e.m. for n=4, 4, 5 mice. (p) Percent weight gain over 15 weeks. (q-r) Mesenteric (MAT) and inguinal subcutaneous (SAT) adipose tissue weight. (s) Fasting blood glucose. (t) Blood glucose AUC from 0-120 min after OGTT. Mean+s.e.m (p) n=35, 33, 35, (q-r) n=5, 7, 6, (s-t) n=7, 6, 6 mice. Statistical differences from one-way ANOVA (m-t), $*p<0.05$, $p<0.01$, $*p<0.001$, $****p<0.001$.
Figure 4:
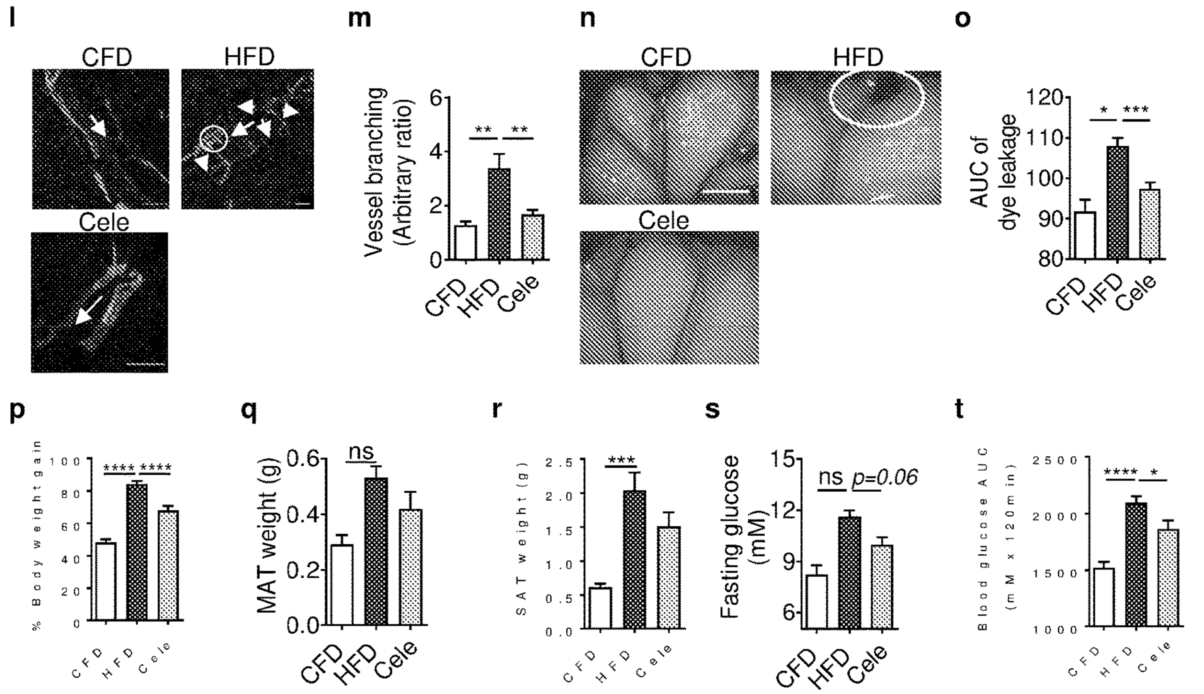

Total immune cell numbers in mesenteric lymph fluid and mesenteric lymph node increased significantly over time in animals fed a HFD compared to a CFD (FIG. 4*a-b*). In general, the proportional distribution of different types of immune cells in lymph fluid and lymph nodes did not differ substantially in HFD and CFD fed mice, but the total numbers of different immune cell types increased in line with the increase in total immune cell numbers. In the lymph nodes there was, however, a 2-3 fold increase in the proportion of CD11c+ dendritic cells, F4/80+ macrophages, Th1 (CD4+INFγ+) and Th17 (CD4+IL-17+) cells with HFD feeding (FIG. 4*c-d*).

The concentration of the key pro-lymphangiogenic factor VEGF-C was also markedly increased (>100 fold) in the mesenteric lymph fluid of HFD versus CFD fed mice (FIG. 4*h*). Moreover, though not statistically significant, the lymph concentration of PGE2, which promotes VEGF-C release from macrophages, was decreased 2-fold with 15 weeks HFD feeding (FIG. 4*i*). Without wishing to be bound by theory, this may reflect a negative feedback relationship.

HFD-Lymph Promotes Lymphangiogenesis via the COX2 and VEGFc/d-VEGFR3 Pathways

In view of the above-described elevated levels of the pro-lymphangiogenic factor VEGF-C and decreased PGE2 in HFD-lymph, it has now further been found that lymphangiogenesis (e.g. mesenteric lymphatic branching and lymph leakage) is mediated by the COX2 and VEGFc/d-VEGFR3 pathways. HFD-lymph was found to promote lymphangiogenesis, as measured by an increase in migration of LECs in vitro upon incubation with HFD-lymph relative to control media (FIG. 4*e-f*). It was further found that LEC migration induced by HFD-lymph is inhibited by the COX-2 inhibitor celecoxib and the VEGFR3 kinase inhibitor MAZ51 (FIG. 4*e-f*).

Accordingly, in some embodiments, the methods of the present invention comprise administering to the patient an inhibitor of the COX2 and/or VEGFc/d-VEGFR3 pathways. In some embodiments, the method comprises administering to the patient a VEGFR3 kinase inhibitor. In some embodiments, the VEGFR3 kinase inhibitor is MAZ51. In some embodiments, the method comprises administering to the patient a COX-2 inhibitor. In some embodiments, the COX-2 inhibitor is celecoxib or a disclosed lipid prodrug thereof such as I-1.

COX-2 Inhibition Prevents HFD-Associated Mesenteric Lymphatic Branching and Leakiness, and Improves Obesity and Glucose Tolerance It has now further been found that in vivo administration of the COX-2 inhibitor celecoxib (29 mg/kg/day for 15 weeks, mixed with HFD, timeline in FIG. 4*e*) to mice prevented mesenteric lymphatic remodelling, lymph leakage, and visceral obesity, and improved glucose tolerance. In the mesentery and VAT, celecoxib effectively prevented the increase in mesenteric lymphatic vessel branching and leakiness, and also prevented immune cell accumulation in the mesenteric lymph fluid and nodes of HFD fed mice (FIG. 4*j-o*). Importantly, these protective effects of celecoxib were associated with decreased weight gain, adiposity, and fasting blood glucose levels, as well as improvement in oral glucose tolerance (FIG. 4*p-t*). Further, celecoxib treatment reduced PGE2 and VEGF-C concentration in mesenteric lymph (FIG. 4*e-f*), supporting the theory that inhibition of COX2 and downstream VEGF-C-VEGFR3 signalling attenuates HFD-associated mesenteric lymphatic remodelling, adipose tissue changes and glucose intolerance. In another aspect, the present invention provides a method of preventing a metabolic disease, disorder, or condition in a patient in need thereof, comprising suppression of VAT inflammation. In another aspect, the present invention provides a method of preventing a metabolic disease, disorder, or condition in a patient in need thereof, comprising maintenance of glucose tolerance.

Lymph-Targeted COX-2 Inhibition Reverses HFD-Associated Mesenteric Lymphatic Branching and Leakiness, Visceral Obesity and Insulin Resistance It has now further been found that a lymph-targeted inhibitor of COX-2 (Compound I-1) reversed, more effectively than the non-lymph-targeted COX-2 inhibitor celecoxib, the mesenteric lymphatic dysfunction, visceral obesity, inflammation, glucose intolerance, and insulin resistance associated with obesity. Mice were fed a HFD for 15 weeks to induce moderate lymphatic dysfunction, obesity and insulin resistance (FIG. 4*l-t*) and then treated with a COX-2 inhibitor mixed in HFD feed for 7 weeks (timeline in FIG. 5*a*). The COX-2 inhibitor was administered as celecoxib or as lymph-targeted Compound I-1 (a celecoxib prodrug linked to a glyceride backbone at the 2 position via a self-immolative linker, FIG. 5*b*). The animals were administered a 3.2 fold lower dose of celecoxib in the form of the prodrug (~9 mg/kg/day celecoxib equivalents) compared to parent drug (~29 mg/kg/day) such that any treatment benefit of the prodrug could be ascribed to targeted inhibition of COX-2 in the mesenteric lymphatics and VAT.

The prodrug is designed to incorporate into dietary triglyceride absorption and transport pathways into mesenteric lymph, as described in, for example, WO 2019/046491, WO 2017/041139, and WO 2016/023082, each of which is hereby incorporated by reference in its entirety. Indeed, upon administering celecoxib or an equal mass of Compound I-1 (i.e. ~30% molar ratio), the mass of celecoxib recovered in mesenteric lymph was >10-fold higher for Compound I-1 (FIG. 5*c*; Lymph samples where Compound I-1 was administered were hydrolyzed to simplify quantitative analysis, by converting any possible celecoxib glycerides into parent celecoxib). In contrast, plasma concentrations of celecoxib were lower after administration of the prodrug compared to administration of an equal mass of the parent drug.

Accordingly, in some embodiments, the COX-2 inhibitor is Compound I-1:

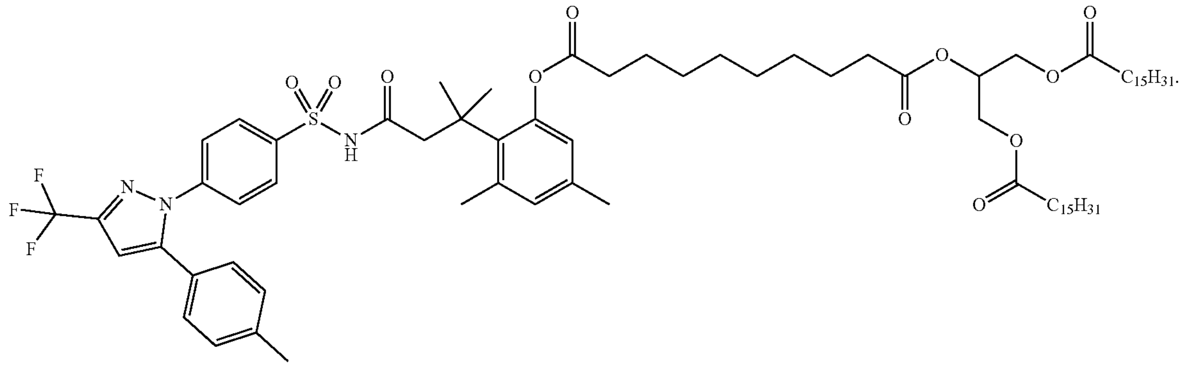

In some embodiments, the inhibitor is a lipid prodrug disclosed herein. In some embodiments, the inhibitor is administered orally. In some embodiments, the inhibitor is delivered selectively to the lymphatic system of the patient.

In some embodiments, the inhibitor is a lipid prodrug that exhibits increased delivery to the patient's lymphatic system at a given dose as compared with a corresponding dose of a non-lipid prodrug form of the inhibitor. In some embodiments, the inhibitor is a lipid prodrug that exhibits 2-fold increased delivery to the patient's lymphatic system at a given dose as compared with a corresponding dose of a non-lipid prodrug form of the inhibitor. In some embodiments, the inhibitor is a lipid prodrug that exhibits 5-fold increased delivery to the patient's lymphatic system at a given dose as compared with a corresponding dose of a non-lipid prodrug form of the inhibitor. In some embodiments, the inhibitor is a lipid prodrug that exhibits 10-fold increased delivery to the patient's lymphatic system at a given dose as compared with a corresponding dose of a non-lipid prodrug form of the inhibitor. In some embodiments, the inhibitor is a lipid prodrug that exhibits 20-fold increased delivery to the patient's lymphatic system at a given dose as compared with a corresponding dose of a non-lipid prodrug form of the inhibitor. In some embodiments, the inhibitor is a lipid prodrug that exhibits 50-fold increased delivery to the patient's lymphatic system at a given dose as compared with a corresponding dose of a non-lipid prodrug form of the inhibitor.

In some embodiments, the inhibitor is a lipid prodrug that exhibits more selective delivery to the patient's lymphatic system at a given dose as compared with a corresponding dose of a non-lipid prodrug form of the inhibitor. In some embodiments, the inhibitor is a lipid prodrug that exhibits 2-fold more selective delivery to the patient's lymphatic system at a given dose as compared with a corresponding dose of a non-lipid prodrug form of the inhibitor. In some embodiments, the inhibitor is a lipid prodrug that exhibits 5-fold more selective delivery to the patient's lymphatic system at a given dose as compared with a corresponding dose of a non-lipid prodrug form of the inhibitor. In some embodiments, the inhibitor is a lipid prodrug that exhibits 10-fold more selective delivery to the patient's lymphatic system at a given dose as compared with a corresponding dose of a non-lipid prodrug form of the inhibitor. In some embodiments, the inhibitor is a lipid prodrug that exhibits 20-fold more selective delivery to the patient's lymphatic system at a given dose as compared with a corresponding dose of a non-lipid prodrug form of the inhibitor. In some embodiments, the inhibitor is a lipid prodrug that exhibits 50-fold more selective delivery to the patient's lymphatic system at a given dose as compared with a corresponding dose of a non-lipid prodrug form of the inhibitor.

In some embodiments, the inhibitor is a lipid prodrug that exhibits reduced plasma concentrations at a given dose as compared with a corresponding dose of a non-lipid prodrug form of the inhibitor. In some embodiments, the inhibitor is a lipid prodrug that exhibits at least 25% reduced plasma concentrations at a given dose as compared with a corresponding dose of a non-lipid prodrug form of the inhibitor. In some embodiments, the inhibitor is a lipid prodrug that exhibits at least 50% reduced plasma concentrations at a given dose as compared with a corresponding dose of a non-lipid prodrug form of the inhibitor. In some embodiments, the inhibitor is a lipid prodrug that exhibits at least 75% reduced plasma concentrations at a given dose as compared with a corresponding dose of a non-lipid prodrug form of the inhibitor.

Accordingly, in some embodiments, the inhibitor is a lipid prodrug that exhibits reduced adverse side effects at a given dose as compared with a corresponding dose of a non-lipid prodrug form of the inhibitor. In some embodiments, the inhibitor is a lipid prodrug that exhibits reduced frequency of cardiovascular adverse events at a given dose as compared with a corresponding dose of a non-lipid prodrug form of the inhibitor.

In some embodiments, the inhibitor is a lipid prodrug that exhibits increased treatment efficacy at a given dose as compared with a corresponding dose of a non-lipid prodrug form of the inhibitor. In some embodiments, the inhibitor is a lipid prodrug that exhibits increased treatment efficacy at a lower dose compared to a non-lipid prodrug form of the inhibitor.

In another aspect, the present invention provides a method of treating a metabolic disease, disorder or condition in a patient in need thereof, comprising administering to the patient an effective amount of Compound I-1, or a pharmaceutically acceptable salt thereof. In another aspect, the present invention provides a method of preventing a metabolic disease, disorder or condition in a patient in need thereof, comprising administering to the patient an effective amount of Compound I-1, or a pharmaceutically acceptable salt thereof. In some embodiments, an aspect of obesity-associated mesenteric lymphatic dysfunction is reduced in the patient after receiving treatment. In some embodiments, dysfunctional lymphangiogenesis is reduced in the patient after receiving treatment.

Figure 5:
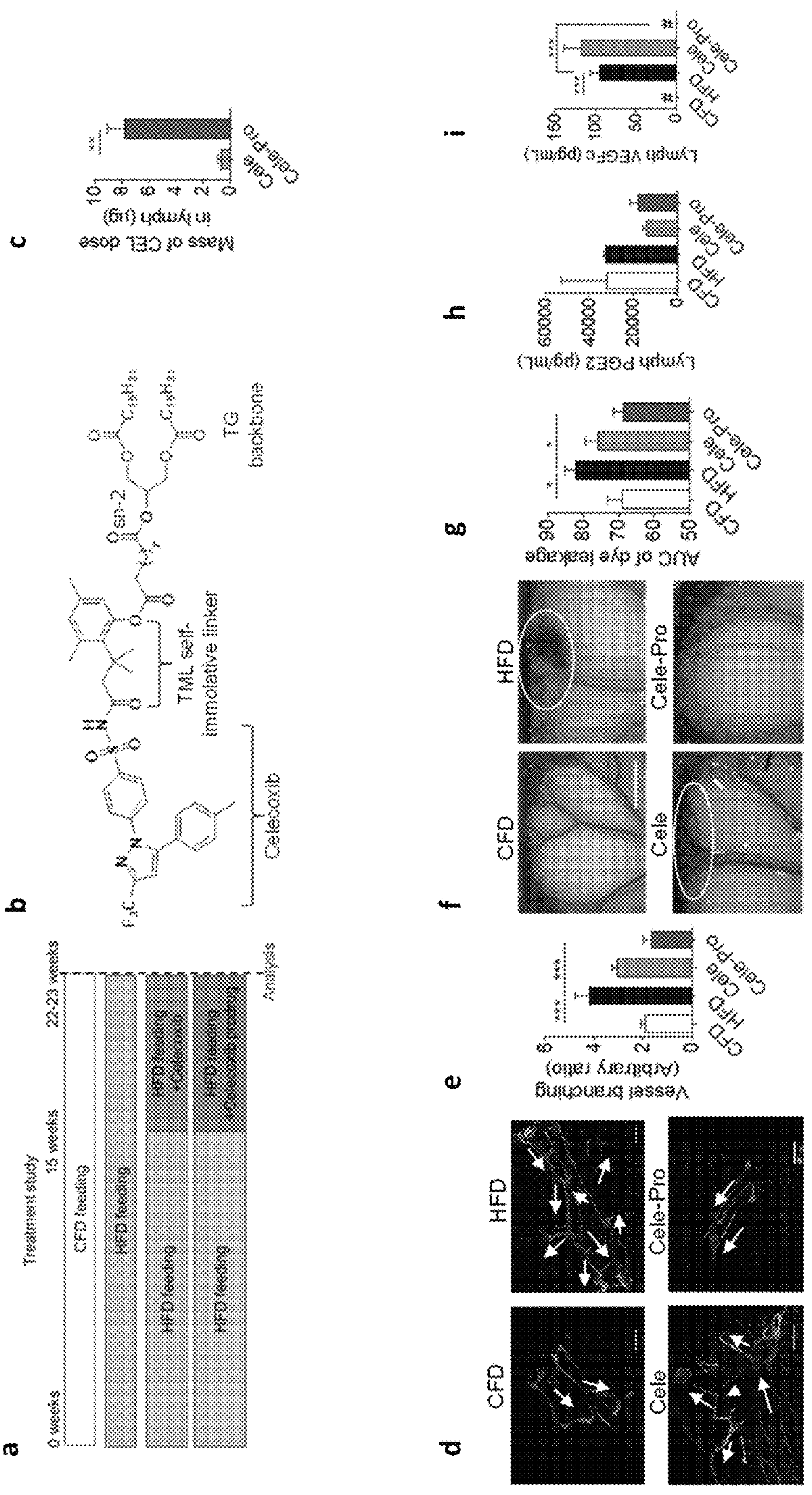
FIG. 5 shows that lymph-targeted COX-2 inhibitor Compound I-1 reverses, more effectively than non-lymph-targeted celecoxib, HFD-induced remodelling of the mesenteric lymphatics, including lymph "leakage" and elevated VEGFc. (a) Timeline of the celecoxib (Cele) and lymph-targeted celecoxib prodrug (Cele-Pro) treatment study. (b) Structure of Compound I-1 in which celecoxib is linked at the sn-2 position of 1,3-dipalmitin via a 10-carbon chain acyl spacer and trimethyl lock (TML) self-immolative group. (c) Total mass of celecoxib recovered in mesenteric lymph (in free or esterified form) over 6 hours after intestinal administration of 0.18 mg Cele or Cele-Pro in a lipid-based formulation. Mean±s.e.m, n=4 or 3 mice. (d) Representative immunofluorescence images of mesenteric lymphatic vessels in VAT (LYVE-1 (green), Hoechst (blue)). Scale bars, 500 μm. (e) Quantification of lymphatic vessel branching in VAT. Mean+s.e.m, n=4 mice all groups. (f) Representative images of Evans blue lymphangiography. Scale bar, 5 mm. (g) Quantification (AUC) of lymph leakage into VAT. White circles show sites of lymph leakage. Mean+s.e.m., n=5, 6, 5, 5 mice. (h-i) PGE2 and VEGFc concentration in mesenteric lymph. Mean+s.e.m., n=3, 4, 3 or 3 (PGE2) and n=4 mice (VEGFc). # is below limit of quantification. Statistical differences from Student's t-test (b) or one-way ANOVA (e-i), *p<0.05, p<0.01, *p<0.005.
Figure 6:
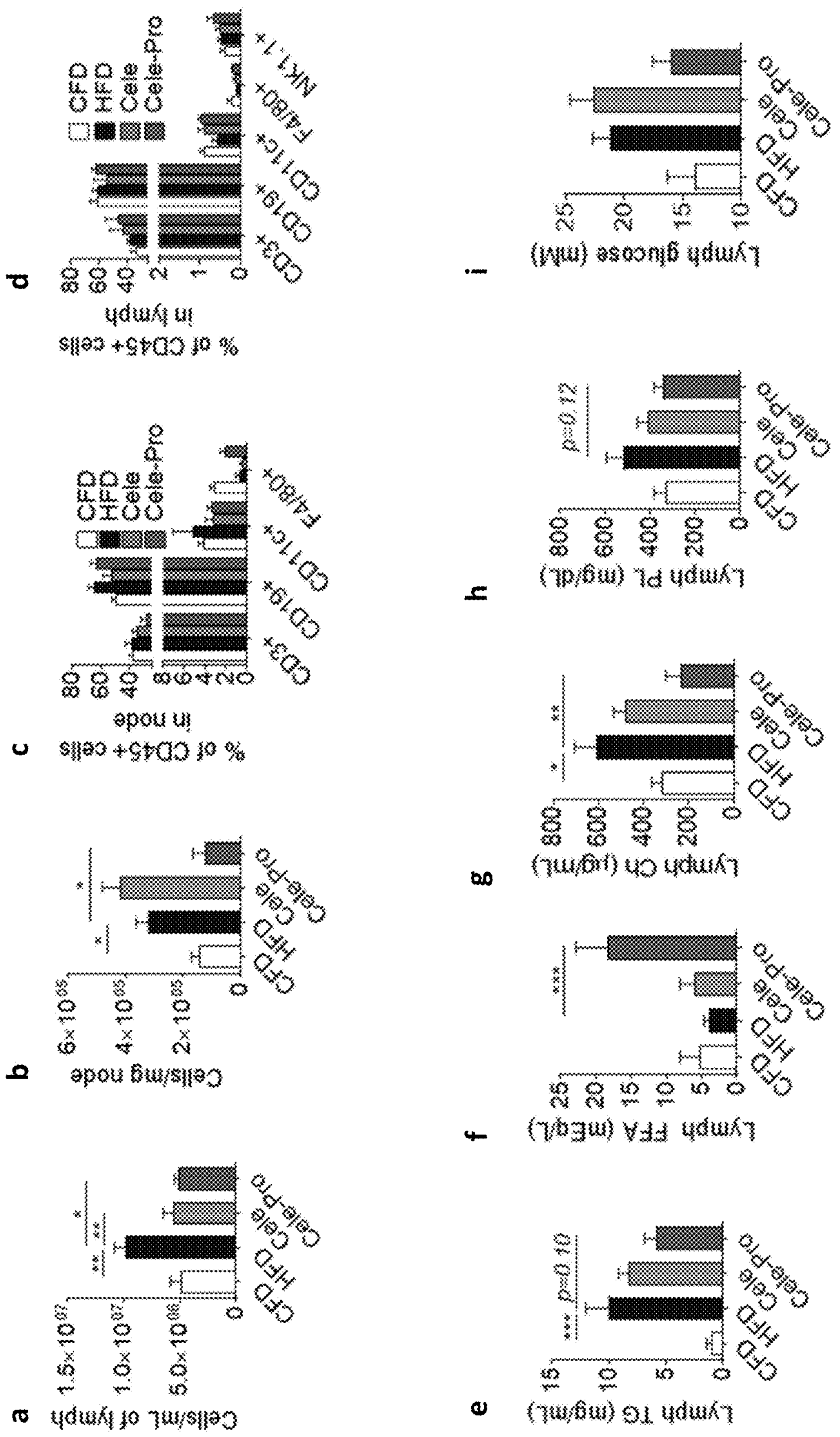
FIG. 6 shows that lymph-targeted COX-2 inhibitor Compound I-1 reverses, more effectively than non-lymph-targeted celecoxib, HFD-induced obesity, insulin resistance, and changes to lymph composition. Data except panel k are for week 22-23 of the celecoxib (Cele) and celecoxib prodrug (Cele-Pro) treatment study as per FIG. 5*a*. (a-b) Total immune cells, and (c-d) Percent of CD45+ cells that were T cells (CD3+), B cells (CD19+), dendritic cells (CD11c+), macrophages (F4/80+) and NK cells (NK1.1) in mesenteric lymph fluid or nodes. Mean+s.e.m., n=10, 11, 6 or 5 mice. (e-i) Triglyceride (TG), free fatty acid (FFA), cholesterol (Ch), phospholipid (PL) and glucose concentrations in mesenteric lymph. Mean+s.e.m., n=4, 8, 6, 7 or 4 mice. (j-k) Unsupervised Principal Component Analysis (PCA) of >500 annotated lipid metabolites in lymph from the treatment (FIG. 5*a* timeline) or prevention (FIG. 4*g* timeline) study. n=4 (CFD), 7 (HFD), 5 (Cele), 3 (Cele-Pro) or n=7 (CFD), 8 (HFD), 8 (Cele) mice. Statistical differences from one-way ANOVA, *p<0.05, p<0.01, p<0.001. Data except panel k are for week 22-23 of the celecoxib (Cele) and celecoxib prodrug (Cele-Pro) treatment study as per FIG. 5***a*. (l) Percent weight gain from 15-22 weeks. (m-n) MAT and inguinal SAT weight. (o) Fasting blood glucose. (p) Blood glucose over time after OGTT. (q) AUC of blood glucose from 0-120 min after OGTT. (r) Fasting plasma insulin. (s) Plasma insulin over time during OGTT. (l) n=9, 9, 12 or 11, (m-n) n=6, 7, 6 or 5, (o-q) n=8, 8, 6 or 8. (r) n=8, 9, 6 or 7. (s) n=8, 9, 6 or 7 (except n=7 for HFD at 30 min and n=6 or 8 for Cele-Pro at 30 min or 60 min) mice. Statistical differences from one-way ANOVA, *p<0.05, p<0.01, **p<0.001.
Figure 6:
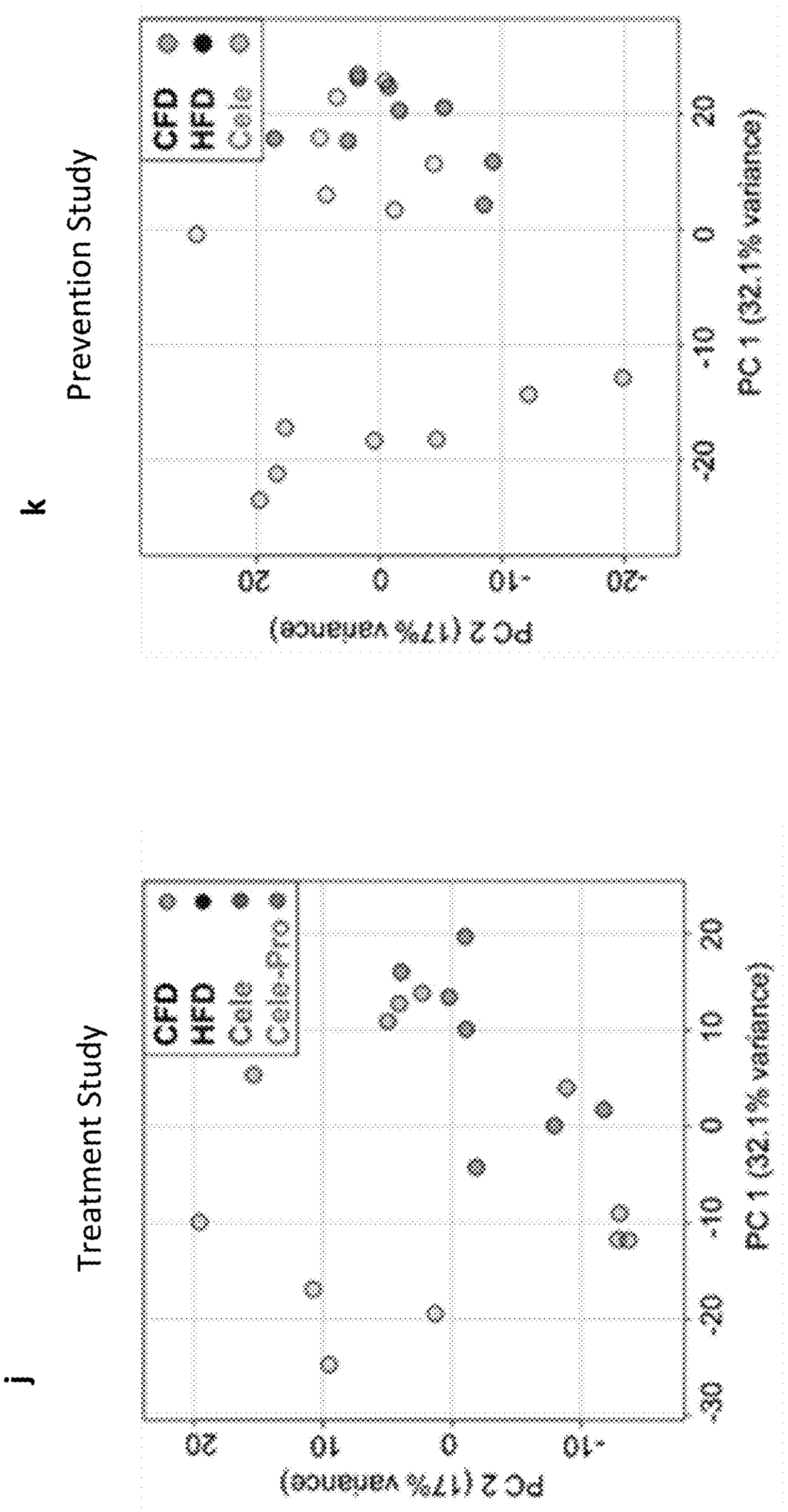
Figure 6:
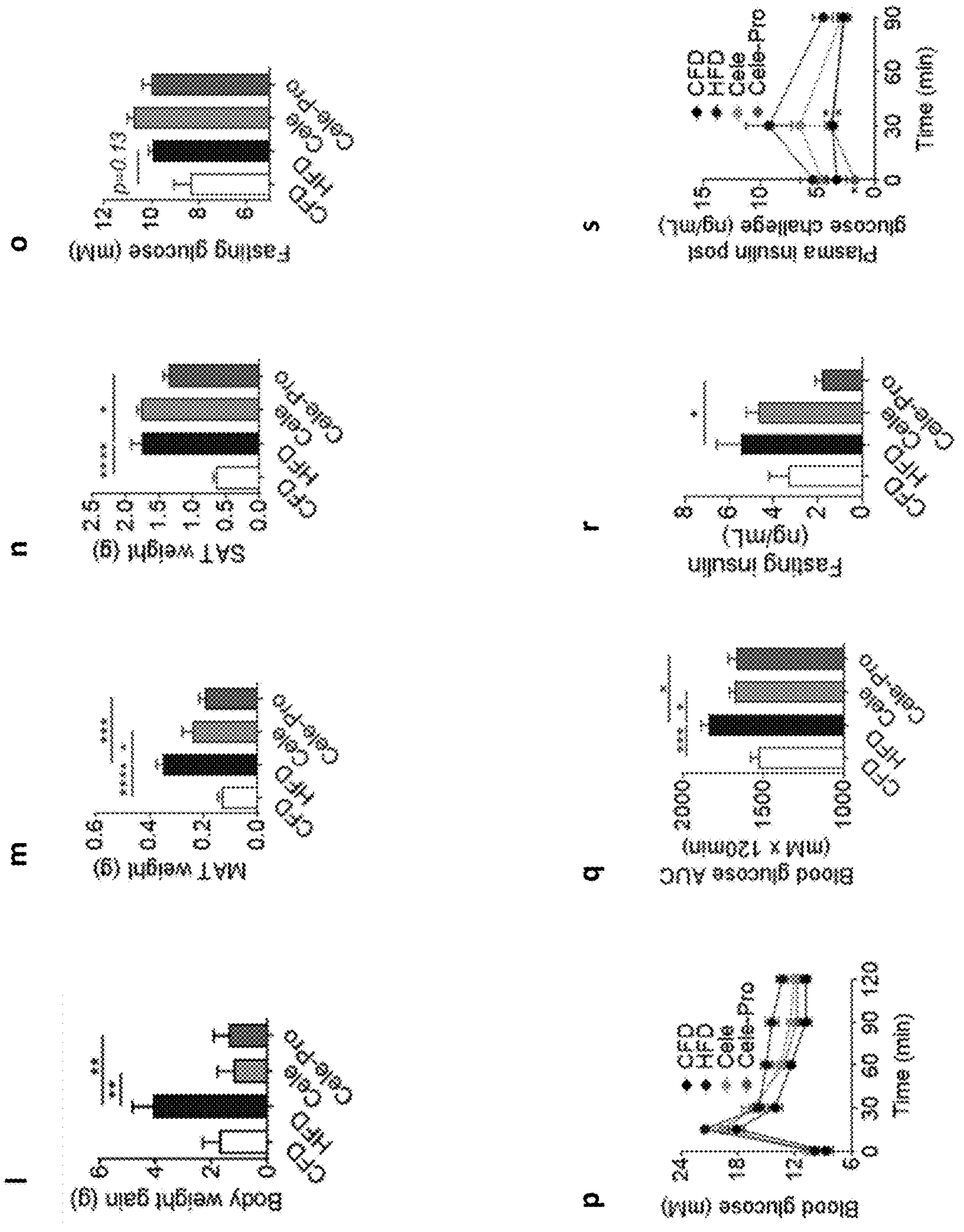

Lipid prodrug Compound I-1 provided superior beneficial effects compared to parent celecoxib. Compound I-1 reversed mesenteric lymphatic branching and lymph leakage into VAT to a level similar to that in CFD fed mice (FIG. 5*d-g*). In contrast, celecoxib treatment at a 3.2-fold higher molar dose was less effective at reversing the lymphatic changes (FIG. 5*d-g* and 4). Treatment with Compound I-1 reduced mesenteric lymph levels of PGE2 and VEGF-C, to below the limit of quantification for VEGF-C, as observed in CFD mice. In contrast, celecoxib treatment reduced PGE2 lymph levels but had no impact on VEGF-C in lymph (FIG. 5*h-i*). Additionally, while both Compound I-1 and celecoxib (at a 3.2-fold higher dose) reduced immune cells in the mesenteric lymph fluid, only Compound I-1, and not celecoxib treatment or prevention, successfully reversed immune cell numbers in mesenteric lymph nodes to levels similar to CFD mice (FIG. 6*b*). The relative proportions of different immune cell types in the mesenteric lymph and/or lymph nodes were not significantly altered across the diet and treatment groups (FIG. 6*c-d*).

Figure 11:
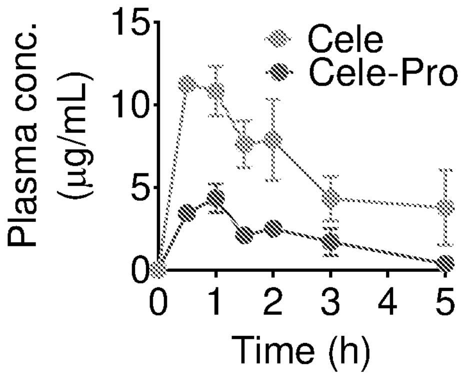
FIG. 11 shows plasma concentrations and AUC of celecoxib following administration of celecoxib or lipid prodrug Compound I-1. (a) Plasma concentrations of celecoxib over time, and (b) Area under the curve (AUC) of celecoxib plasma concentration versus time profile from time 0-5 h following oral gavage of Cele or Cele-Pro to fasted mice in a lipid based formulation at a dose of 29 mg/kg (equivalent, in the case of Compound I-1, to 8.3 mg/kg celecoxib). (a-b) show mean±range of n=2.
Figure 11:
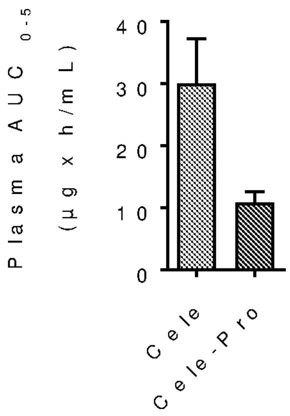
Figure 12A:
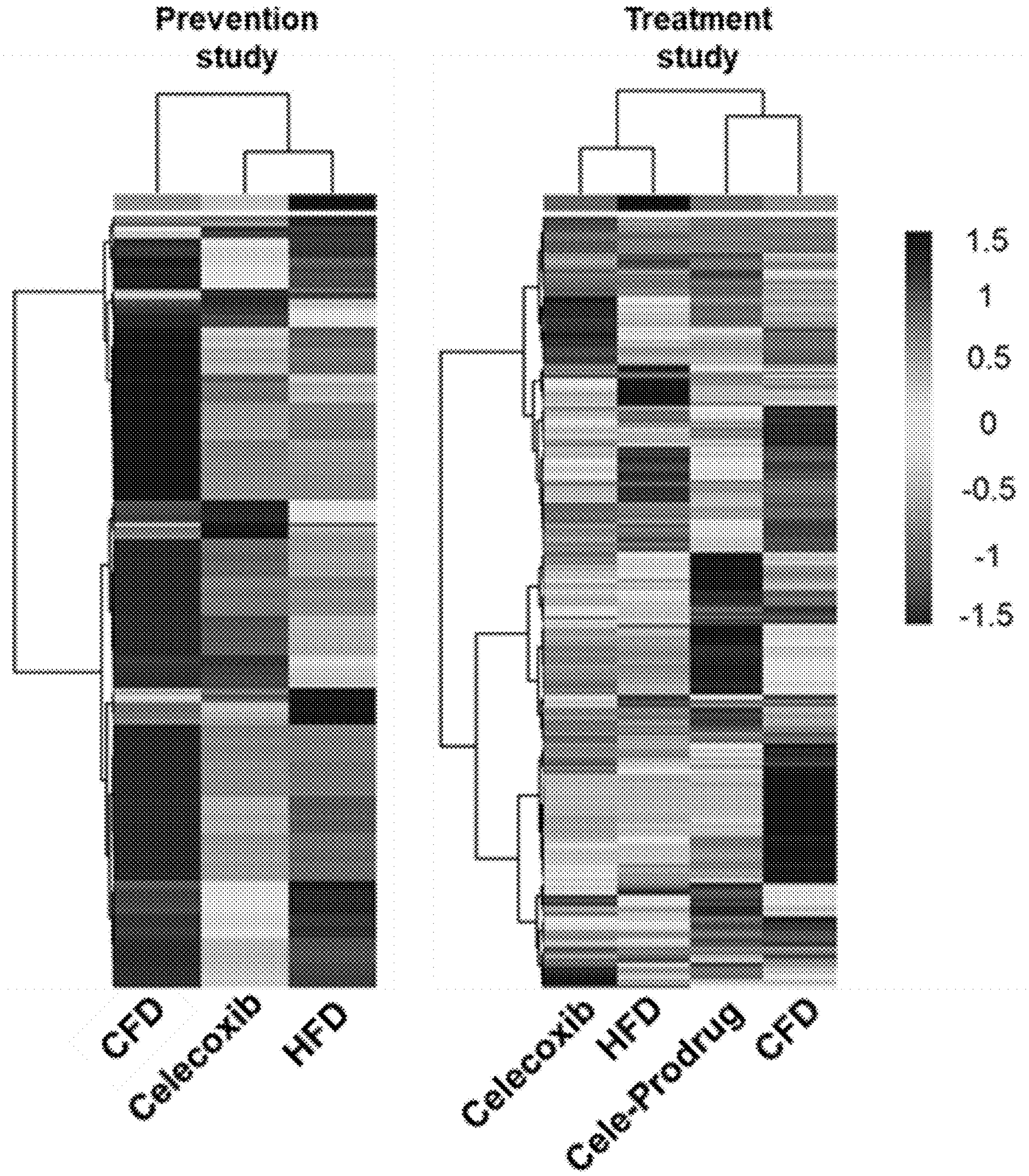
FIG. 12 shows lipid metabolites in mesenteric lymph fluid obtained from mice fed CFD, HFD, HFD plus celecoxib, or HFD plus Compound I-1. (a) Lipidomic analysis heatmap of mesenteric lymph from mice in the prevention study (FIG. 4*g* timeline) or treatment study (FIG. 5*a* timeline). n=4 (CFD), 7 (HFD), 5 (Celecoxib), 3 (Cele-Prodrug) for treatment study or n=7 (CFD), 8 (HFD), 8 (Celecoxib) for prevention study. Lipids were identified based on accurate mass and could represent isomers of the named lipids. (b) Fold change in concentration of significant lipid metabolites including sphingolipids, fatty amides and acyls, glycolipids, sterols, glycerophosphoglycerols, glycerophosphocholines, glycosylphosphatidylinositol, glycerophosphoethanolamines, glycerophosphoinositols in mesenteric lymph from mice in the treatment study. n=4 (CFD), 7 (HFD), 5 (Celecoxib), 3 (Cele-Prodrug) for treatment study or n=7 (CFD), 8 (HFD), 8 (Celecoxib) for prevention study. Lipids were identified based on accurate mass and could represent isomers of the named lipids.
Figure 12B:
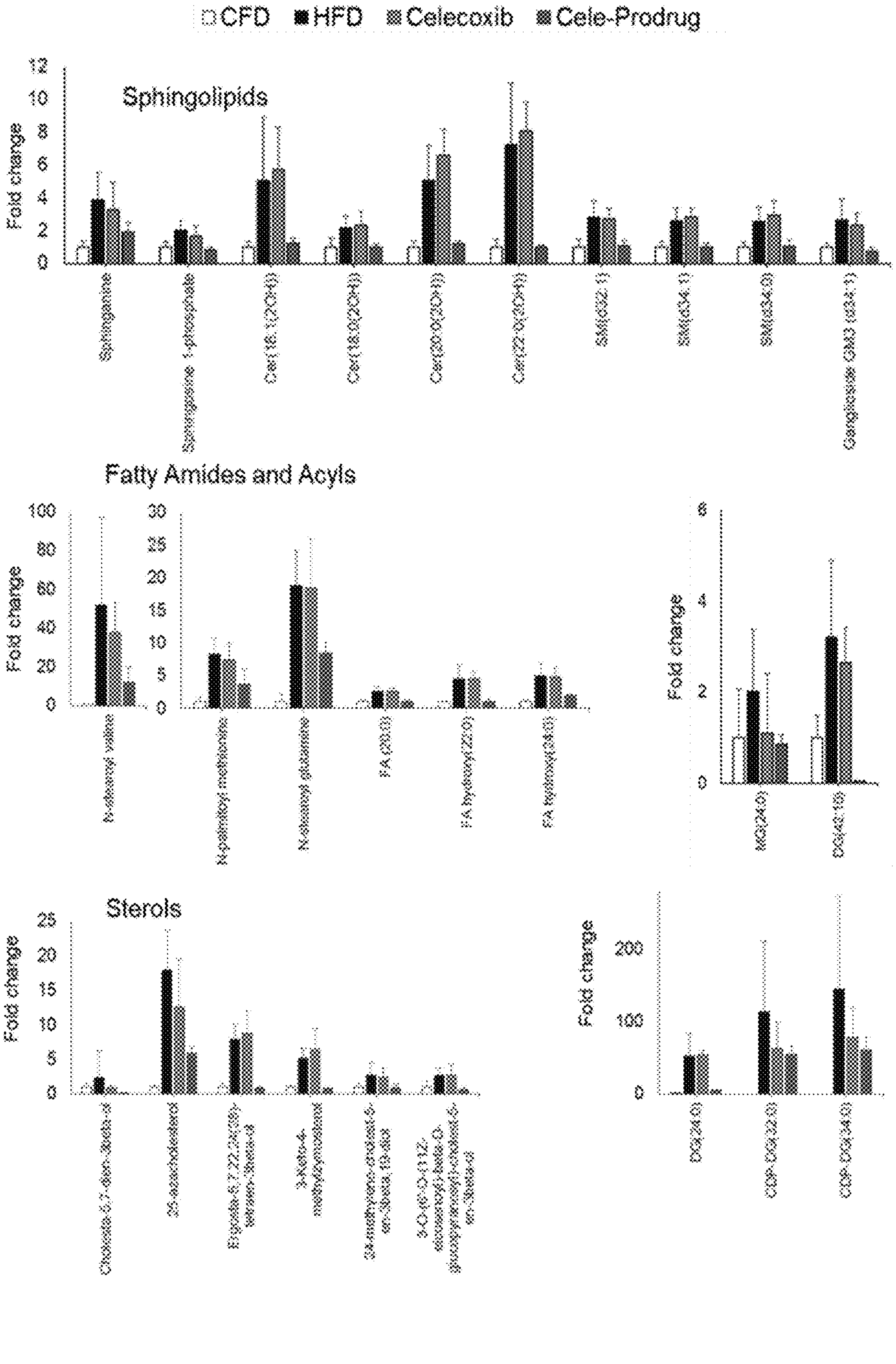
Figure 12C:
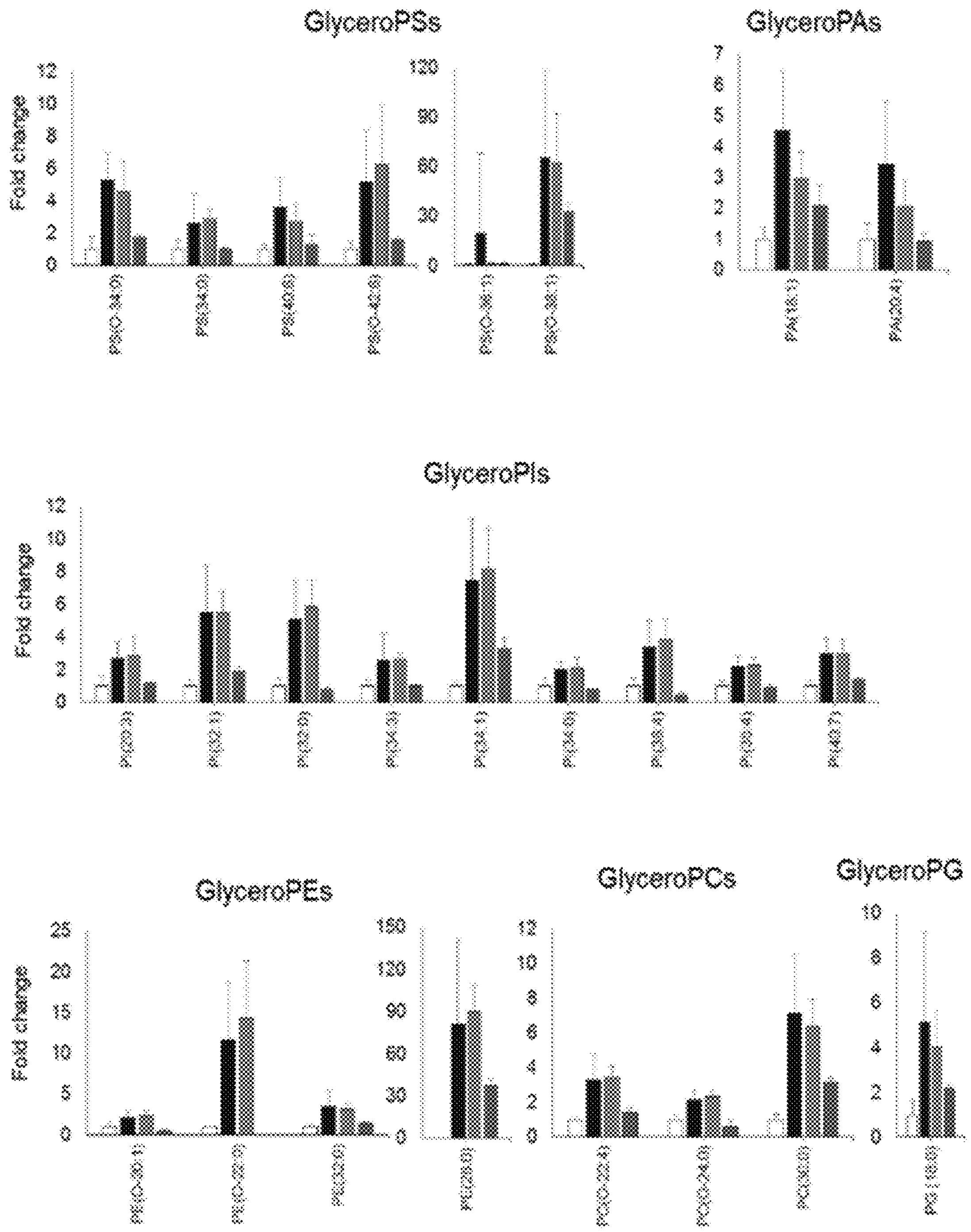

Compound I-1 was also found to have unique impacts on lymph lipid metabolites that regulate lymphatic function and adipose metabolism (see, for example, Turpin, Sarah M., et al. Obesity-Induced CerS6-Dependent C16:0 Ceramide Production Promotes Weight Gain and Glucose Intolerance. *Cell Metab.* 20, 678-686 (2014), and references cited therein). Compound I-1 (but not celecoxib) treatment significantly increased total free fatty acid (FFA) and decreased cholesterol levels in mesenteric lymph. The total concentrations of triglyceride, phospholipid and glucose in mesenteric lymph were not significantly different across groups, although there were trends toward a decrease with prodrug treatment (FIG. 6*e-i*). Remarkably, lipidomic analysis of mesenteric lymph showed a shift in the lymph lipid profile from a HFD-like toward a more CFD-like profile after treatment of the HFD fed mice with Compound I-1 (FIGS. 6*j* and 11*a*) but not with the celecoxib treatment or prevention regime (FIG. 6*j-k*). In general, a range of sphingolipids (including ceramides), sterols and phospholipids (FIG. 14*b*) were significantly increased in HFD-lymph compared to CFD-lymph, consistent with the previously identified roles of ceramides and sphingomyelins in promoting insulin resistance.

Accordingly, in some embodiments, the aspect of obesity-associated mesenteric lymphatic dysfunction is elevated levels of sphingolipids, ceramides, sterols, and/or phospholipids. In some embodiments, the aspect of obesity-associated mesenteric lymphatic dysfunction is elevated levels of ceramides and/or sphingomyelins. In some embodiments, the patient has decreased levels of sphingolipids, ceramides, sterols, and/or phospholipids after receiving treatment. In some embodiments, the patient has decreased levels of ceramides and/or sphingomyelins after receiving treatment.

Similarly, Compound I-1 had overall superior beneficial effects on lymphatic function, adiposity, and insulin resistance compared to systemic COX-2 inhibition with celecoxib (at a 3.2-fold higher dose). Both celecoxib and Compound I-1 significantly reduced body weight gain induced by HFD, but Compound I-1 more significantly reduced both SAT and VAT accumulation, consistent with the reduction in lymph leakage (FIG. 6*l-n*). Compound I-1 also significantly improved oral glucose tolerance (FIG. 6*o-q*) and hyperinsulinemia in the fasted state and after glucose challenge (FIG. 6*r-s*) to levels almost comparable to CFD baseline, suggesting improved insulin sensitivity. In contrast, while parent celecoxib improved oral glucose tolerance, it did not improve hyperinsulinemia (FIG. 6*p-q*).

Accordingly, the methods of the present invention can be characterized by therapeutic improvements experienced by the patient after receiving treatment. In some embodiments, the patient gains weight more slowly after receiving treatment. In some embodiments, the patient loses weight after receiving treatment. In some embodiments, the patient has decreased adiposity after receiving treatment. In some embodiments, the patient has decreased VAT after receiving treatment. In some embodiments, the patient has decreased SAT after receiving treatment. In some embodiments, the patient has decreased fasting blood glucose levels after receiving treatment. In some embodiments, the patient has improved oral glucose tolerance after receiving treatment. In some embodiments, the patient has improved insulin sensitivity after receiving treatment. In some embodiments, the patient has decreased fasting hyperinsulinemia after receiving treatment. In some embodiments, the patient has decreased hyperinsulinemia after glucose challenge after receiving treatment.

Figure 7:
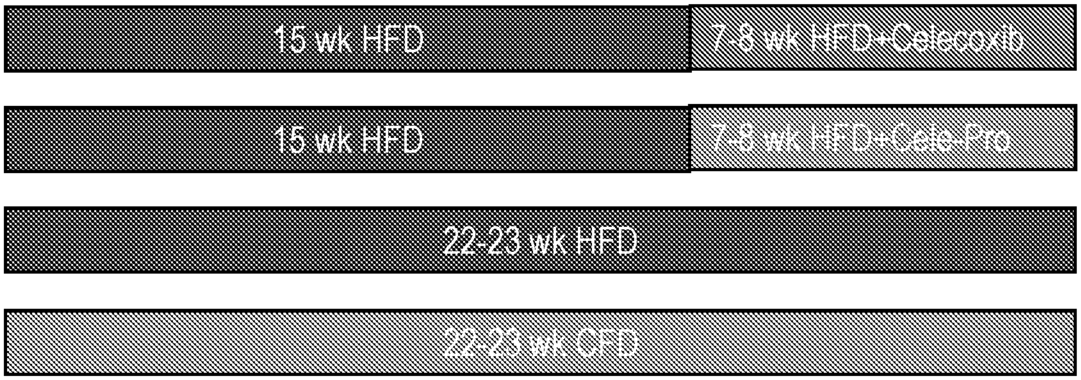
FIG. 7 shows that various doses of lymph-targeted COX-2 inhibitor Compound I-1 reverses, more effectively than higher corresponding doses of non-lymph-targeted celecoxib, HFD-induced induced lymph vessel branching (b-c), lymph leakage (d-e), obesity (k), oral glucose tolerance (f-g), insulin resistance (h-i), weight (k), and changes to lymph composition (j, l). Timelines and treatment groups are shown in panel a. (b-c) n=8 (CFD), 8 (CP90), 4, (CP30), 7 (CP10), 4 (Cele30), 5 (Cele 10), 6 (Cele3) and 4 (HFD). (c-d) n=7 (CFD), 7 (CP90), 5, (CP30), 7 (CP10), 5 (Cele30), 7 (Cele 10), 6 (Cele3) and 7 (HFD). (e-f) n=12 (CFD), 8 (CP90), 6 (CP30), 7 (CP10), 7 (Cele30), 8 (Cele 10), and 6 (Cele3), 8 (HFD). (g-h) n=10 (CFD), 8 (CP90), 6 (CP30), 7 (CP10), 6 (Cele30), 8 (Cele 10), and 7 (Cele3), 11 (HFD). (i-j) n=4 (CFD), 7 (CP 90), 7 (CP 10), 7 (Cele 10) and 6 (Cele 3). Statistical differences from one-way ANOVA, compared to CFD (baseline). *p<0.05, p<0.01, *p<0.005, ****p<0.001.
Figure 7:
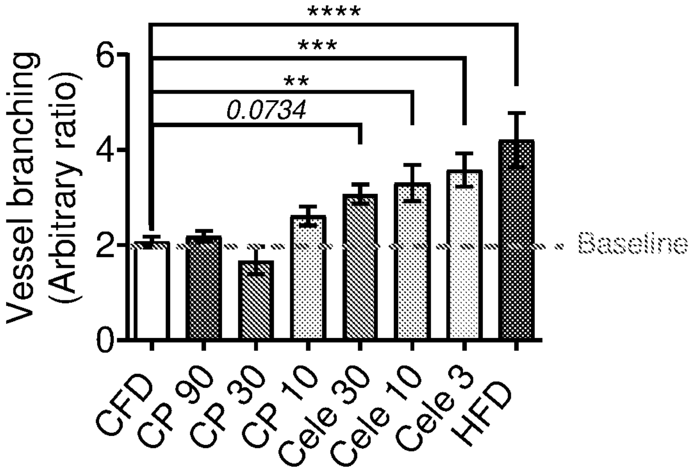
Figure 7:
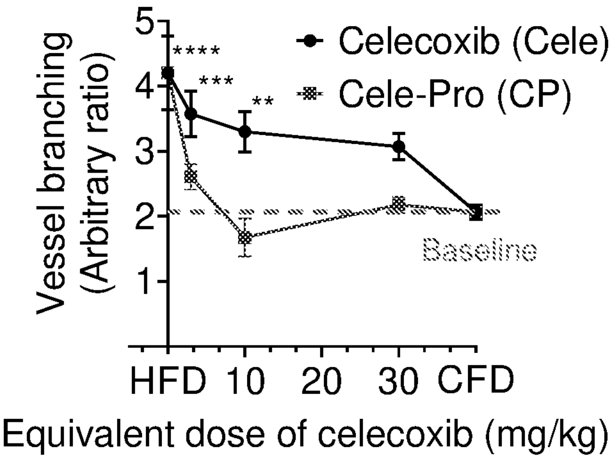
Figure 7:
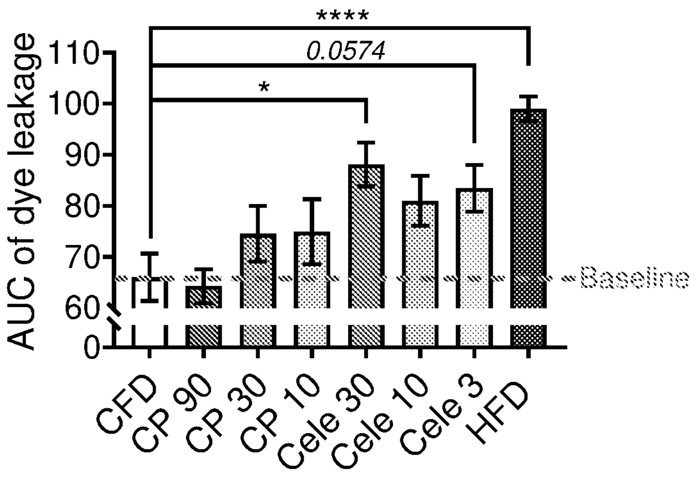
Figure 7:
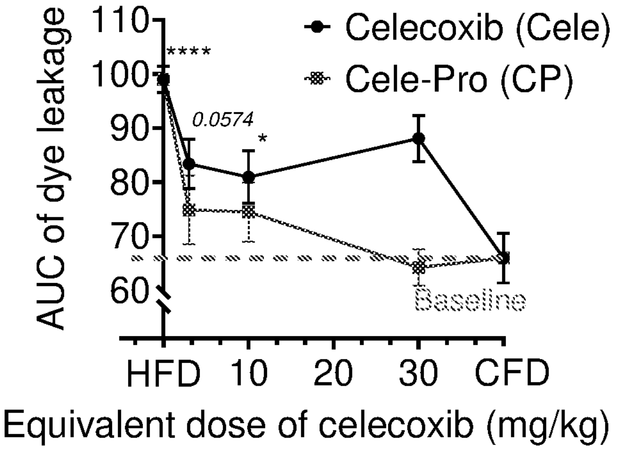
Figure 7:
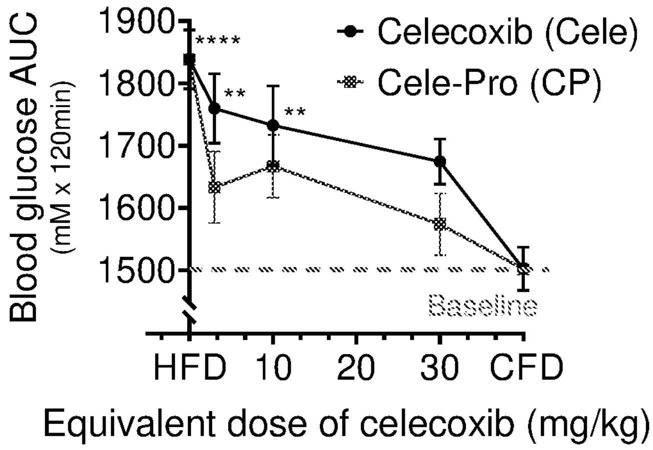
Figure 7:
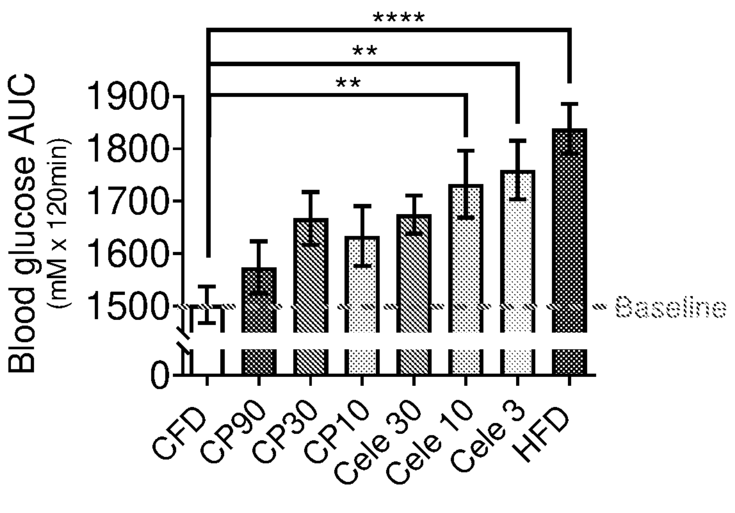
Figure 7:
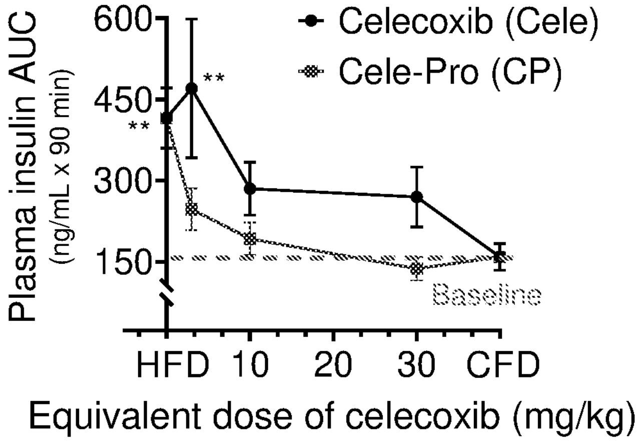
Figure 7:
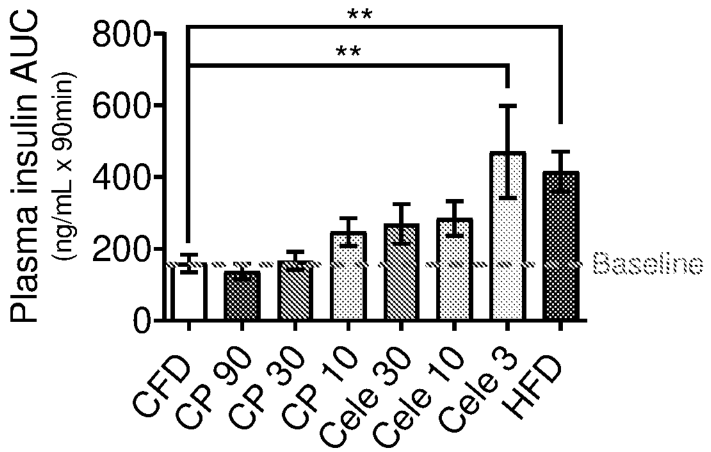
Figure 7:
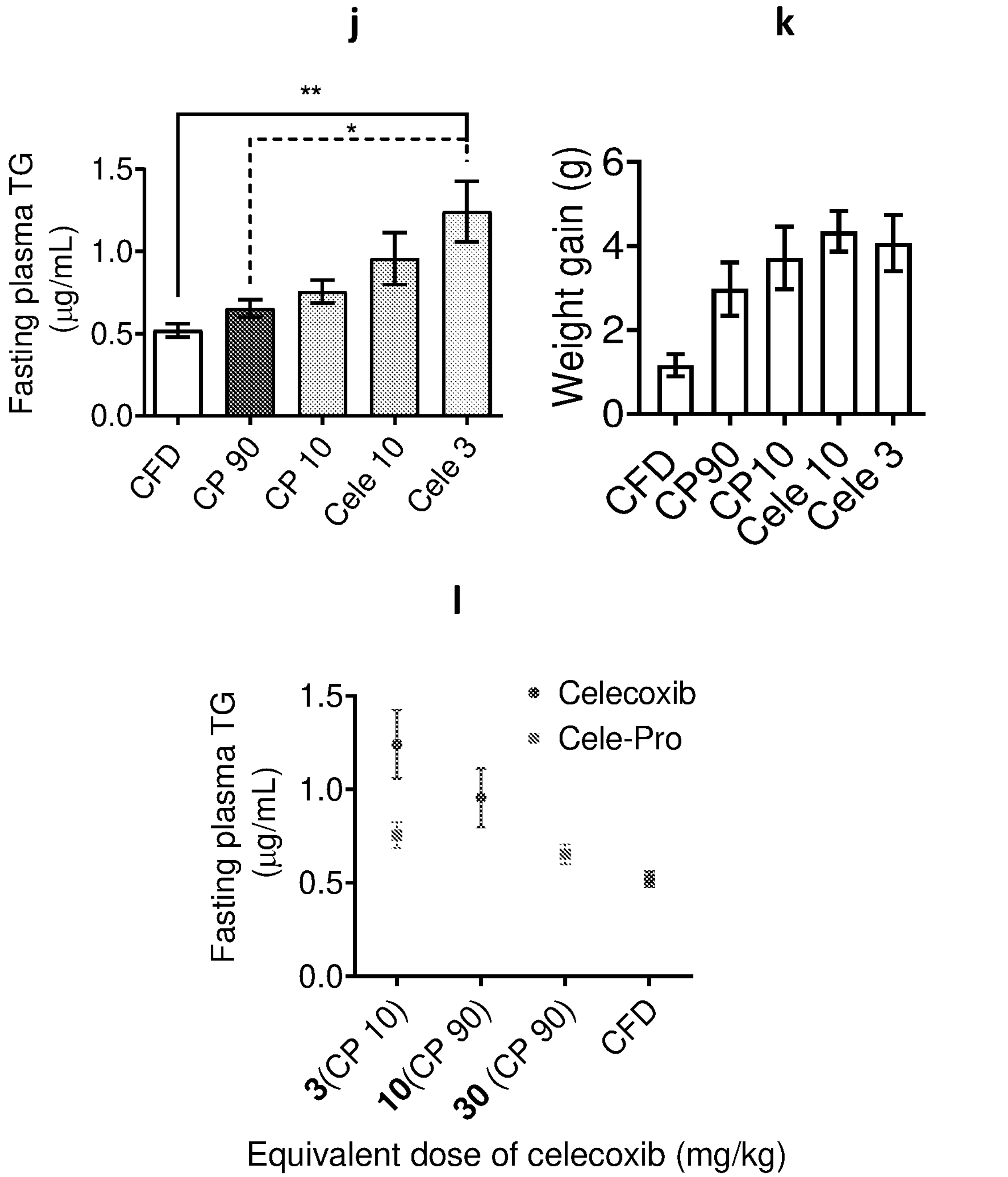

The superior beneficial effect of Compound I-1 relative to celecoxib was demonstrated at doses as low as 10 mg/kg, which is roughly equivalent to a 3 mg/kg dose of celecoxib (FIG. 7). In other words, a ~10-fold lower dose of Compound I-1, relative to celecoxib, was shown to be superior to celecoxib with respect to reversal of VAT lymphangiogenesis (FIGS. 7*a* and 7*b*), and VAT lymph leakage (FIGS. 7*c* and 7*d*), as well as restoration of glycaemic control (FIG. 7*e-h*). Compound I-1 was also shown to be superior to a 3-fold higher dose of celecoxib with respect to reducing fasting plasma triglycerides (FIGS. 7*i* and 7*j*).

Figure 8:
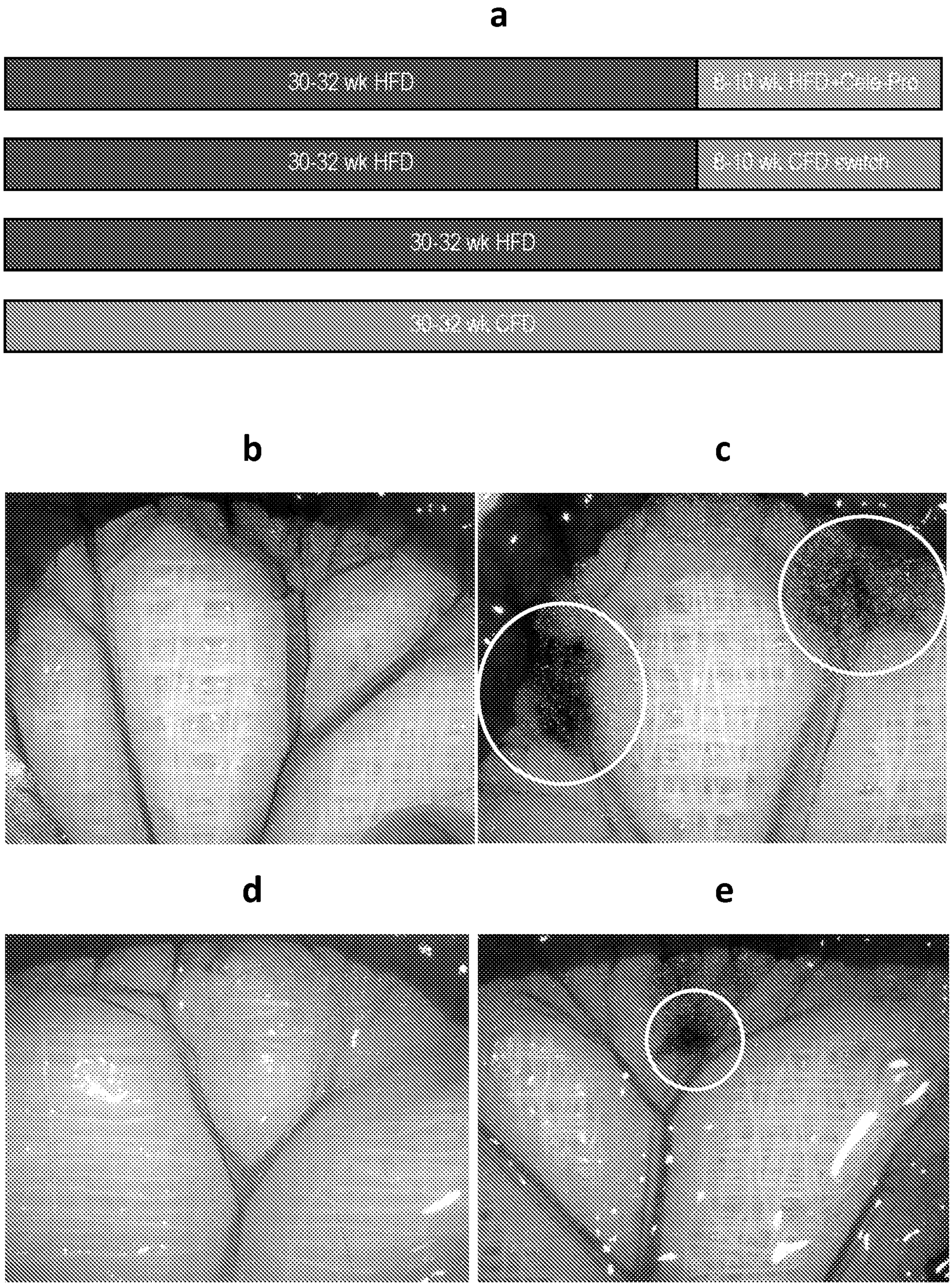
FIG. 8 shows that lymph-targeted COX-2 inhibitor Compound I-1 reverses VAT inflammation, insulin resistance, and lymphatic dysfunction, in chronic HFD-induced obesity models, restoring normal lymphatic function. Details regarding treatment times and controls are shown in panel (a). Panels b-e show lymph "leakage" into surrounding VAT due to HFD-induced remodelling of the mesenteric lymphatics, as measured by intramucosal injection of Evans blue dye and lymphangiography. (f-g) n=2 (CFD), 7 (HFD), 8 (Cele-pro (CP30)) and 5 (CFD switch).
Figure 8:
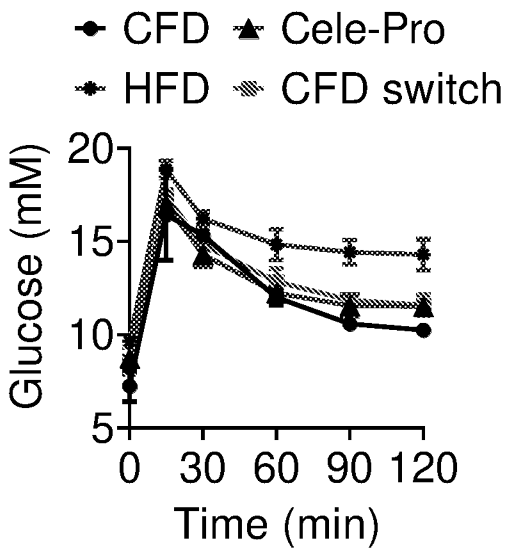
Figure 8:
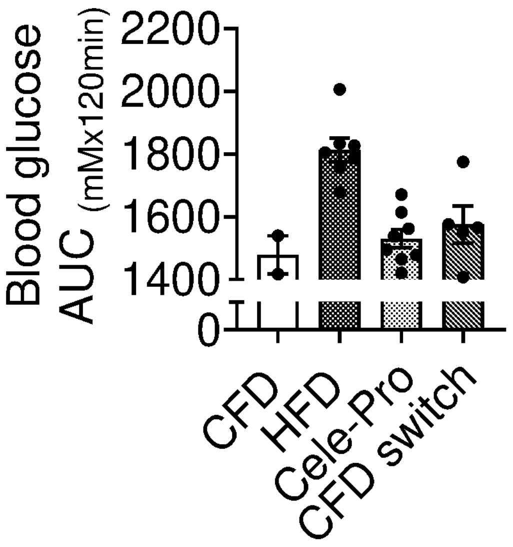
Figure 9:
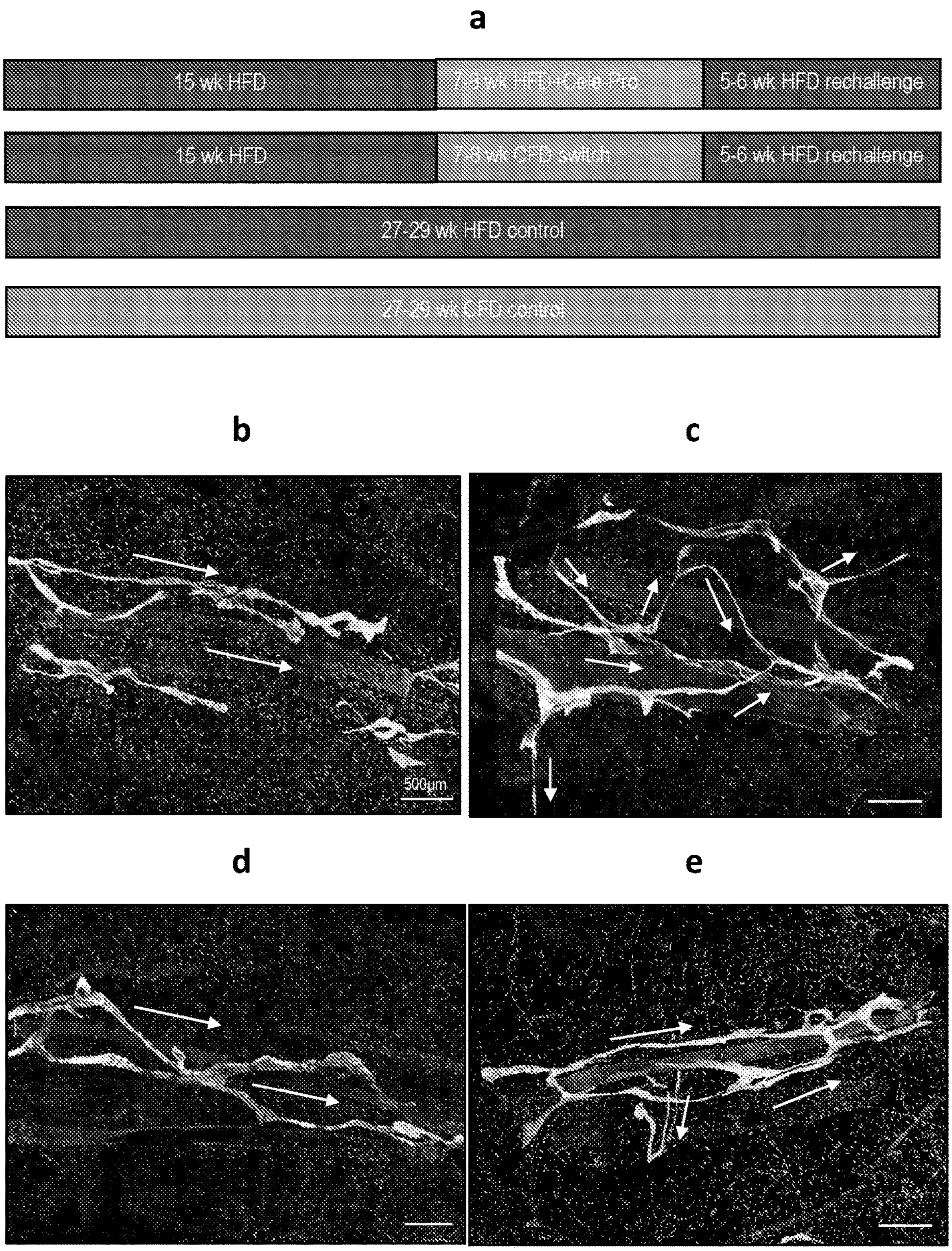
FIG. 9 shows that the effects of Compound I-1 persist after an HFD rechallenge. Details regarding treatment times and controls are shown in panel (a). Panels b-e show whole mount immunofluorescence images of the mesenteric afferent lymph vessels and cell nuclei in VAT of several mouse groups. Panels f-i show lymph "leakage" into surrounding VAT due to HFD-induced remodelling of the mesenteric lymphatics, as measured by intramucosal injection of Evans blue dye and lymphangiography. (j-m) n=5 (CFD), 5 (HFD), 6 (HFD rechallenge-Cele-pro (CP30)) and 5-7 (HFD rechallenge-CFD switch). (a-d) n=5 (CFD), 6 (HFD), 8 (HFD rechallenge-Cele-Pro (CP30)) and 7 (HFD rechallenge-CFD switch).
Figure 9:
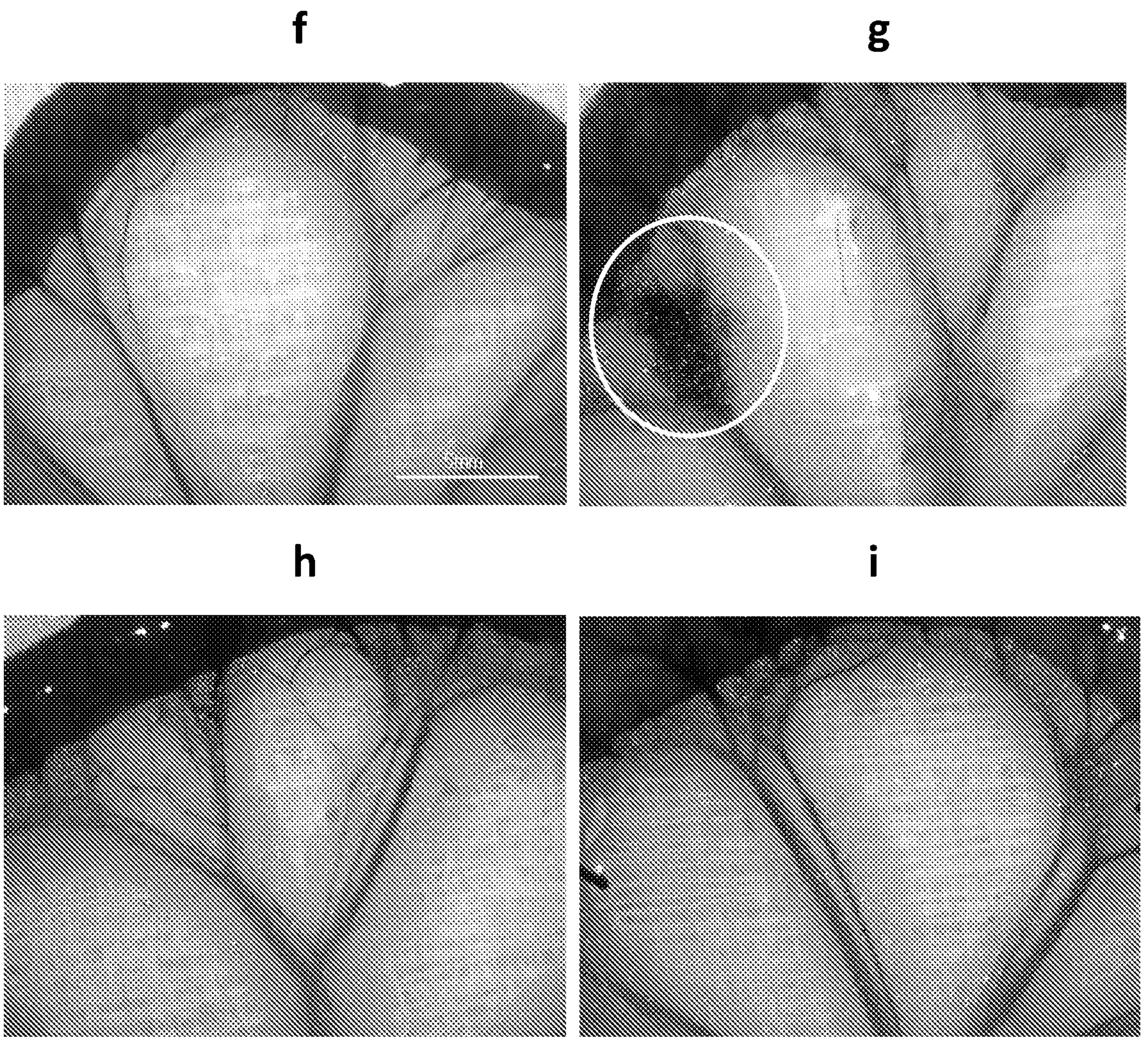
Figure 9:
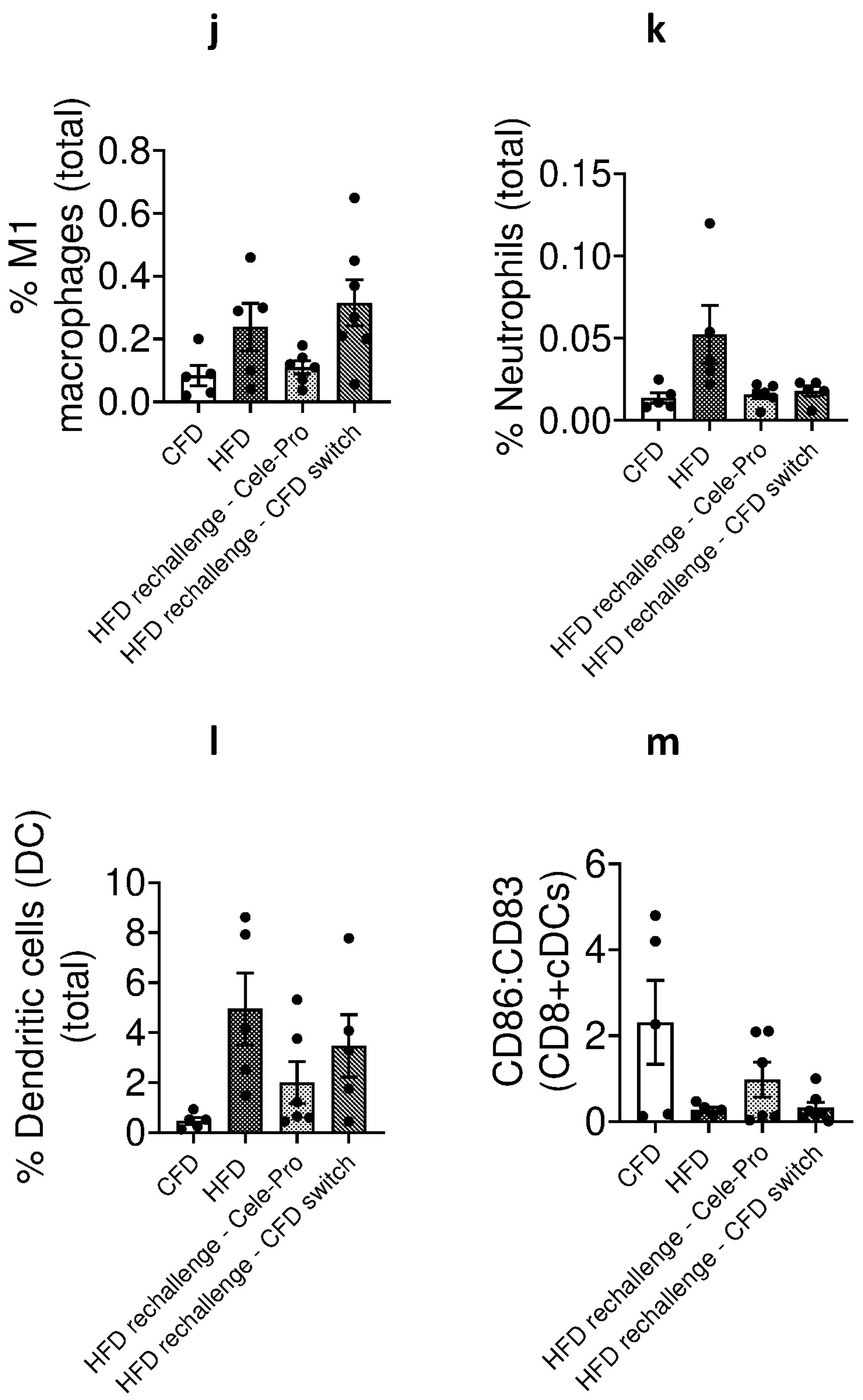
Figure 9:
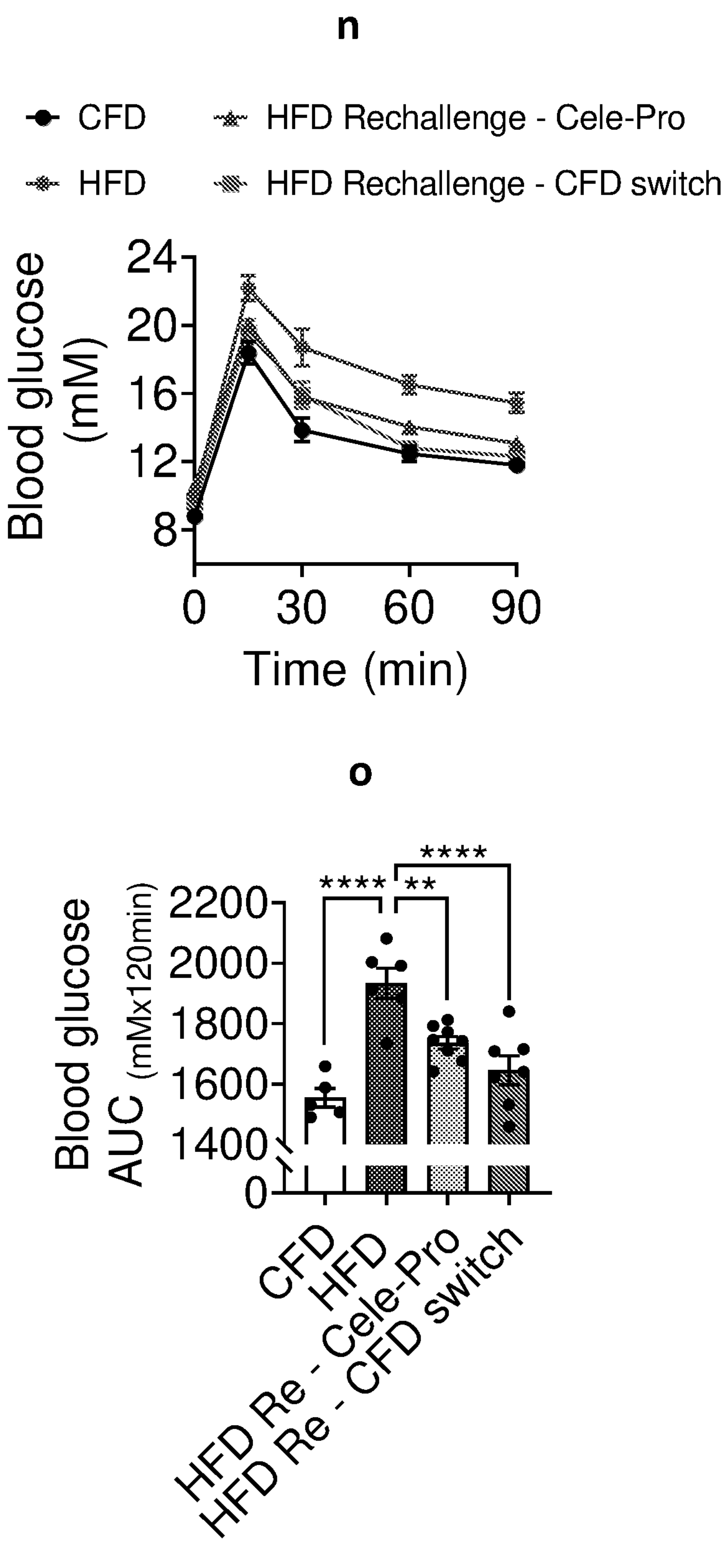
Figure 10:
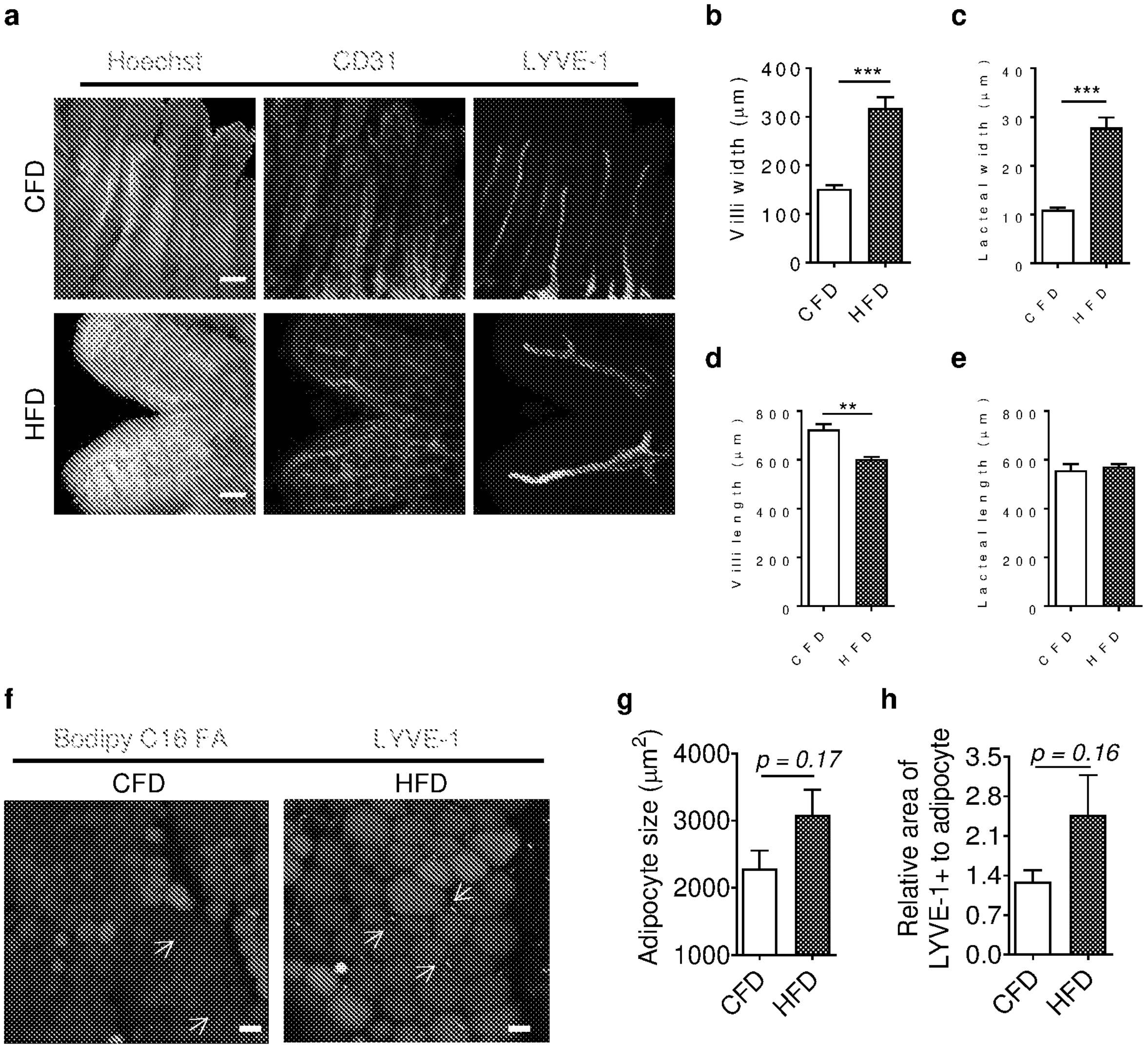
FIG. 10 shows remodelling of the intestinal villi, intestinal lacteals, and lyve1+ cells (lymphatic endothelial cells or macrophages) in VAT of C57BL/6 mice fed a high fat diet (HFD) compared to that of mice fed a chow fat diet (CFD). (a) Representative immunofluorescence images of intestinal villi. Cell nuclei (Hoechst, grey), CD31+ blood vessels (pink) and LYVE-1+ lacteals (green). Scale bars, 100 μm. (b-e) Immunofluorescent quantification of the width and length of the intestinal villi and lacteals. Mean+s.e.m., n=4 or 5 mice with 3-4 intestinal villi analysed per mouse. (e) Representative immunofluorescence images of VAT tissue stained for LYVE-1+ cells (pink, representing either lymphatic endothelial cells (LECs) or macrophages) and lipid droplets (green, Bodipy C16 FA). Scale bar, 50 μm. (f) Immunofluorescent quantification of adipocyte size (μm2) and (g) Ratio of area of LYVE-1+ cells (macrophages or LECs) to adipocytes. Mean+s.e.m, n=4 mice (f) and n=3 or 4 mice (g). Statistical differences, p<0.01, *p<0.005 from Student's t-test.

The effects of Compound I-1 on mice on a high-fat diet were shown to be comparable to those from animals that were switched to a chow-fat diet (FIG. 8). The beneficial effects were shown to persist after reintroducing the mice to a high-fat diet (FIG. 9).

ADDITIONAL CONSIDERATIONS

The mesenteric lymphatic vessel changes described herein (i.e. increased density, branching and leakiness) in the VAT—the adipose tissue depot most correlated with metabolic disease—are in contrast to those reported previously in peripheral lymphatic vessels in rodents and humans with obesity and/or diabetes, where lymphatic vessel density, contractility, and transport properties were consistently decreased. (For rodents, see, for example, Blum, K. S., et al. Chronic High-Fat Diet Impairs Collecting Lymphatic Vessel Function in Mice. *PLoS One* 9, e94713 (2014); Hespe, G. E., et al. Exercise training improves obesity-related lymphatic dysfunction. *J Physiol* 594, 4267-4282 (2016); Torrisi, J. S., et al. Inhibition of Inflammation and iNOS Improves Lymphatic Function in Obesity. *Scientific reports* 6, 19817 (2016); and Weitman, E. S., et al. Obesity impairs lymphatic fluid transport and dendritic cell migration to lymph nodes. *PLoS One* 8, e70703 (2013). For humans, see, for example, Arngrim, N., Simonsen, L., Holst, J. J. & Bülow, J. Reduced adipose tissue lymphatic drainage of macromolecules in obese subjects: a possible link between obesity and local tissue inflammation? *International Journal Of Obesity* 37, 748 (2012); Greene, A. K., Grant, F. D. & Slavin, S. A. Lower-Extremity Lymphedema and Elevated Body-Mass Index. *New England Journal of Medicine* 366, 2136-2137 (2012); and Klimontov, V., et al. The Relationships between Serum Levels of Adipokines, Body Fat Distribution, and Subcutaneous Microvasculature in Type 2 Diabetic Subjects. *Diabetes* 67, 2055—P (2018).)

Within VAT, progressive increases in the branching and leakiness of the mesenteric lymphatic vessels in VAT are evident in HFD-fed compared to CFD-fed mice. Mesenteric lymph leakage is most evident around vessel branch points, suggesting that lymph leakage is a result of dysfunctional lymphangiogenesis. This diet-induced phenomenon in wild-type mice is consistent with previous reports in transgenic mice with dysfunctional lymphatics of (1) increased mesenteric lymphatic vessel permeability in diabetic db/db mice, albeit based on data obtained via ex vivo perfusion of a single isolated lymphatic vessel (Scallan, J. P., Hill, M. A. & Davis, M. J. Lymphatic Vascular Integrity is Disrupted in Type 2 Diabetes Due to Impaired Nitric Oxide Signaling. *Cardiovascular Research* (2015).), and (2) mesenteric lymph leakage and association with obesity in *Prox* $1^{+/-}$ mice (Harvey, N. L., et al. Lymphatic vascular defects promoted by Prox1 haploinsufficiency cause adult-onset obesity. *Nature genetics* 37, 1072-1081 (2005).).

Importantly, it has now been found that mesenteric lymph leakage promotes accumulation, metabolic changes and insulin resistance in VAT of HFD-fed mice that, when reversed, significantly reduces adiposity and improves systemic glycemic control and insulin sensitivity. In contrast to previous studies with transgenic mice with dysfunctional lymphatics, described herein are progressive diet-induced increases in lymph leakage with progression of obesity and insulin resistance in wild-type mice. Insulin resistance in VAT was also most significant at sites around leaky lymphatics in obese HFD-fed mice. VAT metabolism thus appears directly regulated by local lymphatic function in obesity. Without wishing to be bound by theory, this could explain why the expansion of VAT, which surrounds the mesenteric lymphatics, leads to greater metabolic and inflammatory changes, and insulin resistance, than SAT expansion. It is further shown that HFD-lymph promotes changes to adipocyte function including increases in adipogenesis, lipid accumulation and lipolysis. These changes are consistent with pathological changes to VAT in vivo that promote ectopic lipid deposition and inflammation in VAT, muscle and liver, which are key drivers of insulin resistance (see, for example, Lee, M.-J., Wu, Y. & Fried, S. K. Adipose tissue heterogeneity: Implication of depot differences in adipose tissue for obesity complications. *Molecular Aspects of Medicine* 34, 1-11 (2013); Liu, J., et al. Impact of Abdominal Visceral and Subcutaneous Adipose Tissue on Cardiometabolic Risk Factors: The Jackson Heart Study. *Journal of Clinical Endocrinology & Metabolism* 95, 5419-5426 (2010); and Raajendiran, A., Tsiloulis, T. & Watt, M. J. Adipose tissue development and the molecular regulation of lipid metabolism. *Essays Biochem* 60, 437-450 (2016).). HFD-lymph therefore contains factors that alter adipose tissue metabolism.

It has now surprisingly been found, based on the results described herein, that a lymph-targeted inhibitor of COX-2 (Compound I-1) reversed, more effectively than the non-lymph-targeted COX-2 inhibitor celecoxib, the mesenteric lymphatic dysfunction, visceral obesity, inflammation, glucose intolerance, and insulin resistance associated with obesity. While anti-TNFα therapies, COX-2 inhibitors, and VEGFc/d-VEGFR3 inhibitors have been reported to reduce obesity and insulin resistance, these effects have been assumed to be the result of anti-inflammatory action rather than lymphatic effects. (Anti-TNFα therapies: Makimura, H., et al. TNF-α Antagonism with Etanercept Decreases Glucose and Increases the Proportion of High Molecular Weight Adiponectin in Obese Subjects with Features of the Metabolic Syndrome. *The Journal of Clinical Endocrinology & Metabolism* 96, E146-E150 (2011); COX-2 inhibitors: El-Bahrawy, H., Hegazy, S., Farrag, W. & Werida, R. Targeting inflammation using celecoxib with glimepiride in the treatment of obese type 2 diabetic Egyptian patients. *International Journal of Diabetes in Developing Countries* 37, 97-102 (2017); and Hsieh, P.-S., et al. COX-2-mediated Inflammation in Fat Is Crucial for Obesity-linked Insulin Resistance and Fatty Liver. *Obesity* 17, 1150-1157 (2009); VEGF-C-VEGFR3 inhibitors: Karaman, S., et al. Blockade of VEGF-C and VEGF-D modulates adipose tissue inflammation and improves metabolic parameters under high-fat diet. *Molecular metabolism* 4, 93-105 (2014); and Karaman, S., et al. Transgenic overexpression of VEGF-C induces weight gain and insulin resistance in mice. *Scientific Reports* 6, 31566-31566 (2016).).

Lipid Prodrugs for Selective Delivery to the Lymphatic System

According to another embodiment, the present invention provides lipid prodrugs (e.g. of a COX-2 inhibitor, such as celecoxib). The lipid prodrugs of the present invention, and compositions thereof, are useful in promoting transport of a therapeutic agent to the lymphatic system and in subsequently enhancing release of the parent drug, i.e. the therapeutic agent.

In another aspect, the present invention provides a method of treating a metabolic disease, disorder, or condition in a patient in need thereof, comprising administering to the patient an effective amount of a lipid prodrug of Formula I:

I

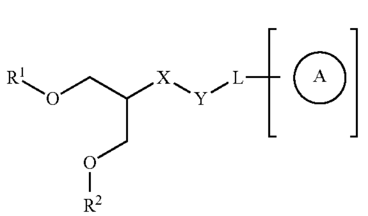

or a pharmaceutically acceptable salt thereof, wherein:

$R^1$ and $R^2$ are each independently hydrogen, an acid-labile group, a lipid, or —C(O)$R^3$;

each $R^3$ is independently a saturated or unsaturated, straight or branched, optionally substituted $C_{1-37}$ hydrocarbon chain;

X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

Y is absent or is —C(O)—, —C(NR)—, or —C(S)—;

L is a covalent bond or a bivalent, saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

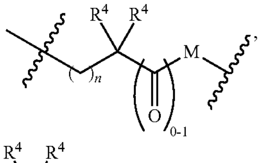

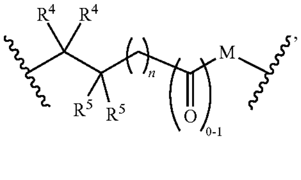

, or

-continued

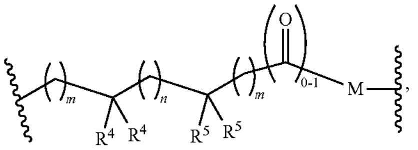

wherein either the right-hand side or left-hand side of L is attached to A;

each -Cy- is independently an optionally substituted 3-6 membered bivalent saturated, partially unsaturated, or aromatic ring having 0-4 heteroatoms independently selected from nitrogen, oxygen, or sulfur;

each $R^4$ and $R^5$ is independently hydrogen, deuterium, halogen, —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —NR$_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;

-M- is a self-immolative group;

n is 0-18;

each m is independently 0-6; and

A is a COX-2 inhibitor.

In another aspect, the present invention provides a method of preventing a metabolic disease, disorder, or condition in a patient in need thereof, comprising administering to the patient an effective amount of a lipid prodrug of Formula I as described herein.

In some embodiments, the present invention provides a lipid prodrug of Formula I, wherein said lipid prodrug is other than Compound I-1:

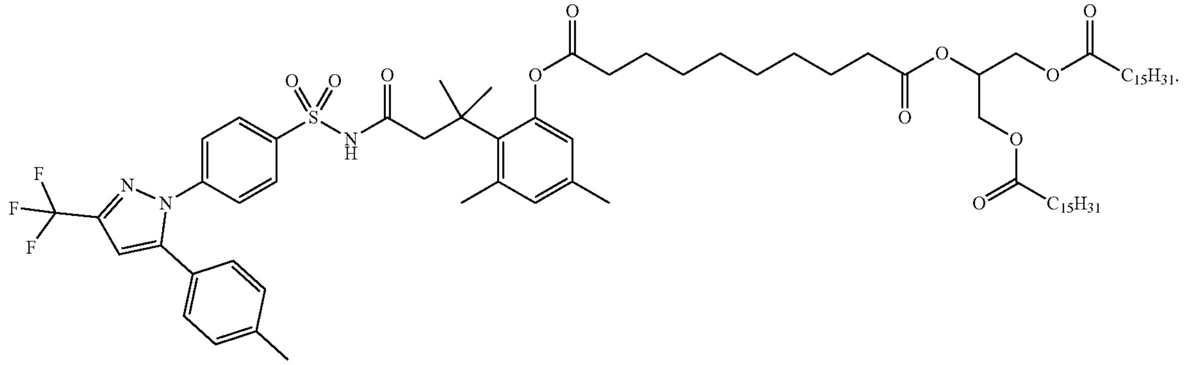

As defined above and described herein, $R^1$ and $R^2$ are each independently hydrogen, an acid-labile group, a lipid such as a fatty acid, or —C(O)$R^3$.

In some embodiments, $R^1$ is hydrogen. In some embodiments, $R^1$ is an acid-labile group. In some embodiments, $R^1$ is a lipid. In some embodiments, $R^1$ is a fatty acid. In some embodiments, $R^1$ is —C(O)$R^3$.

In some embodiments, $R^2$ is hydrogen. In some embodiments, $R^2$ is an acid-labile group. In some embodiments, $R^2$ is a lipid. In some embodiments, $R^2$ is a fatty acid. In some embodiments, $R^2$ is —C(O)$R^3$.

In some embodiments, each of $R^1$ and $R^2$ is independently a fatty acid, phosphatide, phospholipid, or analogue thereof, such as those described in detail below. In some embodiments, each fatty acid is independently a saturated or unsaturated medium-chain or long-chain fatty acid. In some embodiments, each fatty acid independently has a $C_2$-$C_{40}$ chain. In some embodiments, each fatty acid independently has a $C_6$-$C_{20}$, $C_8$-$C_{20}$, $C_{10}$-$C_{20}$, $C_{10}$-$C_{18}$, $C_{12}$-$C_{18}$, $C_{14}$-$C_{18}$, $C_{16}$-$C_{18}$, or $C_{10}$-$C_{16}$ chain. In some embodiments, each fatty acid is independently selected from oleic acid, palmitic acid, EPA, or DHA.

In some embodiments, $R^1$ and $R^2$ are each independently selected from an acid labile group such as tert-butoxycarbonyl (Boc), an amino acid, PEG group, —C(O)OR, —C(O)$NR_2$, —$CH_2$OR, —C(NR)R, or —$P(O)_2$OR.

For clarity, it is understood that, when $R^1$ or $R^2$ is defined as a fatty acid, $R^1$ or $R^2$ is the acyl residue of the fatty acid. Thus, for example, when $R^1$ is defined as palmitic acid, $R^1$ is the acyl portion of palmitic acid, i.e. —C(O)$C_{15}H_{31}$.

As defined above and described herein, each $R^3$ is independently a saturated or unsaturated, straight or branched, optionally substituted $C_{1-37}$ hydrocarbon chain.

In some embodiments, $R^3$ is a saturated, straight, optionally substituted $C_{1-37}$ hydrocarbon chain. In some embodiments, $R^3$ is an unsaturated, straight, optionally substituted $C_{1-37}$ hydrocarbon chain. In some embodiments, $R^3$ is a saturated, branched, optionally substituted $C_{1-37}$ hydrocarbon chain. In some embodiments, $R^3$ is an unsaturated, branched, optionally substituted $C_{1-37}$ hydrocarbon chain.

As defined above and described herein, X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms.

In some embodiments, X is —O—. In some embodiments, X is —NR—. In some embodiments, X is —S—. In some embodiments, X is —O($C_{1-6}$ aliphatic)-O—. In some embodiments, X is —O($C_{1-6}$ aliphatic)-S—. In some embodiments, X is —O($C_{1-6}$ aliphatic)-NR—. In some embodiments, X is —S($C_{1-6}$ aliphatic)-O—. In some embodiments, X is —S($C_{1-6}$ aliphatic)-S—. In some embodiments, X is —S($C_{1-6}$ aliphatic)-NR—. In some embodiments, X is —NR($C_{1-6}$ aliphatic)-O—. In some embodiments, X is —NR($C_{1-6}$ aliphatic)-S—. In some embodiments, X is —NR($C_{1-6}$ aliphatic)-NR—. In any of the foregoing embodiments, 0-2 methylene units of the bivalent $C_{1-6}$ aliphatic group are independently and optionally replaced with —O—, —NR—, or —S— and the bivalent $C_{1-6}$ aliphatic group is independently and optionally substituted with 1, 2, or 3 deuterium or halogen atoms.

As defined above and described herein, Y is absent or is —C(O)—, —C(NR)—, or —C(S)—.

In some embodiments, Y is absent. In some embodiments, Y is —C(O)—. In some embodiments, Y is —C(NR)—. In some embodiments, Y is —C(S)—.

As defined above and described herein, L is a covalent bond or a bivalent, saturated or unsaturated, straight or branched, optionally substituted bivalent $C_{1-30}$ hydrocarbon chain, wherein 0-8 methylene units of L are independently replaced by -Cy-, —O—, —NR—, —S—, —OC(O)—, —C(O)O—, —C(O)—, —S(O)—, —$S(O)_2$—, —C(S)—, —NRS$(O)_2$—, —$S(O)_2$NR—, —NRC(O)—, —C(O)NR—, —OC(O)NR—, —NRC(O)O—, or an amino acid; and wherein 1 methylene unit of L is optionally replaced with -M-; or L is

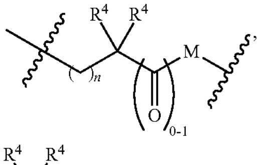

,

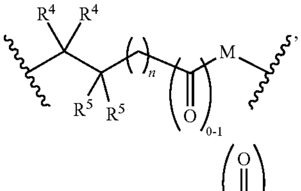

, or

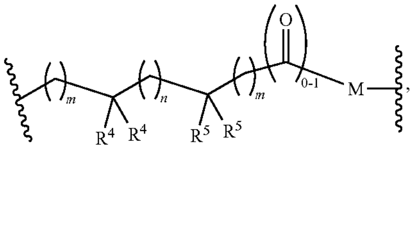

, wherein either the right-hand side or left-hand side of L is attached to A.

In some embodiments, L is a covalent bond. In some embodiments, L is a bivalent, saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-. In some embodiments, L is

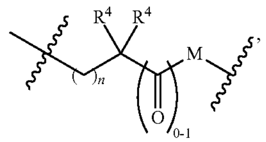

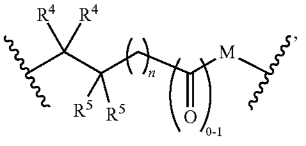

or

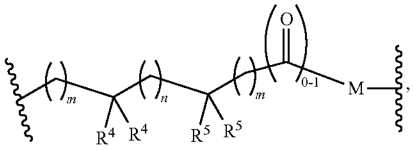

wherein either the right-hand side or left-hand side of L is attached to A.

In some embodiments, L is a covalent bond or a bivalent, saturated or unsaturated, straight or branched, optionally substituted bivalent $C_{1-30}$ (e.g., $C_{3-30}$, $C_{5-30}$, $C_{7-30}$, $C_{3-25}$, $C_{5-25}$, $C_{7-25}$, $C_{3-20}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid selected from

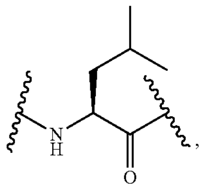
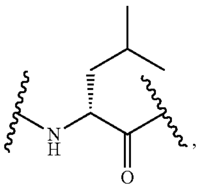
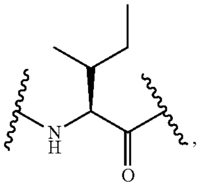
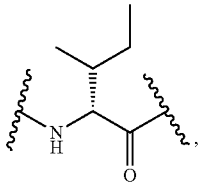

-continued

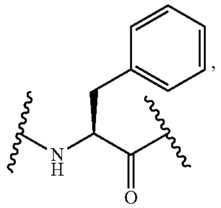
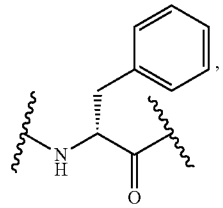
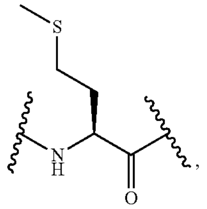
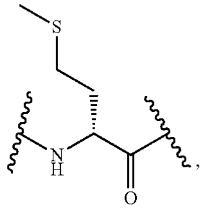
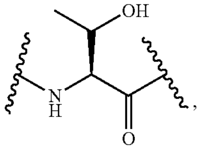
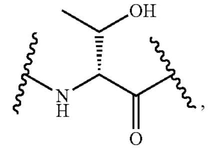
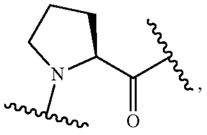
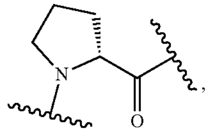
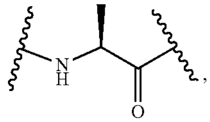
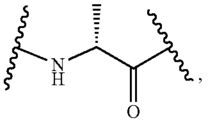
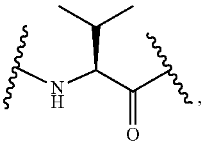
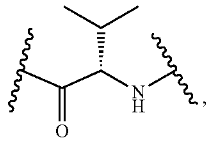
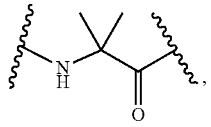
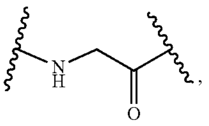
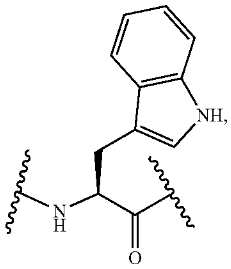
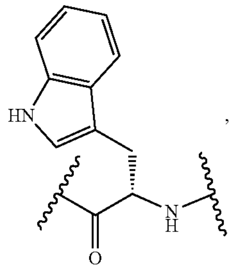
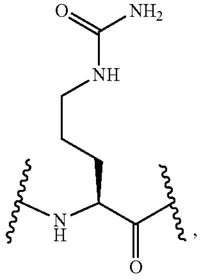

or

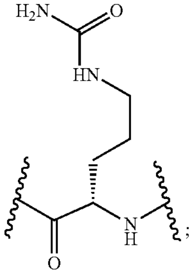

and wherein 1 methylene unit of L is optionally replaced with -M-; or

L is

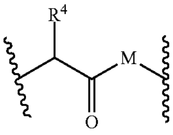
,
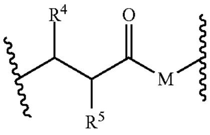
,
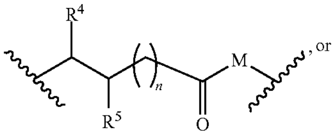
, or
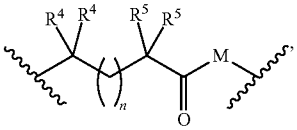
, wherein either the right-hand side or left-hand side of L is attached to A.

In some embodiments, L is a bivalent, saturated or unsaturated, straight or branched, optionally substituted bivalent $C_{1-20}$ (e.g., $C_{3-20}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, $C_{6-12}$, etc.) hydrocarbon chain, wherein 0-8 (i.e., 0, 1, 2, 3, 4, 5, 6, 7, or 8) methylene units of L are independently replaced by -Cy-, —O—, —NR—, —S—, —OC(O)—, —C(O)O—, —C(O)—, —S(O)—, —$S(O)_2$—, —C(S)—, —$NRS(O)_2$—, —$S(O)_2NR$—, —NRC(O)—, —C(O)NR—, —OC(O)NR—, —NRC(O)O—, or a naturally-occurring amino acid such as

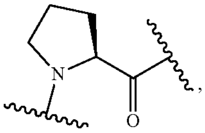
,
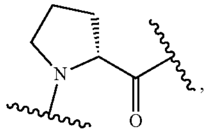
,
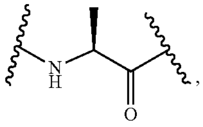
,
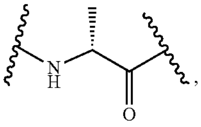
,
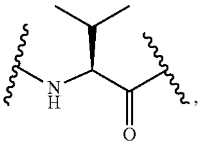
,
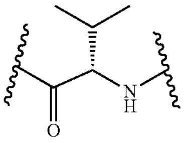
,
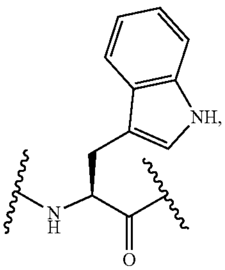
,
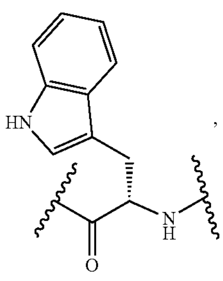
, -continued

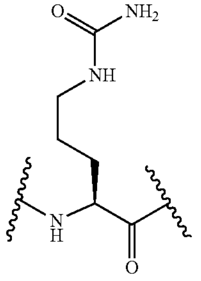
, or
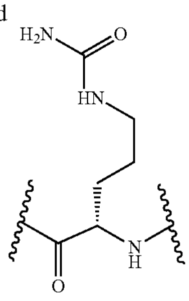
;

and wherein 1 methylene unit of L is optionally replaced with -M-. In some embodiments, L is a covalent bond or a bivalent, saturated or unsaturated, straight or branched $C_{3-16}$, $C_{5-12}$, $C_{8-16}$ or $C_{6-16}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —$S(O)_2$—, —C(S)—, —$NRS(O)_2$—, —$S(O)_2NR$—, —NRC(O)—, —C(O)NR—, —OC(O)NR—, —NRC(O)O—,

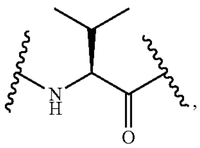
,
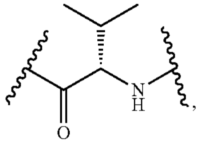
,
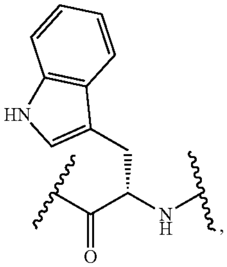
,
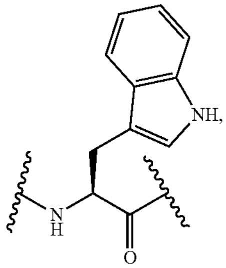

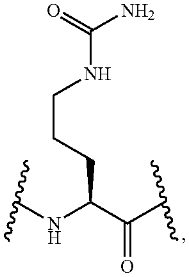
, or
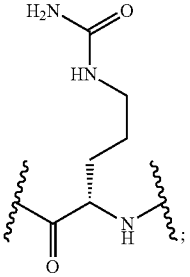
;

and 1 methylene unit of L is optionally replaced with -M-. In some embodiments, L is a bivalent, saturated, straight $C_{3-20}$, $C_{5-16}$, $C_{6-12}$, $C_{7-20}$, $C_{5-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain, wherein 0-6, 0-4, 0-3, or 0-1 methylene units of L are independently replaced by -Cy-, —O—, —NR—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, or —NRC(O)O—; and 1 methylene unit of L is optionally replaced with -M-. In some embodiments, L is a bivalent, saturated, straight $C_{3-20}$, $C_{5-16}$, $C_{6-12}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain, wherein 0-6, 0-4, 0-3, or 0-1 methylene units of L are independently replaced by —O—, —NR—, —S—, —OC(O)—, —C(O)O—, —C(O)—, —S(O)—, —$S(O)_2$—, or —C(S)—; and 1 methylene unit of L is optionally replaced with -M-.

In some embodiments, L is a bivalent, saturated $C_{3-30}$, $C_{5-25}$, $C_{6-20}$, $C_{8-20}$, $C_{10-18}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain optionally substituted with 1, 2, 3, or 4 $R^4$ groups, wherein 0-4 methylene units of L are independently replaced by —O—, —OC(O)—, —C(O)O—, or —C(O)—; and 1 methylene unit of L is optionally replaced with -M-.

In some embodiments, L is a bivalent, saturated $C_{1-25}$, $C_{5-25}$, $C_{5-20}$, $C_{7-20}$, $C_{8-18}$, $C_{6-18}$, $C_{7-17}$, $C_{8-16}$, $C_{8-15}$, $C_{8-14}$, $C_{7-13}$, or $C_{6-12}$ hydrocarbon chain optionally substituted with 1, 2, 3, or 4 groups selected from deuterium, halogen, —CN, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with 1, 2, 3, 4, 5, or 6 deuterium or halogen atoms; wherein 0-4 methylene units of L are independently replaced by —O—, —OC(O)—, —C(O)O—, or —C(O)—; and 1 methylene unit of L is optionally replaced with -M-.

In some embodiments, L comprises $(—OCH_2CH_2—)_{1-8}$ (i.e., 1-8 polyethylene glycol (PEG) units). In some embodiments, L comprises 1, 2, 3, 4, 5, 6, 7, or 8 PEG units.

In some embodiments, 0-6 units of L are independently replaced by —O—, —S—, —OC(O)—, —C(O)O—, —C(O)—, or —C(S)—; and 1 methylene unit of L is optionally replaced with -M-.

In some embodiments, L comprises

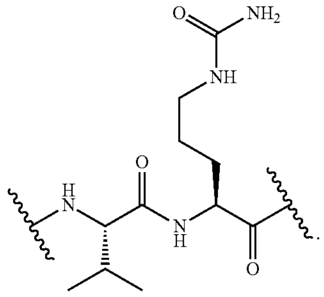 [SMILES: *N[C@H](C(=O)N[C@@H](CCCNC(N)=O)C(*)=O)C(C)C]

In some embodiments, L comprises

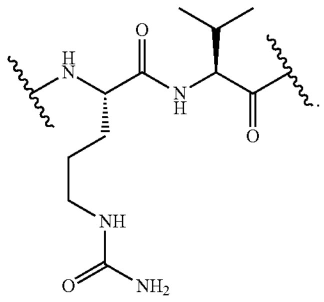 [SMILES: *N[C@@H](CCCNC(N)=O)C(=O)N[C@H](C(*)=O)C(C)C]

In some embodiments, L comprises

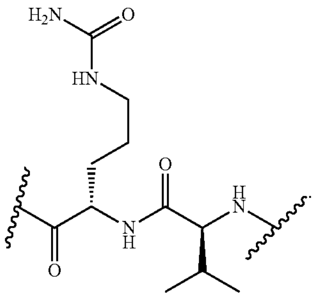 [SMILES: *N[C@H](C(=O)N[C@@H](CCCNC(N)=O)C(*)=O)C(C)C]

In some embodiments, L comprises

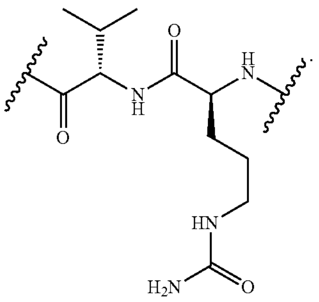 [SMILES: *N[C@@H](CCCNC(N)=O)C(=O)N[C@H](C(*)=O)C(C)C]

In some embodiments, L comprises

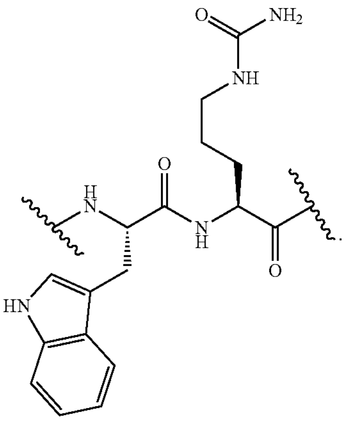 [SMILES: *N[C@@H](Cc1c[nH]c2ccccc12)C(=O)N[C@@H](CCCNC(N)=O)C(*)=O]

In some embodiments, L comprises

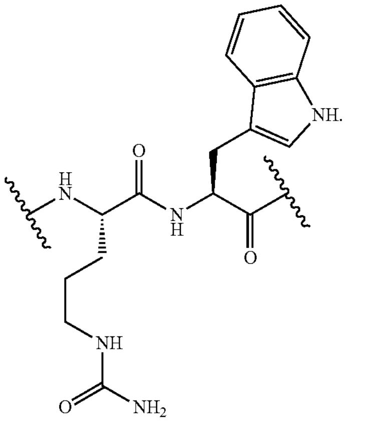 [SMILES: *N[C@@H](CCCNC(N)=O)C(=O)N[C@@H](Cc1c[nH]c2ccccc12)C(*)=O]

In some embodiments, L comprises

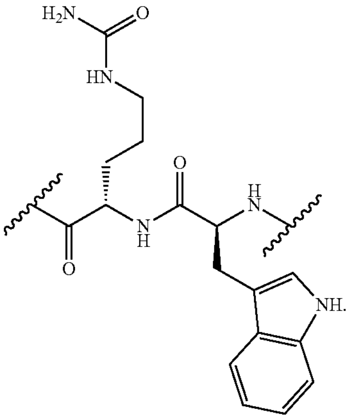 [SMILES: *N[C@@H](Cc1c[nH]c2ccccc12)C(=O)N[C@@H](CCCNC(N)=O)C(*)=O]

In some embodiments, L comprises

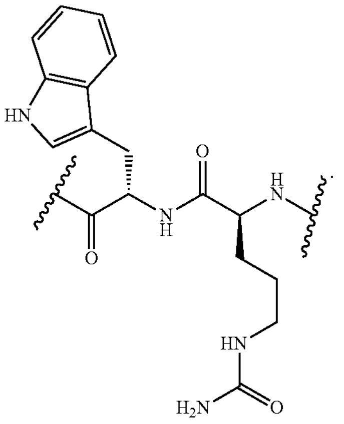 [SMILES: *N[C@@H](CCCNC(N)=O)C(=O)N[C@@H](Cc1c[nH]c2ccccc12)C(*)=O]

In some embodiments, 1 methylene unit of L is replaced with -M-.

In some embodiments, 1, 2, 3, or 4 available hydrogen atoms of L are replaced with an $R^4$ group, i.e., L is optionally substituted with 1, 2, 3, or 4 $R^4$ groups.

In some embodiments, a methylene unit of L is replaced with an amino acid. The amino acid may be naturally-occurring or non-naturally occurring. In some embodiments, the amino acid is selected from a non-polar or branched chain amino acid (BCAA). In some embodiments, the amino acid is selected from valine, isoleucine, leucine, methionine, alanine, proline, glycine, phenylalanine, tyrosine, tryptophan, histidine, asparagine, glutamine, serine threonine, lysine, arginine, histidine, aspartic acid, glutamic acid, cysteine, selenocysteine, or tyrosine. In some embodiments, the amino acid is an L-amino acid. In some embodiments, the amino acid is a D-amino acid.

As defined above and described herein, each -Cy- is independently an optionally substituted 3-6 membered bivalent saturated, partially unsaturated, or aromatic ring having 0-4 heteroatoms independently selected from nitrogen, oxygen, or sulfur.

In some embodiments, -Cy- is an optionally substituted 3-6 membered bivalent saturated ring having 0-4 heteroatoms independently selected from nitrogen, oxygen, or sulfur. In some embodiments, -Cy- is an optionally substituted 5-membered bivalent saturated, partially unsaturated, or aromatic ring having 0-4 heteroatoms independently selected from nitrogen, oxygen, or sulfur. In some embodiments, -Cy- is an optionally substituted 6-membered bivalent saturated, partially unsaturated, or aromatic ring having 0-4 heteroatoms independently selected from nitrogen, oxygen, or sulfur.

As defined above and described herein, each $R^4$ and $R^5$ is independently hydrogen, deuterium, halogen, —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, $R^4$ is hydrogen. In some embodiments, $R^4$ is deuterium. In some embodiments, $R^4$ is halogen. In some embodiments, $R^4$ is —CN. In some embodiments, $R^4$ is —OR. In some embodiments, $R^4$ is —$NR_2$. In some embodiments, $R^4$ is —SR. In some embodiments, $R^4$ is a 3-8 membered saturated or partially unsaturated monocyclic carbocyclic ring. In some embodiments, $R^4$ is phenyl. In some embodiments, $R^4$ is an 8-10 membered bicyclic aromatic carbocyclic ring. In some embodiments, $R^4$ is a 4-8 membered saturated or partially unsaturated monocyclic heterocyclic ring having 1-2 heteroatoms independently selected from nitrogen, oxygen, or sulfur. In some embodiments, $R^4$ is a 5-6 membered monocyclic heteroaromatic ring having 1-4 heteroatoms independently selected from nitrogen, oxygen, or sulfur. In some embodiments, $R^4$ is an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^4$ is a $C_{1-6}$ aliphatic group optionally substituted with 1, 2, 3, 4, 5, or 6 deuterium or halogen atoms. In some embodiments, two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, each $R^4$ is independently hydrogen, deuterium, halogen, —CN, or $C_{1-4}$ aliphatic optionally substituted with 1, 2, 3, 4, 5, or 6 deuterium or halogen atoms; or two instances of $R^4$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, at least one instance of $R^4$ is not hydrogen.

In some embodiments, $R^4$ is $C_{1-4}$ aliphatic optionally substituted with 1, 2, 3, 4, 5, or 6 deuterium or halogen atoms. In some embodiments, $R^4$ is $C_{1-4}$ alkyl optionally substituted with 1, 2, or 3 deuterium or halogen atoms. In some embodiments, $R^4$ is methyl optionally substituted with 1, 2, or 3 deuterium or halogen atoms. In some embodiments, $R^4$ is ethyl. In some embodiments, $R^4$ is n-propyl. In some embodiments, $R^4$ is isopropyl. In some embodiments, $R^4$ is n-butyl. In some embodiments, $R^4$ is isobutyl. In some embodiments, $R^4$ is tert-butyl.

In some embodiments, $R^5$ is hydrogen. In some embodiments, $R^5$ is deuterium. In some embodiments, $R^5$ is halogen. In some embodiments, $R^5$ is —CN. In some embodiments, $R^5$ is —OR. In some embodiments, $R^5$ is —$NR_2$. In some embodiments, $R^5$ is —SR. In some embodiments, $R^5$ is a 3-8 membered saturated or partially unsaturated monocyclic carbocyclic ring. In some embodiments, $R^5$ is phenyl. In some embodiments, $R^5$ is an 8-10 membered bicyclic aromatic carbocyclic ring. In some embodiments, $R^5$ is a 4-8 membered saturated or partially unsaturated monocyclic heterocyclic ring having 1-2 heteroatoms independently selected from nitrogen, oxygen, or sulfur. In some embodiments, $R^5$ is a 5-6 membered monocyclic heteroaromatic ring having 1-4 heteroatoms independently selected from nitrogen, oxygen, or sulfur. In some embodiments, $R^5$ is an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^5$ is a $C_{1-6}$ aliphatic group optionally substituted with 1, 2, 3, 4, 5, or 6 deuterium or halogen atoms. In some embodiments, two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, each $R^5$ is independently hydrogen, deuterium, halogen, —CN, or $C_{1-4}$ aliphatic optionally substituted with 1, 2, 3, 4, 5, or 6 deuterium or halogen atoms; or two instances of $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur.

In some embodiments, at least one instance of $R^5$ is not hydrogen.

In some embodiments, $R^5$ is $C_{1-4}$ aliphatic optionally substituted with 1, 2, 3, 4, 5, or 6 deuterium or halogen atoms. In some embodiments, $R^5$ is methyl optionally substituted with 1, 2, or 3 deuterium or halogen atoms. In some embodiments, $R^5$ is ethyl. In some embodiments, $R^5$ is n-propyl. In some embodiments, $R^5$ is isopropyl. In some embodiments, $R^5$ is n-butyl. In some embodiments, $R^5$ is isobutyl. In some embodiments, $R^5$ is tert-butyl.

As defined above and described herein, -M- is a self-immolative group.

In some embodiments, -M- is an acetal, an o-benzylalcohol, a p-benzylalcohol, a styryl group, a coumarin, or a group that self-immolates via a cyclization reaction. In some embodiments, -M- is selected from a disulfide, hydrazone, acetal self-immolative group, carboxyacetal self-immolative group, carboxy(methylacetal) self-immolative group, para-hydroxybenzyl self-immolative group, para-hydroxybenzyl carbonyl self-immolative group, flipped ester self-immolative group, trimethyl lock self-immolative group, or 2-hydroxyphenyl carbamate (2-HPC) self-immolative group.

In some embodiments, -M- is selected from one of the following:

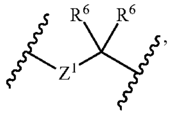
,
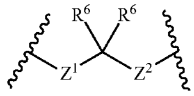
,
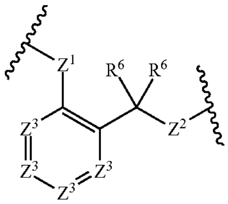
,
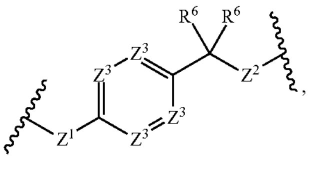
,

-continued

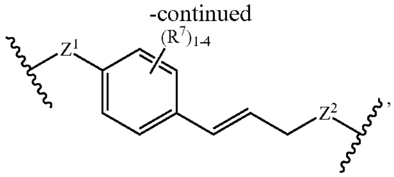

,

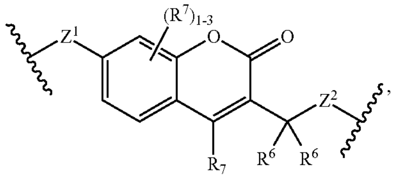

,

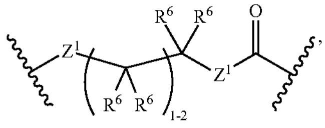

,

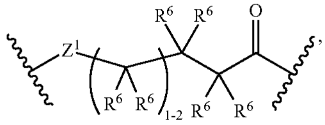

,

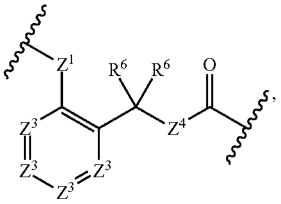

, or

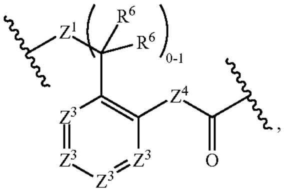

, wherein each $R^6$ is independently selected from hydrogen, deuterium, $C_{1-10}$ aliphatic, halogen, or —CN;

each $R^7$ is independently selected from hydrogen, deuterium, halogen, —CN, —OR, —$NR_2$, —$NO_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ is independently selected from —O—, —NR—, or —S—;

each $Z^2$ is independently selected from —O—, —NR—, —S—, —OC(O)—, —NRC(O)O—, or —OC(O)NR—;

each $Z^3$ is independently selected from =N— or =C($R^7$)—; and each $Z^4$ is independently selected from —O—, —NR—, —S—, —C($R^6$)$_2$—, or a covalent bond.

As defined generally above and described herein, each $R^6$ is independently selected from hydrogen, deuterium, $C_{1-10}$ aliphatic, halogen, or —CN. In some embodiments, $R^6$ is hydrogen. In some embodiments, $R^6$ is deuterium. In some embodiments, $R^6$ is $C_{1-10}$ aliphatic. In some embodiments, $R^6$ is halogen. In some embodiments, $R^6$ is —CN.

In some embodiments, $R^6$ is hydrogen, $C_{1-5}$ alkyl, halogen, or —CN. In some embodiments, $R^6$ is hydrogen or $C_{1-3}$ alkyl. In some embodiments, $R^6$ is hydrogen or methyl.

In some embodiments, each instance of $R^6$ in the above formulae is the same. In some embodiments, each $R^6$ is different. In some embodiments, one $R^6$ is hydrogen. In some embodiments, one $R^6$ is $C_{1-5}$ aliphatic. In some embodiments, each $R^6$ is hydrogen. In some embodiments, each $R^6$ is $C_{1-5}$ aliphatic.

As defined generally above and described herein, each $R^7$ is independently selected from hydrogen, deuterium, halogen, —CN, —OR, —$NR_2$, —$NO_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic group is optionally substituted with 1, 2, 3, 4, 5, or 6 deuterium or halogen atoms.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —$NR_2$. In some embodiments, $R^7$ is —$NO_2$. In some embodiments, $R^7$ is —SR. In some embodiments, $R^7$ is a 3-8 membered saturated or partially unsaturated monocyclic carbocyclic ring. In some embodiments, $R^7$ is phenyl. In some embodiments, $R^7$ is an 8-10 membered bicyclic aromatic carbocyclic ring. In some embodiments, $R^7$ is a 4-8 membered saturated or partially unsaturated monocyclic heterocyclic ring having 1-2 heteroatoms independently selected from nitrogen, oxygen, or sulfur. In some embodiments, $R^7$ is a 5-6 membered monocyclic heteroaromatic ring having 1-4 heteroatoms independently selected from nitrogen, oxygen, or sulfur. In some embodiments, $R^7$ is or an 8-10 membered bicyclic heteroaromatic ring having 1-5 heteroatoms independently selected from nitrogen, oxygen, or sulfur. In some embodiments, $R^7$ is or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^7$ is a $C_{1-6}$ aliphatic group optionally substituted with 1, 2, 3, 4, 5, or 6 deuterium or halogen atoms.

In some embodiments, $R^7$ is hydrogen, deuterium, halogen, —CN, —OR, —$NR_2$, —$NO_2$, —SR, a 3-6 membered saturated or partially unsaturated monocyclic carbocyclic ring, phenyl, a 4-6 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or a $C_{1-6}$ aliphatic group optionally substituted with —CN, —OR, —$NR_2$, —SR, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-6}$ aliphatic group is optionally substituted with 1, 2, 3, 4, 5, or 6 deuterium or halogen atoms. In some embodiments, $R^7$ is hydrogen, deuterium, halogen, —CN, a 3-6 membered saturated or partially unsaturated monocyclic carbocyclic ring, phenyl, a 5-6 membered monocyclic heteroaromatic ring having 1-4 heteroatoms independently selected from nitrogen, oxygen, or sulfur, or a $C_{1-4}$ alkyl group optionally substituted with —CN, a 3-6 membered saturated or partially unsaturated monocyclic carbocyclic ring, phenyl, or a 5-6 membered monocyclic heteroaromatic ring having 1-4 heteroatoms independently selected from nitrogen, oxygen, or sulfur, or the $C_{1-4}$ alkyl group is optionally substituted with 1, 2, 3, 4, 5, or 6 deuterium or halogen atoms. In some embodiments, $R^7$ is hydrogen, halogen, —CN, —OR, or $C_{1-4}$ alkyl.

In some embodiments, R is hydrogen or $C_{1-4}$ alkyl.

As defined generally above and described herein, each $Z^1$ is independently selected from —O—, —NR—, or —S—. In some embodiments, $Z^1$ is —O—. In some embodiments, $Z^1$ is —NR—. In some embodiments, $Z^1$ is —S. In some embodiments, $Z^1$ is —NH— or —NMe-.

As defined generally above and described herein, each $Z^2$ is independently selected from —O—, —NR—, —S—, —OC(O)—, —NRC(O)O—, or —OC(O)NR—.

In some embodiments, $Z^2$ is —O—. In some embodiments, $Z^2$ is —NR—. In some embodiments, $Z^2$ is —S—. In some embodiments, $Z^2$ is —OC(O)—. In some embodiments, $Z^2$ is —NRC(O)O—. In some embodiments, $Z^2$ is —OC(O)NR—.

In some embodiments, each $Z^2$ is independently selected from —O—, —NH—, —NMe-, —S—, —OC(O)—, —NHC(O)O—, —NMeC(O)O—, —OC(O)NH—, or —OC(O)NMe-.

In some embodiments, $Z^2$ is covalently bound to A. In some embodiments, $Z^2$ is —O— or —OC(O)O—.

In some embodiments, $Z^1$ is —O— and $Z^2$ is —O— or —OC(O)O—.

As defined generally above and described herein, each $Z^3$ is independently selected from =N— or =C($R^7$)—. In some embodiments, $Z^3$ is =N—. In some embodiments, $Z^3$ is =C($R^7$)—.

As defined generally above and described herein, each $Z^4$ is independently selected from —O—, —NR—, —S—, —C($R^6$)$_2$—, or a covalent bond. In some embodiments, $Z^4$ is —O—. In some embodiments, $Z^4$ is —NR—. In some embodiments, $Z^4$ is —S—. In some embodiments, $Z^4$ is —C($R^6$)$_2$—. In some embodiments, $Z^4$ is a covalent bond.

In some embodiments, -M- is selected from one of the following:

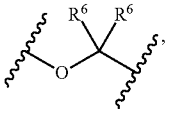

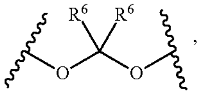

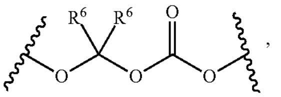

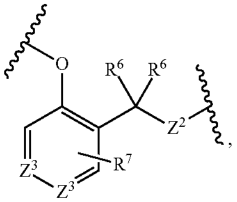

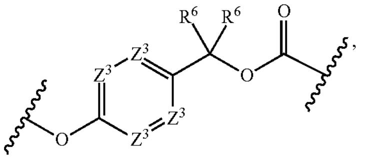

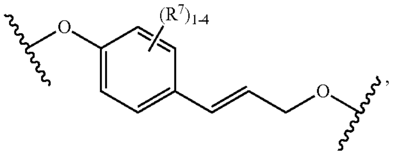

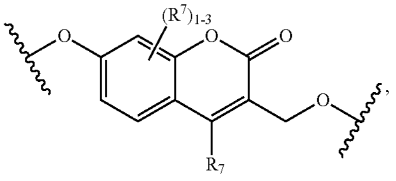

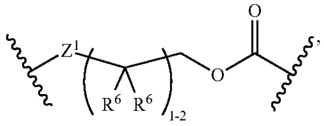

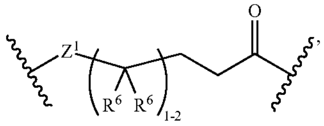

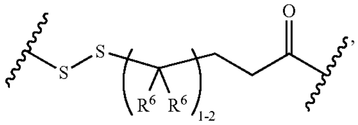

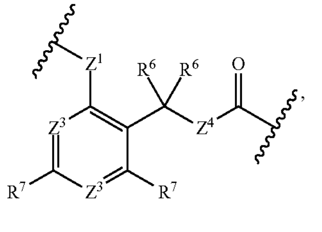

or

-continued
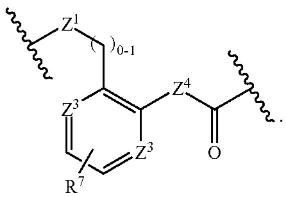
In some embodiments, -M- is selected from
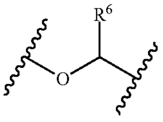, 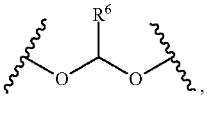, 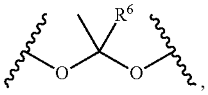, 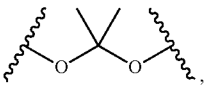, 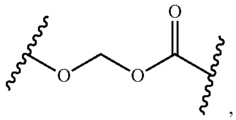, 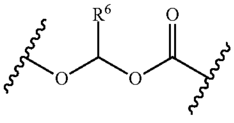, 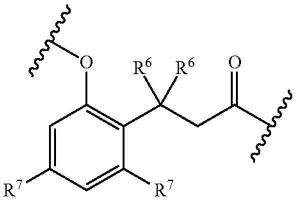, 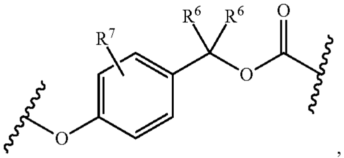, 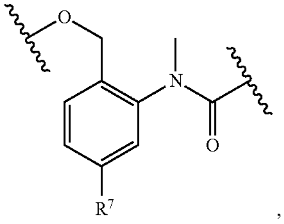, 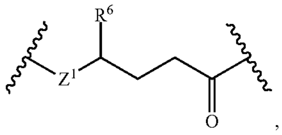, 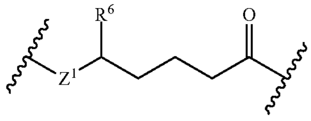, 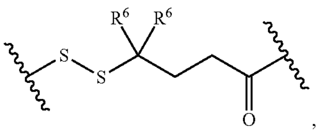, or
-continued
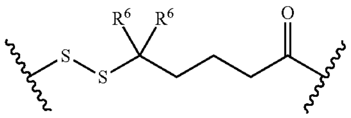.
In some embodiments, -M- is selected from
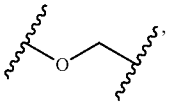, 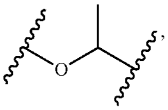, 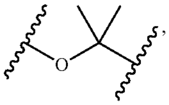, 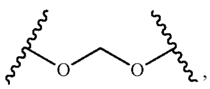, 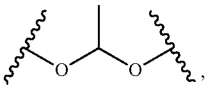, 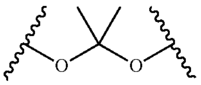, 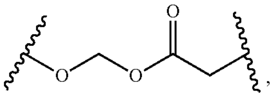, 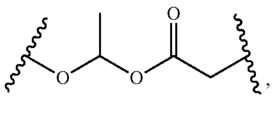, 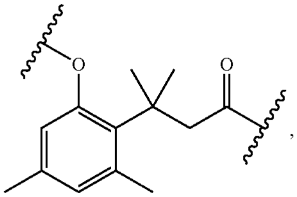, 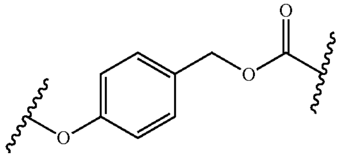, 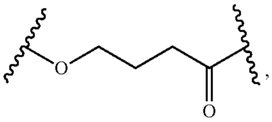, 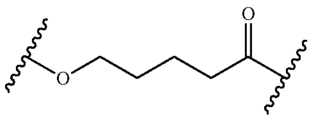, 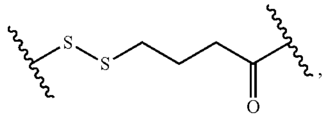, or 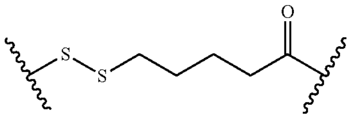,
In some embodiments, -M- is selected from
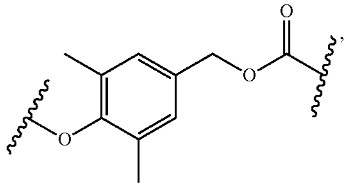, -continued

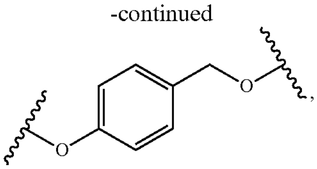,

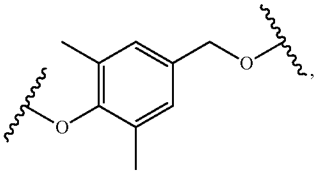,

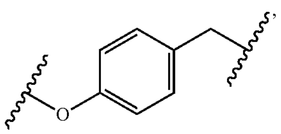, or

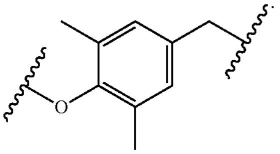.

As defined above and described herein, n is 0-18.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 1-16, 1-14, 1-12, 1-10, 1-8, 1-6, 1-3, 2-16, 2-14, 2-12, 2-10, 2-8, 2-6, 3-12, 3-8, 3-6, 4-10, 4-8, 4-6, 5-10, 5-8, 5-6, 6-18, 6-10, 6-8, 8-12, 5-18, 5-13, 8-18, 8-17, 8-16, 8-15, 8-16, or 6-16.

As defined above and described herein, each m is independently 0-6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, each m is independently 0, 1, or 2. In some embodiments, each m is independently 1, 2, 3, or 4.

As defined above and described herein, A is a COX-2 inhibitor. In some embodiments, A is celecoxib. In some embodiments, A is

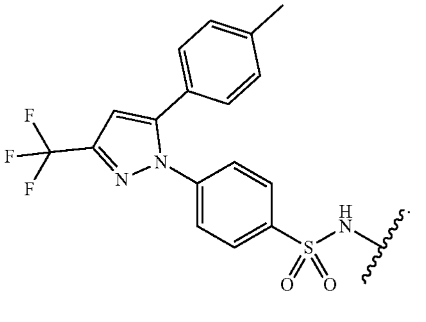 [SMILES: *NS(=O)(=O)c1ccc(-n2nc(C(F)(F)F)cc2-c2ccc(C)cc2)cc1].

As used herein, depiction of brackets around a therapeutic agent, A,

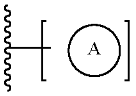

means that the

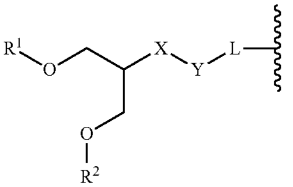

moiety is covalently attached to A at any available modifiable nitrogen, oxygen, or sulfur atom. For purposes of clarity and by way of example, such available modifiable nitrogen, oxygen, or sulfur atoms in acetaminophen are depicted below, wherein each wavy bond defines the point of attachment to said

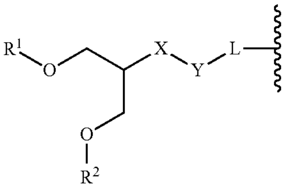

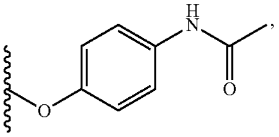, 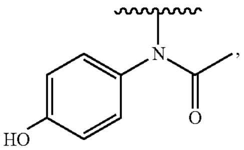, or

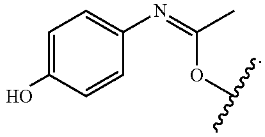.

In certain embodiments, the present invention provides a lipid prodrug of Formula II:

II

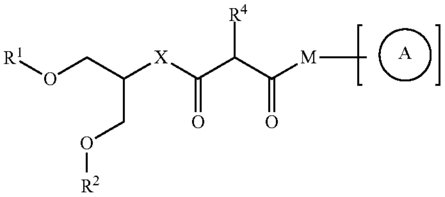

or a pharmaceutically acceptable salt thereof, wherein each of $R^1$, $R^2$, $R^4$, X, M and A is as defined above and described in embodiments herein, both singly and in combination.

In certain embodiments, the present invention provides a lipid prodrug of Formula III:

III

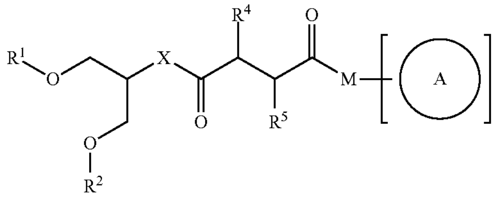

or a pharmaceutically acceptable salt thereof, wherein each of $R^1$, $R^2$, $R^4$, $R^5$, X, M and A is as defined above and described in embodiments herein, both singly and in combination.

In certain embodiments, the present invention provides a lipid prodrug of Formula IV:

IV

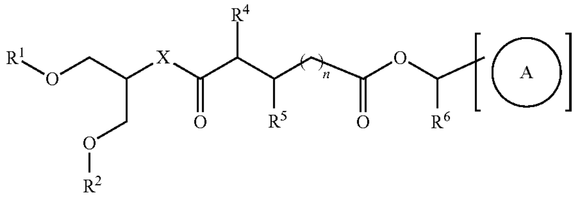

or a pharmaceutically acceptable salt thereof, wherein each of $R^1$, $R^2$, $R^4$, $R^5$, $R^6$, X, and A is as defined above and described in embodiments herein, both singly and in combination.

In some embodiments, the present invention provides a lipid prodrug of Formula VI:

VI

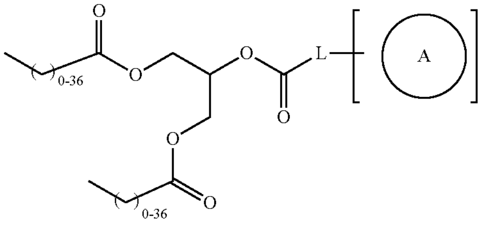

or a pharmaceutically acceptable salt thereof, wherein each of L, $R^1$, $R^2$, R, X, and A is as defined above and described in embodiments herein, both singly and in combination.

In some embodiments, the present invention provides a lipid prodrug of Formula VII-a or VII-b:

VII-a

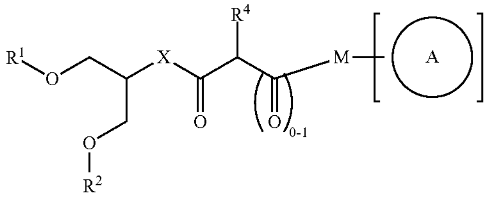

VII-b

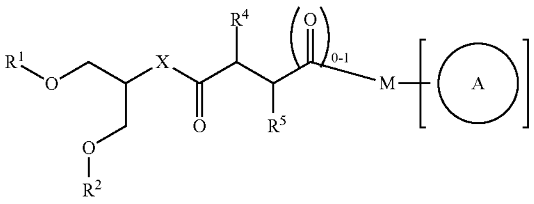

or a pharmaceutically acceptable salt thereof, wherein each of $R^1$, $R^2$, $R^4$, $R^5$, X, M, and A is as defined above and described in embodiments herein, both singly and in combination.

In some embodiments, the present invention provides a lipid prodrug of Formula VIII-a or VIII-b:

VIII-a

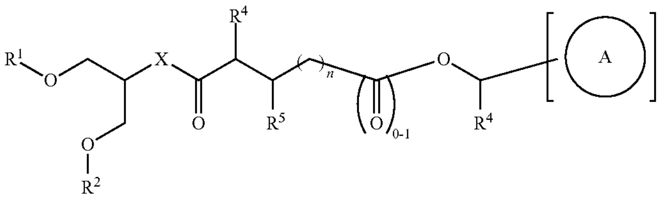

-continued

VIII-b

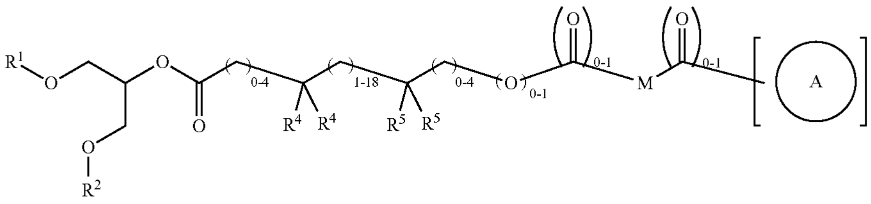

or a pharmaceutically acceptable salt thereof, wherein each of $R^1$, $R^2$, $R^4$, $R^5$, X, n, and A is as defined above and described in embodiments herein, both singly and in combination.

In some embodiments, the present invention provides a lipid prodrug of Formula IX-a, IX-b, IX-c, or IX-d:

IX-a

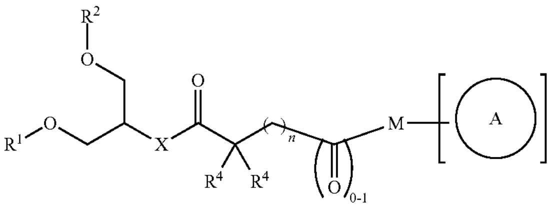

IX-b

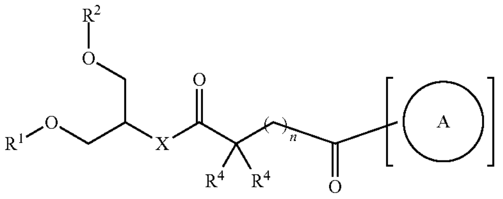

-continued

IX-c

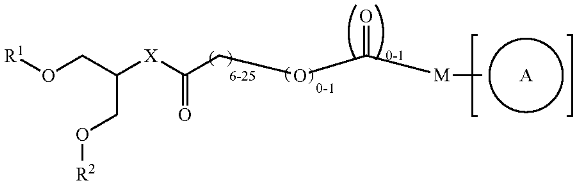

IX-d

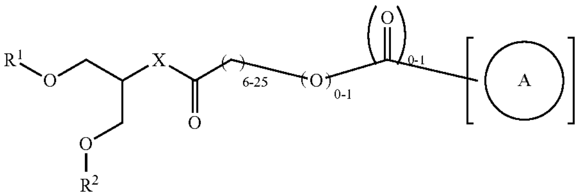

or a pharmaceutically acceptable salt thereof, wherein each variable is as defined above and described in embodiments herein, both singly and in combination.

In some embodiments, the present invention provides a lipid prodrug of Formula X-a, X-b, X-c, X-d, X-e, X-f, X-g, or X-h:

X-a

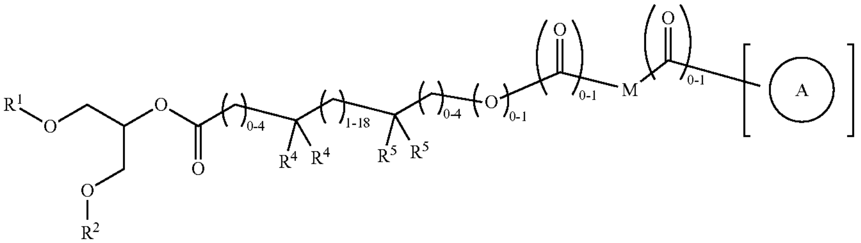

X-b

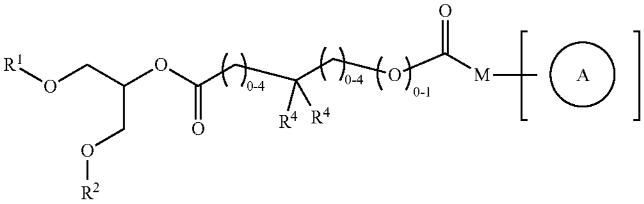

-continued
X-c
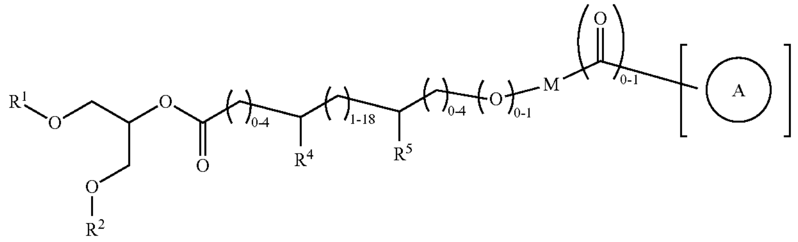
X-d
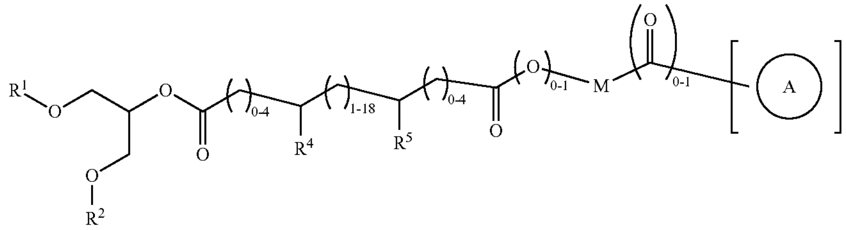
X-e
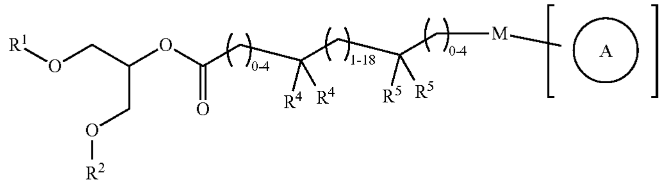
X-f
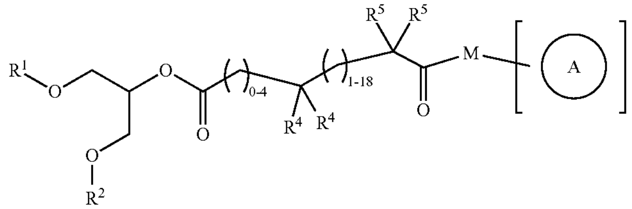
X-g
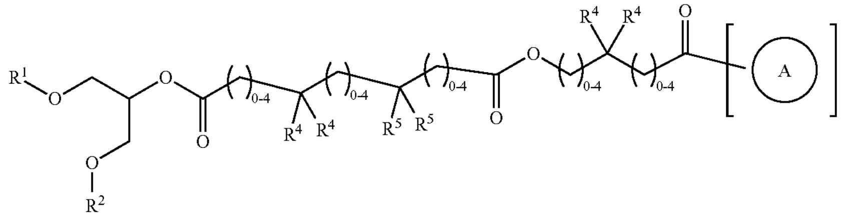
X-h
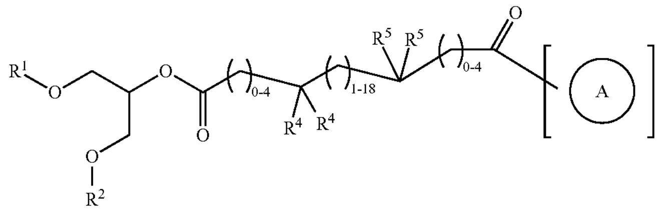

or a pharmaceutically acceptable salt thereof, wherein each variable is as defined above and described in embodiments herein, both singly and in combination.

In some embodiments, the present invention provides a lipid prodrug of Formula XI-a or XI-b:

XI-a

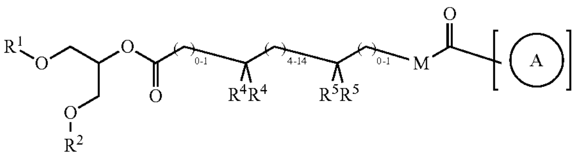

-continued

XI-b

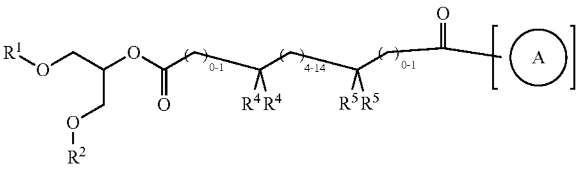

or a pharmaceutically acceptable salt thereof, wherein each variable is as defined above and described in embodiments herein, both singly and in combination.

In some embodiments, the present invention provides a lipid prodrug of Formula XII-a, XII-b, XII-c, XII-d, XII-e, XII-f, or XII-g:

XII-a

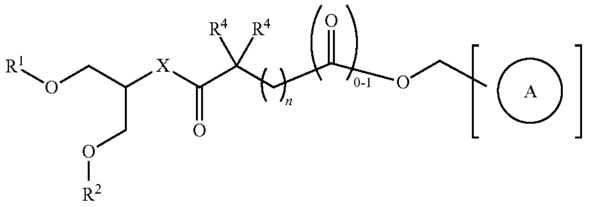

XII-b

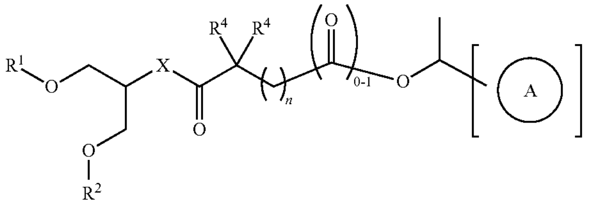

XII-c

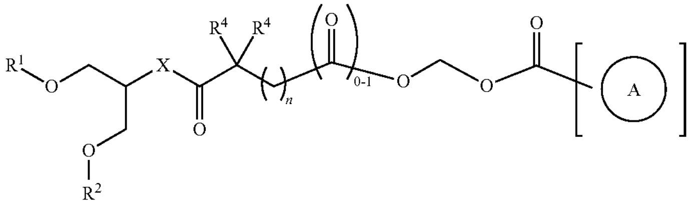

XII-d

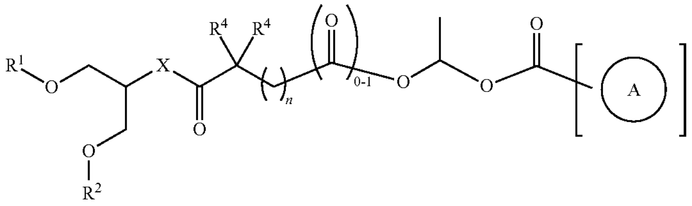

XII-e

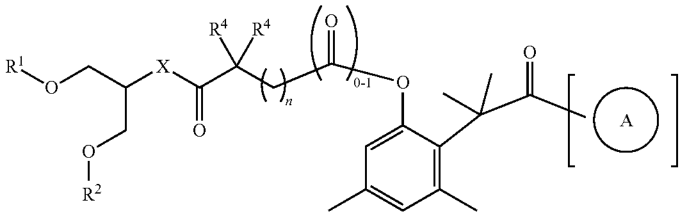

-continued
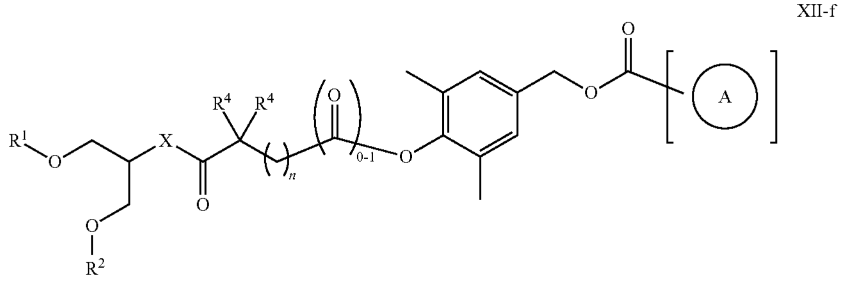
XII-f
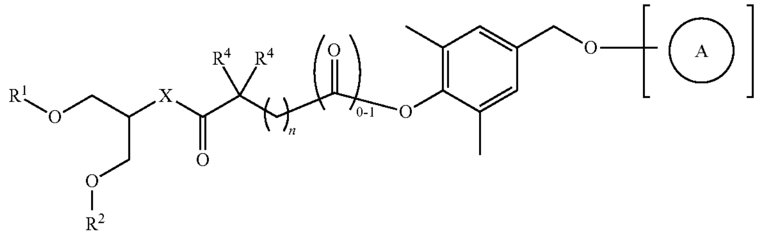
XII-g
or a pharmaceutically acceptable salt thereof, wherein each variable is as defined above and described in embodiments herein, both singly and in combination.
In some embodiments, the present invention provides a lipid prodrug of Formula XIII-a, XIII-b, XIII-c, XIII-d, XIII-e, XIII-f, or XIII-g:
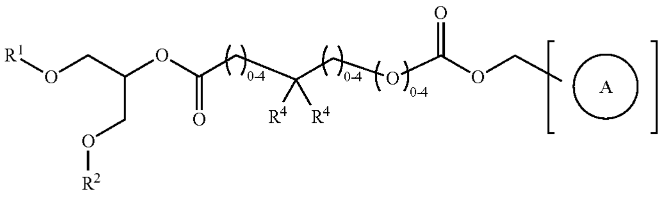
XIII-a
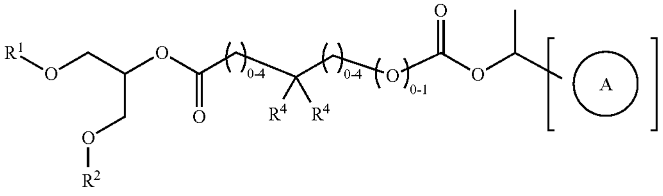
XIII-b
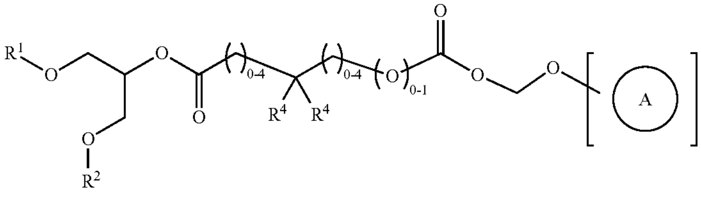
XIII-c
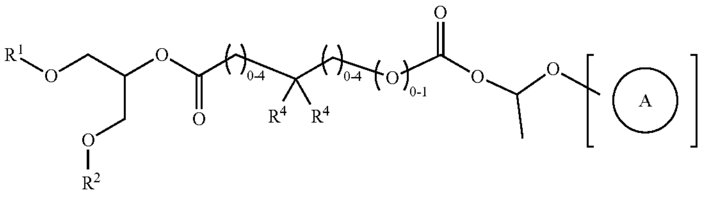
XIII-d -continued XIII-e

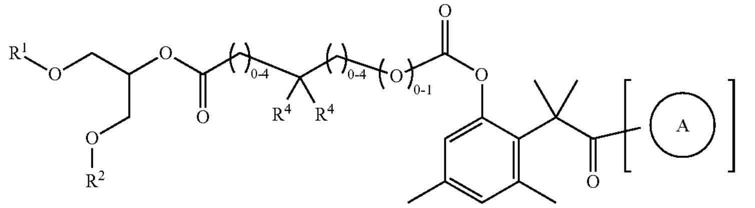

XIII-f

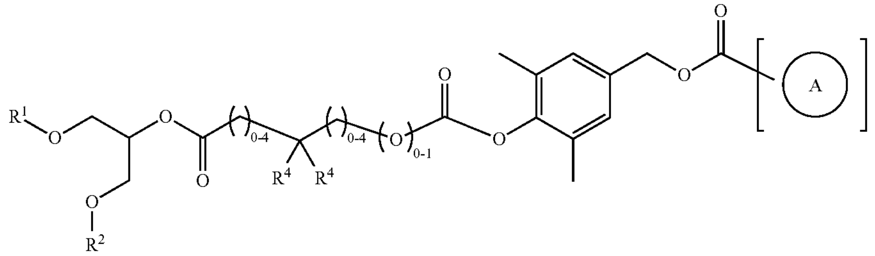

XIII-g

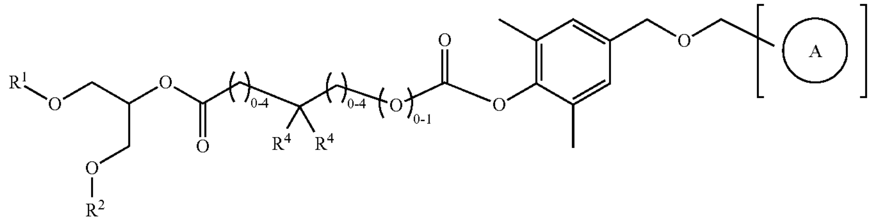

or a pharmaceutically acceptable salt thereof, wherein each variable is as defined above and described in embodiments herein, both singly and in combination.

In the above formulae, when a range of numbers, such as 0-4 or 1-18, is disclosed, individual integers within the range are also specifically disclosed. Thus, the above range of 0-4 includes 0, 1, 2, 3, and 4. The range 1-18 includes 1, 2, 3, 4, 5, 6, 7, 8, 9, 10, 11, 12, 13, 14, 15, 16, 17, and 18 as well as ranges in between such as 6-18 and 8-18. The range 0-1 includes 0 and 1, i.e. the group is optionally present. Where more than one range is disclosed in a formula, each range is independently and optionally selected from the disclosed range. For example, in Formula X-c above, each 0-4 and 0-1 range is varied independently of the others.

In some embodiments, the lipid prodrug is Compound I-1:

Lipids, including Fatty Acids, Phospholipids, Lipid-Processing Mimetics, and Mixtures Thereof for Use in Disclosed Lipid Prodrugs Lipid prodrugs according to the present disclosure mimic the lipid-processing that takes place in the human body.

A variety of lipids are suitable for use in lipid prodrugs of the present disclosure. In some embodiments, the lipid prodrug comprises a fatty acid, phosphatide, phospholipid, or analogue thereof (e.g. phosphatidylcholine, lecithin, phosphatidylethanolamine, cephalin, or phosphatidylserine or analogue or portion thereof, such as a partially hydrolyzed portion thereof), or other lipid-processing mimetic (e.g., a group cleaved by lipases, other digestive enzymes, or other mechanisms in the GI tract that enables the lipid prodrug to mimic dietary lipid processing). In some embodiments, the lipid prodrug comprises a fatty acid, phosphatide, phospho-

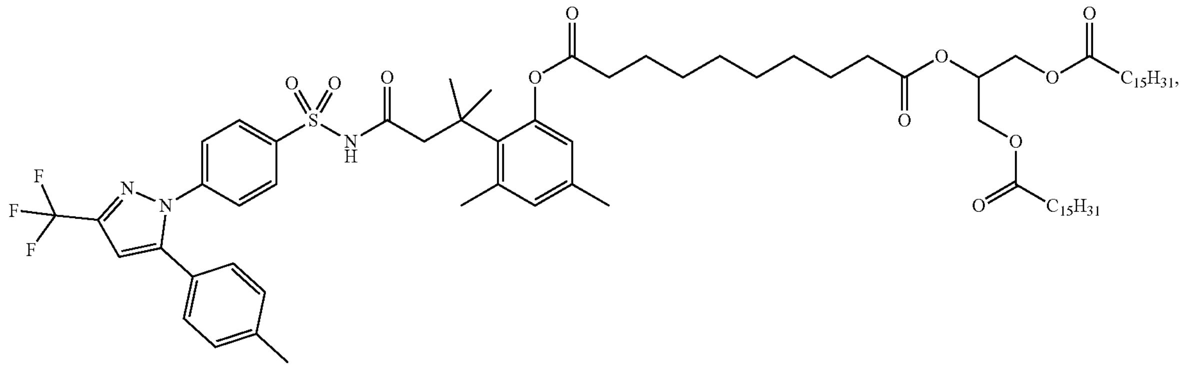

or a pharmaceutically acceptable salt thereof.

lipid, or analogue thereof at the $R^1$ or $R^2$ position in the formulae depicted above and herein. In some embodiments, the fatty acid is a short-chain, medium-chain, or long-chain fatty acid. In some embodiments, the fatty acid is a saturated fatty acid. In some embodiments, the fatty acid is an unsaturated fatty acid. In some embodiments, the fatty acid is a monounsaturated fatty acid. In some embodiments, the fatty acid is a polyunsaturated fatty acid, such as an ω-3 (omega-3) or ω-6 (omega-6) fatty acid. In some embodiments, the lipid, e.g., fatty acid, has a $C_2$-$C_{60}$ chain. In some embodiments, the lipid, e.g., fatty acid, has a $C_2$-$C_{28}$ chain. In some embodiments, the lipid, e.g., fatty acid, has a $C_2$-$C_{40}$ chain. In some embodiments, the lipid, e.g., fatty acid, has a $C_2$-$C_{12}$ or $C_4$-$C_{12}$ chain. In some embodiments, the lipid, e.g., fatty acid, has a $C_4$-$C_{40}$ chain. In some embodiments, the lipid, e.g., fatty acid, has a $C_4$-$C_{40}$, $C_2$-$C_{38}$, $C_2$-$C_{36}$, $C_2$-$C_{34}$, $C_2$-$C_{32}$, $C_2$-$C_{30}$, $C_4$-$C_{30}$, $C_2$-$C_{28}$, $C_4$-$C_{28}$, $C_2$-$C_{26}$, $C_4$-$C_{26}$, $C_2$-$C_{24}$, $C_4$-$C_{24}$, $C_6$-$C_{24}$, $C_8$-$C_{24}$, $C_{10}$-$C_{24}$, $C_2$-$C_{22}$, $C_4$-$C_{22}$, $C_6$-$C_{22}$, $C_8$-$C_{22}$, $C_{10}$-$C_{22}$, $C_2$-$C_{20}$, $C_4$-$C_{20}$, $C_6$-$C_{20}$, $C_8$-$C_{20}$, $C_{10}$-$C_{20}$, $C_2$-$C_{18}$, $C_4$-$C_{18}$, $C_6$-$C_{18}$, $C_8$-$C_{18}$, $C_{10}$-$C_{18}$, $C_{12}$-$C_{18}$, $C_{14}$-$C_{18}$, $C_{16}$-$C_{18}$, $C_2$-$C_{16}$, $C_4$-$C_{16}$, $C_6$-$C_{16}$, $C_8$-$C_{16}$, $C_{10}$-$C_{16}$, $C_{12}$-$C_{16}$, $C_{14}$-$C_{16}$, $C_2$-$C_{15}$, $C_4$-$C_{15}$, $C_6$-$C_{15}$, $C_8$-$C_{15}$, $C_9$-$C_{15}$, $C_{10}$-$C_{15}$, $C_{11}$-$C_{15}$, $C_{12}$-$C_{15}$, $C_{13}$-$C_{15}$, $C_2$-$C_{14}$, $C_4$-$C_{14}$, $C_6$-$C_{14}$, $C_8$-$C_{14}$, $C_9$-$C_{14}$, $C_{10}$-$C_{14}$, $C_{11}$-$C_{14}$, $C_{12}$-$C_{14}$, $C_2$-$C_{13}$, $C_4$-$C_{13}$, $C_6$-$C_{13}$, $C_7$-$C_{13}$, $C_8$-$C_{13}$, $C_9$-$C_{13}$, $C_{10}$-$C_{13}$, $C_{10}$-$C_{13}$, $C_{11}$-$C_{13}$, $C_2$-$C_{12}$, $C_4$-$C_{12}$, $C_6$-$C_{12}$, $C_7$-$C_{12}$, $C_8$-$C_{12}$, $C_9$-$C_{12}$, $C_{10}$-$C_{12}$, $C_2$-$C_{11}$, $C_4$-$C_{11}$, $C_6$-$C_{11}$, $C_7$-$C_{11}$, $C_8$-$C_{11}$, $C_9$-$C_{11}$, $C_2$-$C_{10}$, $C_4$-$C_{10}$, $C_2$-$C_9$, $C_4$-$C_9$, $C_2$-$C_8$, $C_4$-$C_8$, $C_2$-$C_7$, $C_4$-$C_7$, $C_2$-$C_6$, or $C_4$-$C_6$, chain. In some embodiments, the lipid, e.g., fatty acid, has a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, $C_{50}$, $C_{51}$, $C_{52}$, $C_{53}$, $C_{54}$, $C_{55}$, $C_{56}$, $C_{57}$, $C_{58}$, $C_{59}$, or $C_{60}$ chain. In some embodiments, the lipid prodrug comprises two fatty acids, each of which is independently selected from a fatty acid having a chain with any one of the foregoing ranges or numbers of carbon atoms. In some embodiments, one of the fatty acids is independently a fatty acid with a $C_6$-$C_{21}$ chain and one is independently a fatty acid with a $C_{12}$-$C_{36}$ chain. In some embodiments, each fatty acid independently has a chain of 11, 12, 13, 14, 15, 16, or 17 carbon atoms.

In some embodiments, the lipid prodrug comprises two lipids. In some embodiments, the two lipids, e.g. fatty acids, taken together have 6-80 carbon atoms (an equivalent carbon number (ECN) of 6-80). In some embodiments, the lipids, e.g., fatty acids, have an ECN of 6-80, 8-80, 10-80, 12-80, 14-80, 16-80, 18-80, 20-80, 22-80, 24-80, 26-80, 28-80, 30-80, 4-76, 6-76, 8-76, 10-76, 12-76, 14-76, 16-76, 18-76, 20-76, 22-76, 24-76, 26-76, 28-76, 30-76, 6-72, 8-72, 10-72, 12-72, 14-72, 16-72, 18-72, 20-72, 22-72, 24-72, 26-72, 28-72, 30-72, 6-68, 8-68, 10-68, 12-68, 14-68, 16-68, 18-68, 20-68, 22-68, 24-68, 26-68, 28-68, 30-68, 6-64, 8-64, 10-64, 12-64, 14-64, 16-64, 18-64, 20-64, 22-64, 24-64, 26-64, 28-64, 30-64, 6-60, 8-60, 10-60, 12-56, 14-56, 16-56, 18-56, 20-56, 22-56, 24-56, 26-56, 28-56, 30-56, 6-52, 8-52, 10-52, 12-52, 14-52, 16-52, 18-52, 20-52, 22-52, 24-52, 26-52, 28-52, 30-52, 6-48, 8-48, 10-48, 12-48, 14-48, 16-48, 18-48, 20-48, 22-48, 24-48, 26-48, 28-48, 30-48, 6-44, 8-44, 10-44, 12-44, 14-44, 16-44, 18-44, 20-44, 22-44, 24-44, 26-44, 28-44, 30-44, 6-40, 8-40, 10-40, 12-40, 14-40, 16-40, 18-40, 20-40, 22-40, 24-40, 26-40, 28-40, 30-40, 6-36, 8-36, 10-36, 12-36, 14-36, 16-36, 18-36, 20-36, 22-36, 24-36, 26-36, 28-36, 30-36, 6-32, 8-32, 10-32, 12-32, 14-32, 16-32, 18-32, 20-32, 22-32, 24-32, 26-32, 28-32, or 30-32.

Suitable fatty acids include saturated straight-chain fatty acids, saturated branched fatty acids, unsaturated fatty acids, hydroxy fatty acids, and polycarboxylic acids. In some embodiments, such fatty acids have up to 32 carbon atoms.

Examples of useful saturated straight-chain fatty acids include those having an even number of carbon atoms, such as butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid, and heptacosanoic acid.

Examples of suitable saturated branched fatty acids include isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, α-ethyl-hexanoic acid, α-hexyldecanoic acid, α-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.). Suitable saturated odd-carbon branched fatty acids include anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid, and 26-methyloctacosanoic acid.

Examples of suitable unsaturated fatty acids include 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8,11,14-eicosatetraenoic acid, 5,8,11,14,17-eicosapentaenoic acid, 7,10,13,16,19-docosapentaenoic acid, 4,7,10,13,16,19-docosahexaenoic acid, and the like.

Examples of suitable hydroxy fatty acids include α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10, 12-octadecadienic acid, kamolenic acid, ipurolic acid, 9,10-dihydroxystearic acid, 12-hydroxystearic acid and the like.

Examples of suitable polycarboxylic acids include oxalic acid, malonic acid, succinic acid, glutaric acid, adipic acid, pimelic acid, suberic acid, azelaic acid, sebacic acid, D,L-malic acid, and the like.

In some embodiments, each fatty acid is independently selected from Propionic acid, Butyric acid, Valeric acid, Caproic acid, Enanthic acid, Caprylic acid, Pelargonic acid, Capric acid, Undecylic acid, Lauric acid, Tridecylic acid, Myristic acid, Pentadecylic acid, Palmitic acid, Margaric acid, Stearic acid, Nonadecylic acid, arachidic acid, Heneicosylic acid, Behenic acid, Tricosylic acid, Lignoceric acid, Pentacosylic acid, Cerotic acid, Heptacosylic acid, Montanic acid, Nonacosylic acid, Melissic acid, Henatriacontylic acid, Lacceroic acid, Psyllic acid, geddic acid, ceroplastic acid, hexatriacontylic acid, heptatriacontanoic acid, or octatriacontanoic acid.

In some embodiments, each fatty acid is independently selected from α-linolenic acid, stearidonic acid, eicosapentaenoic acid, docosahexaenoic acid, linoleic acid, gamma-linoleic acid, dihomo-gamma-linoleic acid, arachidonic acid, docosatetraenoic acid, palmitoleic acid, vaccenic acid, paullinic acid, oleic acid, elaidic acid, gondoic acid, eurcic acid, nervonic acid, mead acid, adrenic acid, bosseopentaenoic acid, ozubondo acid, sardine acid, herring acid, docosahexaenoic acid, or tetracosanolpentaenoic acid, or another monounsaturated or polyunsaturated fatty acid.

In some embodiments, one or both of the fatty acids is an essential fatty acid. In view of the beneficial health effects of certain essential fatty acids, the therapeutic benefits of disclosed lipid prodrugs may be increased by including such fatty acids in the lipid prodrug. In some embodiments, the essential fatty acid is an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, the 20:4n-3 acid, eicosapentaenoic acid, docosapentaenoic n-3 acid, or docosahexaenoic acid.

In some embodiments, each fatty acid is independently selected from all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid, or lipoic acid. In other embodiments, the fatty acid is selected from eicosapentaenoic acid, docosahexaenoic acid, or lipoic acid. Other examples of fatty acids include all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid). In some embodiments, the fatty acid is a medium-chain fatty acid such as lipoic acid.

Fatty acid chains differ greatly in the length of their chains and may be categorized according to chain length, e.g. as short to very long.

Short-chain fatty acids (SCFA) are fatty acids with chains of about five or less carbons (e.g. butyric acid). In some embodiments, each of the fatty acids is independently a SCFA. In some embodiments, one of the fatty acids is independently a SCFA.

Medium-chain fatty acids (MCFA) include fatty acids with chains of about 6-12 carbons, which can form medium-chain triglycerides. In some embodiments, each of the fatty acids is independently a MCFA. In some embodiments, one of the fatty acids is independently a MCFA.

Long-chain fatty acids (LCFA) include fatty acids with chains of 13-21 carbons. In some embodiments, each of the fatty acids is independently a LCFA. In some embodiments, one of the fatty acids is independently a LCFA.

Very long chain fatty acids (VLCFA) include fatty acids with chains of 22 or more carbons, such as 22-60, 22-50, or 22-40 carbons. In some embodiments, each of the fatty acids is independently a VLCFA. In some embodiments, one of the fatty acids is independently a VLCFA.

In some embodiments, one of the fatty acids is independently a MCFA and one is independently a LCFA.

Pharmaceutically Acceptable Compositions

According to another embodiment, the present invention provides a composition comprising a compound of the present disclosure, for example, a lipid prodrug such as Compound I-1 or a lipid prodrug of Formula I, and a pharmaceutically acceptable carrier, adjuvant, or vehicle. Such compositions are useful in the methods described herein. The amount of lipid prodrug in the composition is an amount effective to treat the relevant disease, disorder, or condition in a patient in need thereof (an "effective amount"). In some embodiments, a composition of the present disclosure is formulated for oral administration to a patient.

The term "pharmaceutically acceptable carrier, adjuvant, or vehicle" refers to a non-toxic carrier, adjuvant, or vehicle that does not destroy the pharmacological activity of the agent with which it is formulated. Pharmaceutically acceptable carriers, adjuvants or vehicles that may be used in the disclosed compositions include, but are not limited to, ion exchangers, alumina, stearates such as aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the composition is formulated as a lipophilic mixture, such as a lipid-based composition.

Compositions of the present invention may be administered orally, parenterally, enterally, intracisternally, intraperitoneally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the composition is administered orally, intraperitoneally, or intravenously. In some embodiments, the composition is a transmucosal formulation. In some embodiments, the composition is injected directly into the lymphatic system. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

To aid in delivery of the composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions.

These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

In some embodiments, the pharmaceutically acceptable composition is formulated for oral administration. Such formulations may be administered with or without food. In some embodiments, the pharmaceutically acceptable composition is administered without food. In other embodiments, the pharmaceutically acceptable composition is administered with food.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Therapeutic agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the lipid prodrug is formulated as an orally administerable, lipid-based formulation. Lipid-based formulations for oral delivery are known in the art and may include, for example, substantially non-aqueous vehicles which typically contain one or more lipid components. The lipid vehicles and resulting lipid formulations may be usefully classified as described below according to their shared common features according to the lipid formulation classification system (LFCS) (Pouton, C. W., *Eur. J. Pharm. Sci.* 11 (Supp 2), S93-S98, 2000; Pouton, C. W., *Eur. J. Pharm. Sci.* 29 278-287, 2006).

Lipid vehicles, and the resulting lipid formulations, may contain oil/lipids and/or surfactants, optionally with co-solvents. In the LFCS terminology, Type I formulations include oils or lipids which require digestion, such as mono, di and tri-glycerides and combinations thereof. Type II formulations are water-insoluble self emulsifying drug delivery systems (SEDDS) which contain lipids and oils used in Type I formulations, with additional water insoluble surfactants. Type III formulations are SEDDS or self-microemulsifying drug delivery systems (SMEDDS) which contain lipids and oils used in Type I formulations, with additional water-soluble surfactants and/or co-solvents (Type Ma) or a greater proportion of water-soluble components (Type IIIb). Type IV formulations contain predominantly hydrophilic surfactants and co-solvents (e.g. PEG, propylene glycol and diethylene glycol monoethyl ether) and are useful for drugs which are poorly water soluble but not lipophilic. Any such lipid formulation (Type I-IV) is contemplated herein for use with a disclosed lipid prodrug or pharmaceutical composition thereof.

In some embodiments, the lipid vehicle contains one or more oils or lipids, without additional surfactants, co-surfactants or co-emulsifiers, or co-solvents, i.e. it consists essentially of one or more oils or lipids. In some further embodiments, the lipid vehicle contains one or more oils or lipids together with one or more water-insoluble surfactants, optionally together with one or more co-solvents. In some embodiments, the lipid vehicle contains one or more oils or lipids together with one or more water-soluble surfactants, optionally together with one or more co-solvents. In some embodiments, the lipid vehicle contains a mixture of oil/lipid, surfactant and co-solvent. In some embodiments, the lipid vehicle consists essentially of one or more surfactants/co-surfactants/co-emulsifiers, and/or solvents/co-solvents.

Examples of oils or lipids which may be used in the present invention include almond oil, babassu oil, blackcurrant seed oil, borage oil, canola oil, castor oil, coconut oil, cod liver oil, corn oil, cottonseed oil, evening primrose oil, fish oil, grape seed oil, mustard seed oil, olive oil, palm kernel oil, palm oil, peanut oil, rapeseed oil, safflower oil, sesame oil, shark liver oil, soybean oil, sunflower oil, walnut oil, wheat germ oil, avocado oil, bran oil, hydrogenated castor oil, hydrogenated coconut oil, hydrogenated cottonseed oil, hydrogenated palm oil, hydrogenated soybean oil, partially hydrogenated soybean oil, hydrogenated vegetable oil, caprylic/capric glycerides, fractionated triglycerides, glyceryl tricaprate, glyceryl tricaproate, glyceryl tricaprylate, glyceryl tricaprylate/caprate, glyceryl tricaprylate/caprate, glyceryl tricaprylate/caprate/laurate, glyceryl tricaprylate/caprate/linoleate, glyceryl tricaprylate/caprate/stearate, glyceryl trilaurate, glyceryl monolaurate, glyceryl behenate, glyceryl monolinoleate, glyceryl trilinolenate, glyceryl trioleate, glyceryl triundecanoate, glyceryl tristearate linoleic glycerides, saturated polyglycolized glycerides, synthetic medium chain triglycerides containing primarily $C_{8-12}$ fatty acid chains, medium chain triglycerides containing primarily $C_{8-12}$ fatty acid chains, long chain triglycerides containing primarily $>C_{12}$ fatty acid chains, modified triglycerides, fractionated triglycerides, and mixtures thereof.

Examples of mono and diglycerides which may be used in such formulations include glycerol mono- and diesters having fatty acid chains from 8 to 40 carbon atoms, including hydrolysed coconut oils (e.g. Capmul® MCM), hydrolysed corn oil (e.g. Maisine™35-1). In some embodiments, the monoglycerides and diglycerides are mono- or di-saturated fatty acid esters of glycerol having fatty acid chains of 8 to 18 carbon chain length (e.g. glyceryl monostearate, glyceryl distearate, glyceryl monocaprylate, glyceryl dicaprylate, glyceryl monocaprate and glyceryl dicaprate). Mixtures of fatty acids ("structured glycerides") adapted for enhancing the absorption and transport of lipid soluble compounds are disclosed in, e.g., U.S. Pat. No. 6,013,665, which is hereby incorporated by reference.

Suitable surfactants for use in the lipid formulations include propylene glycol mono- and di-esters of $C_{8-22}$ fatty acids, such as, but not limited to, propylene glycol monocaprylate, propylene glycol dicaprylate, propylene glycol monolaurate, sold under trade names such as Capryol® 90, Labrafac® PG, Lauroglycol® FCC, sugar fatty acid esters, such as, but not limited to, sucrose palmitate, sucrose laurate, and sucrose stearate; sorbitan fatty acid esters such as, but not limited to, sorbitan laurate, sorbitan palmitate, and sorbitan oleate; polyoxyethylene sorbitan fatty acid esters such as, but not limited to, polysorbate 20, polysorbate 40, polysorbate 60, polysorbate 80, and polysorbate 85; polyoxyethylene mono- and di-fatty acid esters including, but not limited to, polyoxyl 40 stearate and polyoxyl 40 oleate; a mixture of polyoxyethylene mono- and di-esters of $C_{8-22}$ fatty acids and glyceryl mono-, di-, and tri-esters of $C_{8-22}$ fatty acids as sold under tradenames such as Labrasol®, Gelucire® 44/14, Gelucire® 50/13, and Labrafil®; polyoxyethylene castor oils compound such as, but not limited to, polyoxyl 35 castor oil, polyoxyl 40 hydrogenated castor oil, and polyoxyl 60 hydrogenated castor oil, as are sold under tradenames such as Cremophor®/Kolliphor EL, Cremophor®/Kolliphor® RH40, and Cremophor®/Kolliphor® RH60; polyoxyethylene alkyl ethers including, but not limited to, polyoxyl 20 cetostearyl ether and polyoxyl 10 oleyl ether; DL-α-tocopheryl polyethylene glycol succinate; glyceryl mono-, di-, and tri-esters; glyceryl mono-, di-, and tri-esters of $C_{8-22}$ fatty acids; sucrose mono-, di-, and tri-esters; sodium dioctylsulfosuccinate; polyoxyethylene-polyoxypropylene copolymers such as, but not limited to poloxamer 124, poloxamer 188, and poloxamer 407; polyoxyethylene ethers of $C_{8-22}$ fatty alcohols including, but not limited to, polyoxyethylenelauryl alcohol, polyoxyethylenecetyl alcohol, polyoxyethylene stearyl alcohol, polyoxyethyleneoleyl alcohol, as sold under tradenames such as Brij® 35, Brij® 58, Brij® 78, Brij® 98, or a mixture of any two or more thereof.

A co-emulsifier, or co-surfactant, may be used in the formulation. A suitable co-emulsifier or co-surfactant may be a phosphoglyceride; a phospholipid, for example lecithin, or a free fatty acid that is liquid at room temperature, for example, iso-stearic acid, oleic acid, linoelic acid, linolenic acid, palmitic acid, stearic acid, lauric acid, capric acid, caprylic acid, and caproic acid.

Suitable solvents/co-solvents include ethanol, propylene glycol, polyethylene glycol, diethylene glycol monoethyl ether, and glycerol.

A polymer may also be used in the formulation to inhibit drug precipitation or to alter the rate of drug release. A range of polymers have been shown to impart these properties and are well known to those skilled in the art. Suitable polymers include hydroxypropylmethylcellulose, hydroxypropylmethylcellulose acetyl succinate, other cellulose-derived polymers such as methylcellulose; poly(meth)acrylates, such as the Eudragit series of polymers, including Eudragit E100, polyvinylpyrrolidone, or others as described in, e.g. Warren et al., *Mol. Pharmaceutics* 2013, 10, 2823-2848.

Formulations may be chosen specifically to provide for sustained release of the active in the gastrointestinal (GI) tract in order to control the rate of absorption. Many different approaches may be used to achieve these ends including the use of high melting point lipids that disperse/erode slowly in the GI tract, or polymers that form a matrix that slowly erodes. These formulations may take the form of large monolithic dose forms or may be present as micro or nano-particulate matrices as described in, for example, in Mishra, *Handbook of Encapsulation and Controlled Release*, CRC Press, Boca Raton, (2016) ISBN 978-1-4822-3234-9, Wilson and Crowley, *Controlled Release in Oral Drug Delivery*, Springer, NY, ISBN 978-1-4614-1004-1 (2011) or Wise, *Handbook of Pharmaceutical Controlled Release Technology*, Marcel Dekker, NY, ISBN 0-82467-0369-3 (2000).

Formulations may also contain materials commonly known to those skilled in the art to be included in lipid based formulations, including antioxidants, for example, butylated hydroxyanisole (BHA) or butylated hydroxytoluene (BHT) and solidifying agents such as microporous silica, for example magnesium alumino-metasilicate (Neusilin).

In some embodiments, the lipid prodrug may be co-administered orally with an enzyme inhibitor to increase stability of the prodrug in the gastrointestinal tract or enterocyte. In certain embodiments, the enzyme inhibitor inhibits pancreatic lipases, examples of which include, but are not limited to, Alli® (orlistat). In other embodiments it is envisaged that the enzyme inhibitor will inhibit cellular lipase enzymes such as monoacylglycerol lipase, an example of which includes, but is not limited to, JZL184 (4-nitrophenyl-4-[bis(1,3-benzodioxol-5-yl)(hydroxy) methyl]piperidine-1-carboxylate).

General Methods for Making Lipid Prodrugs

The lipid prodrug compounds of this invention may be prepared or isolated in general by synthetic and/or semi-synthetic methods known to those skilled in the art for analogous compounds and by methods described in detail in, for example, WO 2019/046491, WO 2017/041139, and WO 2016/023082, each of which is hereby incorporated by reference in its entirety.

The therapeutic agents comprised in disclosed lipid prodrugs (e.g., conjugated to a glyceride-based prodrug) may be purchased commercially or prepared by organic synthesis, semi-synthesis, fermentation (e.g. with viral vectors), and like methods known in the art.

In some embodiments, protecting groups (as defined below) can be used to manipulate therapeutic agents in preparation for conjugation to the remainder of the lipid prodrug structure, for example, to prevent undesired side reactions from taking place.

In the synthesis methods described herein, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 7th Edition, John Wiley & Sons, 2013, *Comprehensive Organic Transformations*, R. C. Larock, 3rd Edition, John Wiley & Sons, 2018, and *Protective Groups in Organic Synthesis*, P. G. M. Wuts, 5th edition, John Wiley & Sons, 2014, the entirety of each of which is hereby incorporated herein by reference.

As used herein, the phrase "leaving group" (LG) includes, but is not limited to, halogens (e.g., fluoride, chloride, bromide, iodide), sulfonates (e.g., mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protective Groups in Organic Synthesis*, P. G. M. Wuts, 5th edition, John Wiley & Sons, 2014, and Philip Kocienski, in *Protecting Groups*, Georg Thieme Verlag Stuttgart, New York, 1994, the entireties of which are incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protective Groups in Organic Synthesis*, P. G. M. Wuts, 5th edition, John Wiley & Sons, 2014, and Philip Kocienski, in *Protecting Groups*, Georg Thieme Verlag Stuttgart, New York, 1994, the entireties of which are incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, *March's Advanced Organic Chemistry: Reactions, Mechanisms, and Structure*, M. B. Smith and J. March, 7th Edition, John Wiley & Sons, 2013, *Comprehensive Organic Transformations*, R. C. Larock, 3rd Edition, John Wiley & Sons, 2018, the entirety of each of which is incorporated herein by reference. Such interconversions may require one or more of the aforementioned techniques, and certain methods for synthesizing compounds of the invention are described below.

As a general strategy, compounds of the present invention may be synthesized via one of the following routes:

Scheme 1. Synthesis of compounds of formula iii.

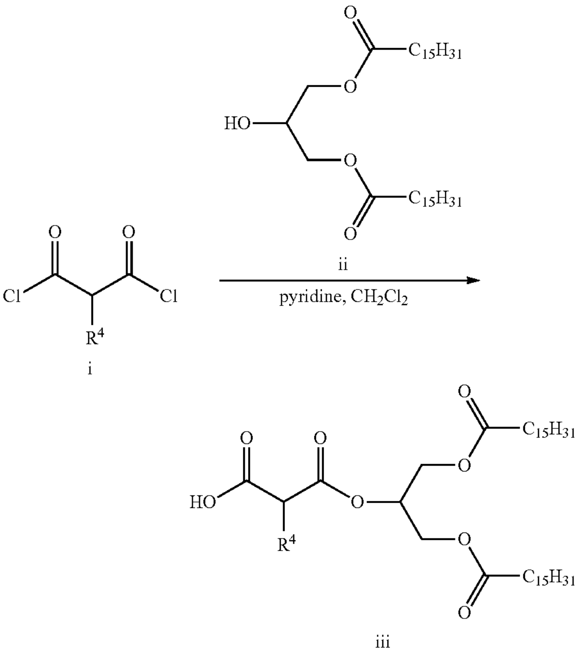

Diacid chlorides i, which are readily available from the corresponding malonic acids, can be reacted with a diglyceride such as ii in the presence of pyridine or another appropriate base to give acid-triglyceride (acid-TG) iii (see Scheme 1). Formula iii is shown with $C_{15}H_{31}$ fatty acid side chains, but other fatty acids (such as those described above) can be substituted in this and other Formulas described below.

Scheme 2. Synthesis of compounds of formula iii.

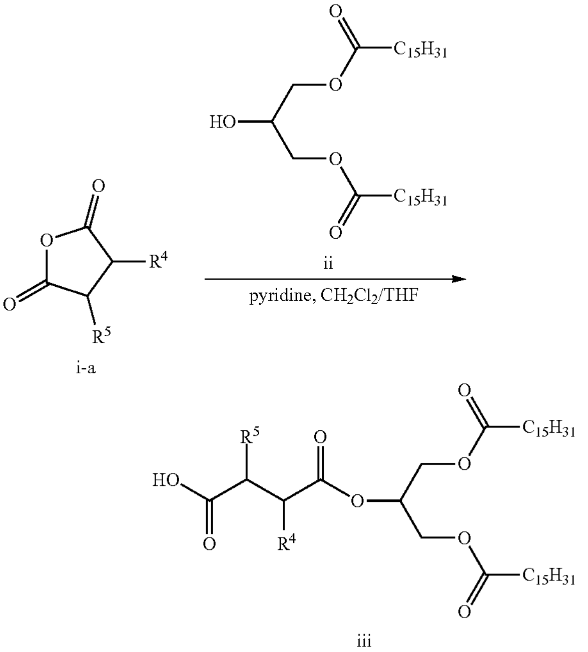

In cases where acid anhydride i-a is available, acid-TG iii can be generated by ring-opening with diglyceride ii in the presence of pyridine or another appropriate base (Scheme 2). This method works best when $R^4$ and $R^5$ of acid anhydride i-a are identical, e.g. both Me, but will result in a regioisomeric mixture of acid-TG products iv when $R^4$ and $R^5$ differ from each other. Consequently, other methods, such as that outlined in Scheme 3, can advantageously be employed in this circumstance.

Scheme 3. Synthesis of compounds of formula iv where $R^4$ = Me, Alkyl, etc. and $R^5$ = H.

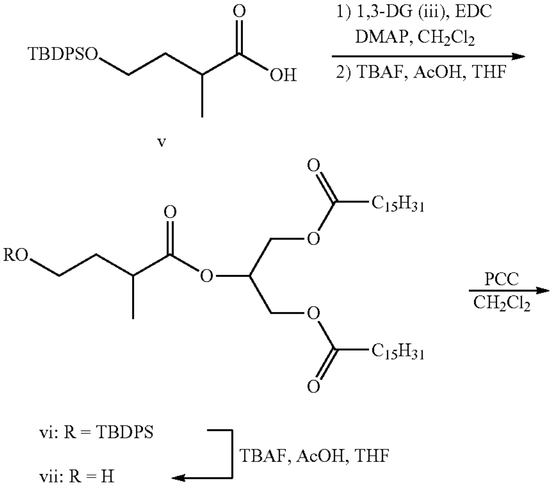

-continued

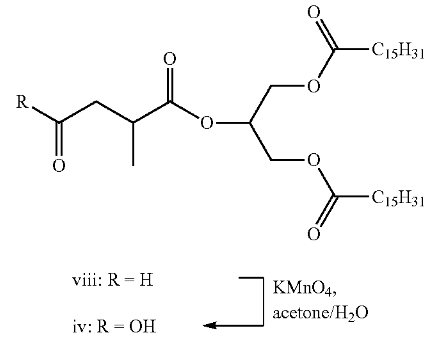

To obtain acid-TG iv as a single regioisomer in the specific example where $R^4$=Me or other alkyl or substitution and $R^5$=H, the known carboxylic acid v (Lienard, B. M. R. et al., *Org. Biomol. Chem.* 2008, 6, (13), 2282-2292) can be used as a starting point (see Scheme 3). Coupling of acid v with 1,3-DG ii under standard conditions produces TBDPS protected triglyceride vi, which can be treated with appropriate conditions such as TBAF and AcOH to afford alcohol vii. A two-step oxidation process (for example, PCC, then $KMnO_4$) can then be used to transform alcohol vii into the desired acid-TG iv via the intermediate aldehyde viii.

Scheme 4. Synthesis of compounds of formula x wherein -M- is an acetal self-immolative (ASI) group.

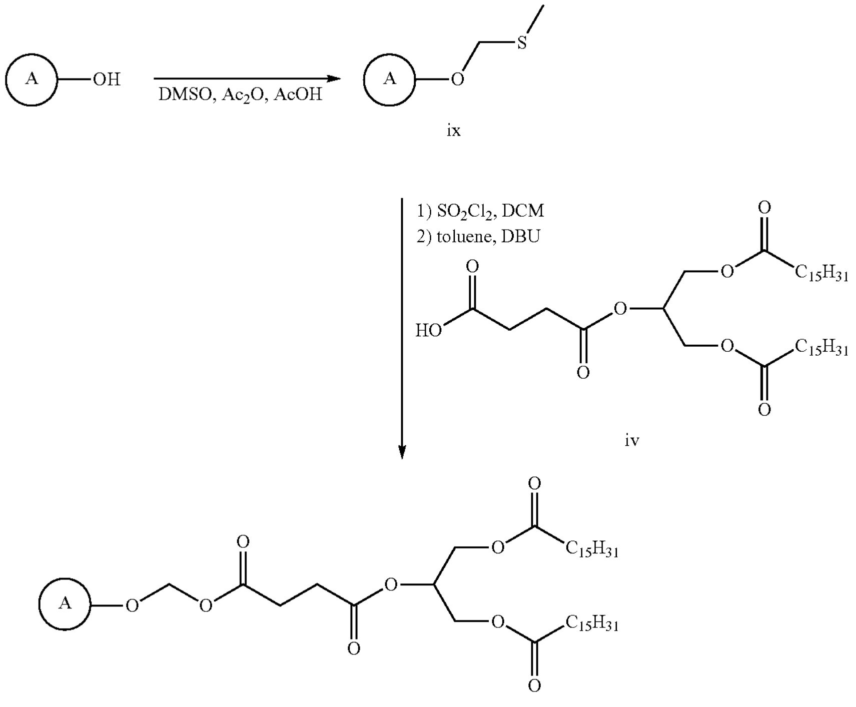

x

For the synthesis of compounds containing an acetal self-immolative (ASI) group between the pharmaceutical agent and the alkyl spacer, the alcohol-bearing parent molecule must be functionalized and activated prior to conjugation with acid-triglyceride iii as outlined above in Scheme 4. Treatment of an alcohol with DMSO in a mixture of acetic anhydride and acetic acid results in the formation of (methylthio)methyl (MTM) ether ix. Activation of MTM ether ix using sulfuryl chloride forms a presumed sulfoxide species that can react with the carboxylate of acid-triglyceride iv to give the target compound x.

Scheme 5. Synthesis of compounds of formula xii wherein -M- is a carboxyacetal (CASI) or carboxy(methylacetal) (CMSI) self-immolative group.

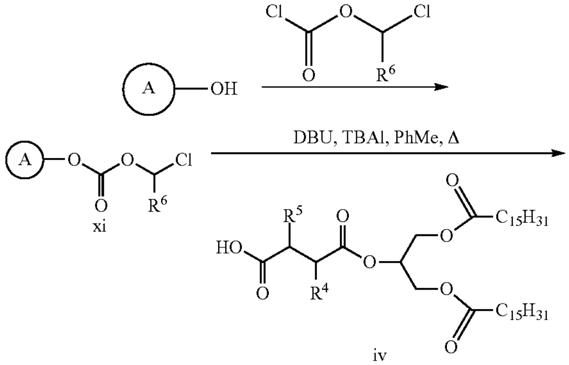

xi iv

-continued

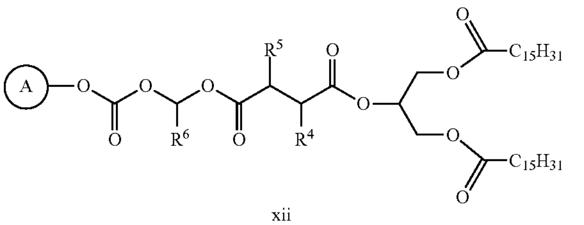

xii

In cases where the pharmaceutical agent contains an alcohol, phenol or amine (primary or secondary) functional group, a modified version of the acetal self-immolative group can be used where an additional carboxy group is included. Reaction of the parent drug with a chloroalkyl chloroformate gives chloroalkyl carbonates (shown) or carbamates xi (see Scheme 5). Displacement of the halide leaving group is then accomplished by treatment with the carboxylate derived from acid-TG iv in an appropriate solvent such as refluxing toluene to afford the target compound xii.

Scheme 6. Synthesis of compounds of formula xviii wherein -M- is a trimethyl-lock (TML) self-immolative group.

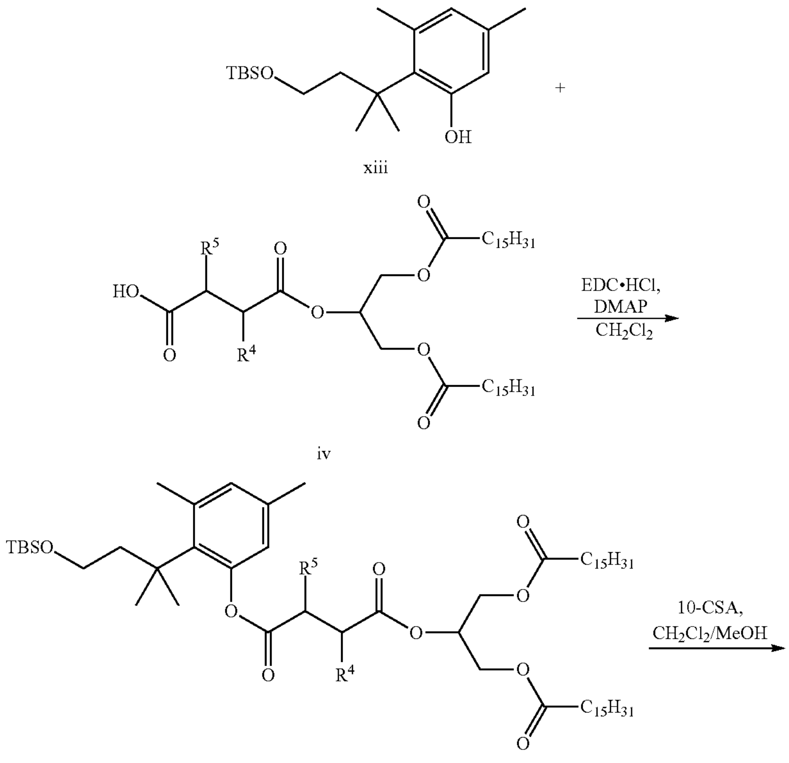

xiii iv xiv

-continued

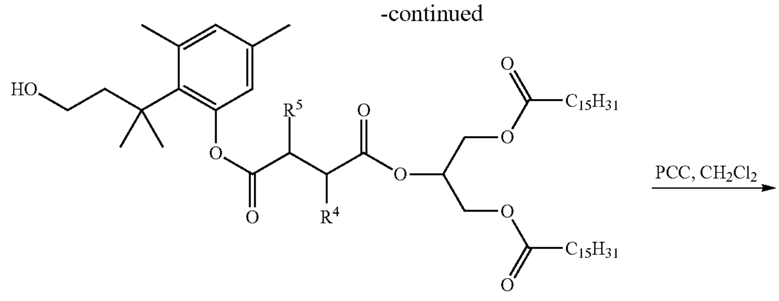

xv

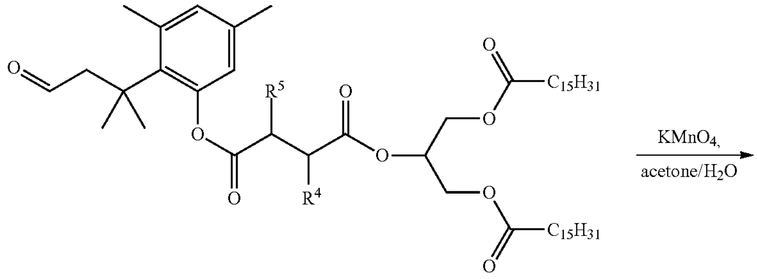

xvi

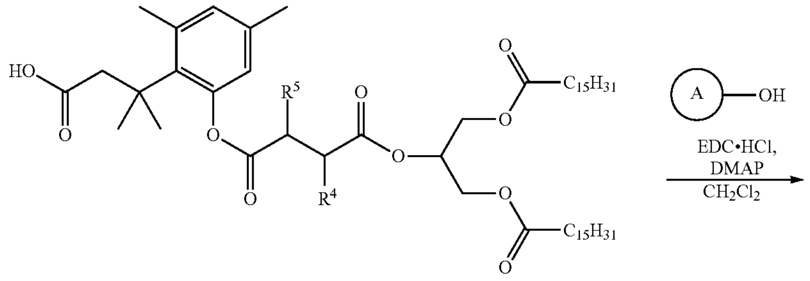

xvii

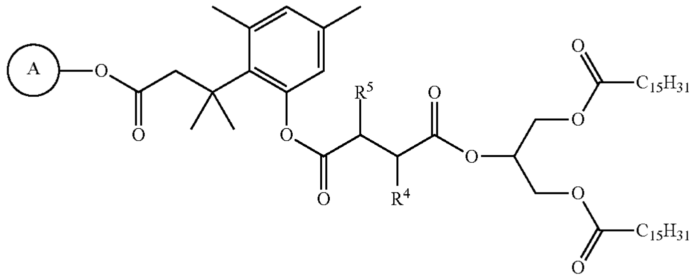

xviii

For the synthesis of prodrugs containing a trimethyl lock (TML) self-immolative group (Levine, M. N.; Raines, R. T. Chem. Sci. 2012, 3, 2412-2420, hereby incorporated by reference) between the pharmaceutical agent and the alkyl spacer to facilitate systemic release of the parent molecule, the acid-triglyceride iv must be functionalized with the TML moiety prior to conjugation with a pharmaceutical agent as outlined in Scheme 6. Coupling of acid-TG iv with TML phenol xiii under standard conditions gives triglyceride xiv, which can be deprotected under acidic conditions (10-camphorsulfonic acid) to give alcohol xv. Sequential oxidation of alcohol xv firstly to aldehyde xvi and then acid xvii, followed by coupling to either an alcohol (shown), amine or sulfonamide-containing pharmaceutical agent under standard conditions can give the target compound xviii.

Scheme 7. Synthesis of compounds of formula xxiv wherein -M- is a p-hydroxybenzyl carbonyl (PHB) self-immolative group.

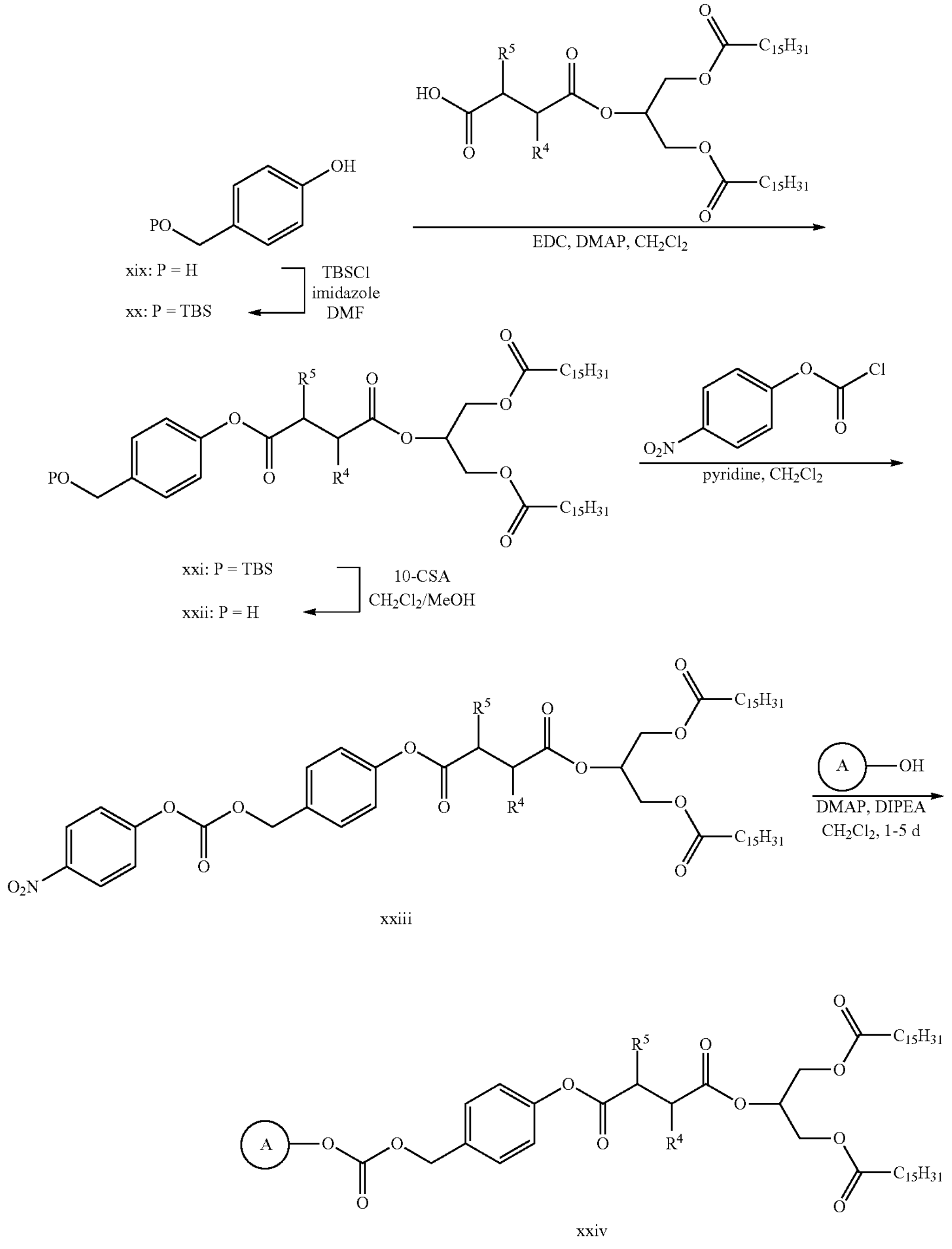

For the synthesis of compounds containing a p-hydroxybenzyl (PHB) carbonyl self-immolative group, the primary hydroxyl group of p-hydroxybenzyl alcohol (xix) is first protected as a silyl ether and the free phenolic hydroxyl group coupled with acid-TG iv to give PHB triglyceride xxi (see Scheme 7). After removal of the silicon protecting group, primary alcohol xxii can be activated by treatment with p-nitrophenyl (PNP) chloroformate to give PNP carbonate xxiii. Displacement of the PNP group is then achieved by reaction with a pharmaceutical agent (A-OH shown) under basic conditions to give the desired compound xxiv.

Scheme 8. Synthesis of compounds of formula III wherein -M- is a flipped-ester self-immolative (FSI) group.

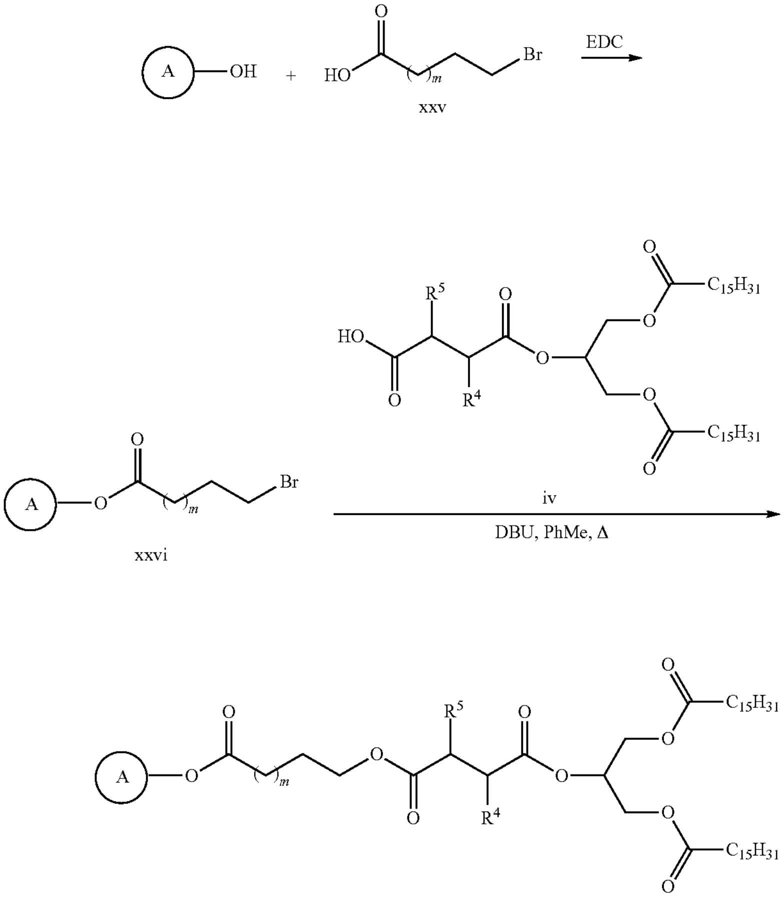

xxv, xxvi, xxvii

Without wishing to be bound by theory, it is believed that the flipped-ester self-immolative (FSI) group can liberate the free pharmaceutical agent by a cyclization mechanism, resulting in loss of either a four-carbon (FSI-4) or five-carbon (FSI-5) lactone. Alternatively, liberation of the agent may occur by a chemical or enzymatic mechanism in vivo. FSI prodrugs can be synthesized by coupling the pharmaceutical agent (A-OH shown) with either 4-bromobutyric acid (m=1) or 5-bromovaleric acid (m=2) (xxv) to give bromide xxvi (see Scheme 8). Displacement of bromide xxvi using the carboxylate derived from acid-TG iv generates the desired ester bond in target compound xxvii.

EXEMPLIFICATION

Results of the experiments described in the Examples below are depicted in the Figures and described above in the Detailed Description.

Materials: 3T3-L1 cells were purchased from ATCC cell lines (VA, USA). Dulbecco's Modified Eagle Medium (DMEM), fetal bovine serum (FBS), streptomycin and penicillin, pyruvate, ACK red blood cell lysis buffer and Roswell Park Memorial Institute 1640 (RPMI 1640, 11875-093) medium were purchased from Gibco, Thermo Fisher Scientific (VIC, Australia). TaqMan™ PCR universal master mix was purchased from Applied Biosystems (4304437, VIC, Australia). Dexamethasone (D4902), 3-isobutyl-1-methylxantine (IBMX, 17018), phorbol 12-myristate 13-acetate (PMA, P8139), RIPA buffer, 2-deoxy-glucose (2DG, D8375), Triton X-100 (X100), Evans blue (E2129), NaCl, KCl, $NaHCO_3$, $NaH_2PO_4$, $MgCl_2$ and $CaCl_2$ were purchased from Sigma Aldrich (Australia). $^{14}C$-2-deoxy-glucose ($^{14}C$-2DG, NEC720A050UC) and ULTIMA Gold uLLT (ultra-low level LSC, 6013687) were purchased from PerkinElmer (VIC, Australia). Isopropanol, ethanol and chloroform were purchased from Merck (Darmstadt, Germany). Insulin (Actrapid) 100 units/ml was purchased from Roche (Switzerland). QIAzol lysis reagent (79306) was purchased from QIAGEN (Australia). Water was obtained from a MilliQ water purification system. All other reagents were laboratory grade or above.

Statistical Analysis: Statistics were analyzed using GraphPad Prism version 7 (GraphPad Software Inc., La Jolla, CA, USA). The data are presented as mean+standard error of the mean (SEM). Differences between two groups were analyzed using a Student's t-test and for more than two groups with a one-way or two-way analysis of variance (ANOVA) with Bonferroni post-hoc test. A p value less than 0.05 was considered statistically significant.

Example A: Synthesis of Compound I-1

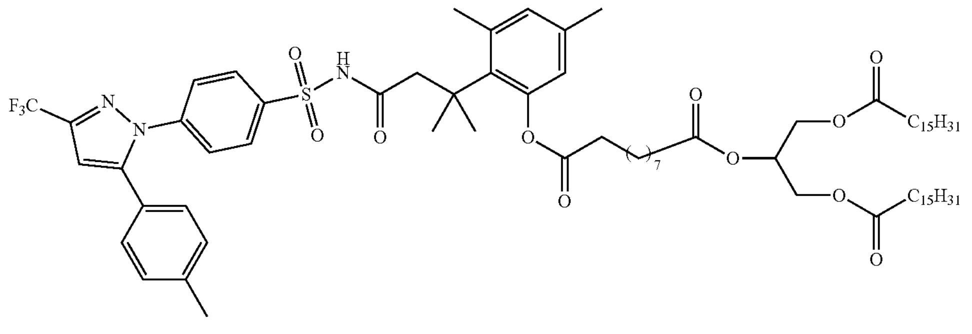

4-(Dimethylamino)pyridine (DMAP, 184 mg, 1.50 mmol), N-(3-dimethylaminopropyl)-N'-ethylcarbodiimide hydrochloride (EDC·HCl, 721 mg, 3.76 mmol), triethylamine (629 μL, 4.51 mmol) and celecoxib (688 mg, 1.80 mmol) were added to a solution of the carboxylic acid corresponding to the prodrug portion of the desired compound (1.44 g, 1.50 mmol) in $CH_2Cl_2$ (40 mL) and the mixture stirred at rt for two days and 22 hours. The reaction was diluted with $CH_2Cl_2$ (30 mL), silica gel was added and the mixture concentrated under reduced pressure. Purification by silica gel chromatography (35% to 100% ethyl acetate/hexanes) gave celecoxib prodrug I-1 (1.04 g, 52%) as a colourless oil; $^1H$ NMR (400 MHz, $CDCl_3$) δ 8.74 (s, 1H), 7.79-7.73 (m, 2H), 7.43-7.36 (m, 3H), 7.17 (d, J=8.0 Hz, 2H), 7.11 (d, J=8.2 Hz, 2H), 6.74 (s, 1H), 6.66 (d, J=1.4 Hz, 1H), 6.54 (d, J=1.5 Hz, 1H), 5.26 (m, 1H), 4.30 (dd, J=11.9, 4.4 Hz, 2H), 4.15 (dd, J=11.9, 5.6 Hz, 2H), 2.62 (t, J=7.6 Hz, 2H), 2.38 (s, 3H), 2.35-2.29 (m, 8H), 2.25 (s, 3H), 2.07 (s, 3H), 1.85-1.74 (m, 2H), 1.68-1.58 (m, 6H), 1.56 (s, 6H), 1.46-1.20 (m, 56H), 0.88 (t, J=6.8 Hz, 6H); $^{13}C$ NMR (101 MHz, $CDCl_3$) δ 176.2 (C), 173.5 (2C; C), 173.0 (C), 169.1 (C), 150.5 (C), 145.3 (C), 143.3 (C), 140.0 (C), 138.8 (C), 138.1 (C), 137.7 (C), 133.8 (CH), 131.9 (C), 129.9 (2C; CH), 129.7 (2C; CH), 128.9 (2C; CH), 125.9 (C), 124.9 (2C; CH), 123.5 (CH), 106.6 (CH), 69.1 (CH), 62.2 (2C; $CH_2$), 49.9 ($CH_2$), 40.5 (C), 35.4 ($CH_2$), 34.3 ($CH_2$), 34.2 (2C; $CH_2$), 32.3 (2C; $CH_3$), 32.1 ($CH_2$), 29.85 (6C; $CH_2$), 29.81 (4C; $CH_2$), 29.77 (2C; $CH_2$), 29.6 (2C; $CH_2$), 29.5 (2C; $CH_2$), 29.4 (2C; $CH_2$), 29.30 ($CH_2$), 29.27 (2C; $CH_2$), 29.22 ($CH_2$), 29.19 ($CH_2$), 29.13 ($CH_2$), 25.6 ($CH_3$), 25.0 (2C; $CH_2$), 24.9 ($CH_2$), 24.8 ($CH_2$), 22.8 (2C; $CH_2$), 21.5 ($CH_3$), 20.3 ($CH_3$), 14.3 (2C; $CH_3$); ESI-HRMS: calcd. for $C_{75}H_{113}F_3N_3O_{11}S$ $[M+H^+]$1320.8042; found 1320.8018.

Example 1: Rodent HFD Studies—Observation, Prevention, and Treatment

All animal work was conducted per Australian National Health and Medical Research Council (NHMRC) guidelines for the care and use of animals in research. Seven-week-old male Sprague Dawley rats or C57BL6/J mice were randomized and housed in groups of 2-5 in a temperature-controlled room under specific-pathogen free (SPF) or standard animal housing conditions with free access to food and water.

In the observational studies, mice or rats were fed semi-purified normal chow diet (control fat diet (CFD), 7% w/w fat and 16% total energy from fat, AIN93G, Specialty Feeds Pty Ltd, Australia) or high fat diet (HFD, 36% w/w fat and 59% total energy from fat, SF03-002, Specialty Feeds Pty Ltd, Australia) for a total duration of 6, 15, 23 or 32 weeks to evaluate changes to mesenteric lymph composition, structure and function over time during the progression of obesity. Mice or rats were fed with the same CFD or HFD for 6-10 weeks prior to collection of mesenteric lymph for in vitro incubation with lymphatic endothelial cells (LECs) and adipocytes, respectively.

A "prevention study" and a "treatment study" were also conducted. Both the prevention and treatment studies included mice fed the CFD or HFD for 15 or 23 weeks, as described above. In the prevention study, an additional group of mice was fed the HFD supplemented with celecoxib at a dose equivalent to ~29 mg/kg/day (based on average food intake) for 15 weeks. In the treatment study, animals were fed the HFD for 15 weeks followed by a HFD supplemented with celecoxib (~29 mg/kg/day) or Compound I-1 (~9 mg/kg/day celecoxib equivalents) for 7-8 weeks. Timelines for these studies are given in FIGS. 4*g* and 5*a*. The celecoxib was purchased from MedChemExpress (NJ, USA), and Compound I-1 was synthesized consistent with the description in WO2016/023082.

Across all studies, body mass was measured once per week. Oral glucose tolerance tests (OGTTs) were conducted at 5, 14, 22 and/or 31 weeks after commencing feeding mice the HFD or CFD. To perform OGTTs, mice were routinely handled for 2 weeks prior to minimize the stress caused by handling during the experiment. On the day of the OGTT, mice were fasted for 4 h (7-11 am) but still had free access to water. Glucose (50 mg D-glucose in 200 μL water) was administered via oral gavage and a drop of blood was collected from the tail tip at fixed time points (0, 15, 30, 60, 90 and 120 mins). Blood glucose was measured using a One-touch glucometer (AccuCheck Performa, Roche, Switzerland). Plasma was separated from the remaining blood sample via centrifugation and reserved for measurement of plasma insulin concentrations via ELISA as described above.

At the end of all experiments, mice were euthanised via cervical dislocation and rats were euthanised via intracardiac injection of sodium pentobarbitone (100 mg). Organs and tissues, including the lymph nodes and adipose tissue depots, were carefully collected. The mass of adipose tissue depots was weighed to determine adiposity.

Example 2: Mesenteric Lymphatic Structural Analysis

Mesenteric adipose tissue samples (for lymphatic capillary and mesenteric lymphatic vessel analysis) and small intestine samples (for villi and lacteal analysis) were collected with fine forceps. Whole mount adipose tissue was cut into ~3 mm×3 mm×2 mm pieces and whole mount small intestine was cut into 1.5 cm segments. Immediately after collection, the tissue samples were fixed in 4% paraformaldehyde in PBS at 4° C. overnight. Fat associated lymph clusters (FALCs) were identified by intraperitoneal injection of FluoSphere Carboxylate-Modified Nanospheres, 100 nm, yellow-green (505/515, Invitrogen, CA, USA) and collected with fine forceps under a Zeiss Stemi 2000-CS surgical microscope (2.5× magnification) with a fluorescence adaptor (Nightsea, MA, USA). The fluorescent light was filtered through a cyan color light filter (Electron Microscopy Science, PA, USA) to visualize the nanospheres and thus the FALCs. FALCs were cleaned of adipose tissue after collected and placed whole in 4% paraformaldehyde in PBS at 4° C. overnight.

Tissues and FALC were blocked with 3% w/v bovine serum albumin (BSA, Sigma, Missouri, USA) in PBS at 4° C. for 12-24 h and then incubated with primary antibodies (Table 1) including either 0.4 μg/mL rabbit anti-LYVE-1 antibody (Fitzgerald, MA, USA), 2.5 μg/mL rat anti-CD31 (BD Biosciences), 2.5 μg/mL rat anti-CD11b (Biolegend), 2.5 μg/mL rat anti-B220 (Biolegend), 1:1000 mouse anti-alpha smooth muscle actin-Cy3 (Sigma, Missouri, USA) (to identify smooth muscle coverage) and 2.5 μg/mL rat anti-CD4 (Biolegend) for 3-4 days at 4° C. After this initial incubation, tissues were next incubated with secondary antibodies (Table 1) including either 4 μg/mL goat anti-rat or anti-rabbit Alexa Fluoro 488 antibody, 4 μg/mL goat anti-rat or anti-rabbit Alexa Fluoro 647 antibody or 2 μg/mL goat anti-rat Alexa Fluoro 568 antibody (Invitrogen, CA, USA) depending on the host species of the primary antibodies. Some samples were also incubated with , 4 μg/mL Dylight 405 goat anti-rat antibody (Jackson ImmunoResearch Laboratories, PA, USA), 5 μg/mL Bodipy FA C16 fatty acid (to identify lipid droplets in adipocytes, Invitrogen, CA, USA) and/or 1:200 Hoechst (to identify nuclei, Invitrogen, CA, USA). Some samples required staining with primary antibodies from the same host species concurrently. This sequential primary antibody staining was achieved through an additional blocking step with 10% rat serum (Sigma, Missouri, USA) followed by 10 μg/mL goat anti-rat Fab fragments (Jackson ImmunoResearch Laboratories, Inc., West Grove, USA) in between primary antibody staining. In the case of the small intestine, after staining the whole mount small intestine tissue, a 0.5 mm segment, containing on average 10-15 individual villi, was isolated for confocal imaging of the villi and lacteals. All the stained tissues were mounted on slides with Dako Fluorescent mounting medium (Dako, Glostrup, Denmark).

TABLE 1

Primary antibodies, secondary antibodies and other reagents used in tissue immunofluorescence analysis

| Primary Antibody | Clone | Supplier | Dilution | Tissue types |
|---|---|---|---|---|
| Rabbit anti-LYVE-1 | Polyclonal | Fitzgerald, MA, USA | 1:200 | Villus, adipose tissue, FALC |
| Rat anti-CD31 | MEC13.3 | BD Biosciences, NSW, Australia | 1:200 | Villus, adipose tissue, FALC |
| Rat anti-CD11b | M1/70 | BioLegend, San Diego, CA, USA | 1:200 | FALC |
| Rat anti-B220 | RA3-6B2 | BioLegend, San Diego, CA, USA | 1:200 | FALC |
| Rat anti-CD4 | RM4-4 | BioLegend, San Diego, CA, USA | 1:200 | FALC |
| Mouse anti-alpha SMA-Cy3 | 1A4 | Sigma, Missouri, USA | 1:1000 | Adipose tissue, FALC |
| Secondary antibody and other reagents | | | | |
| Dylight 405 goat anti-rat antibody | | Jackson ImmunoResearch Laboratories Inc., West Grove, USA | 1:500 | FALC |
| Alexa Fluoro 488 goat anti-rabbit antibody | | Invitrogen, CA, USA | 1:500 | Villus, adipose tissue, FALC |
| Alexa Fluoro 488 goat anti-rat antibody | | Invitrogen, CA, USA | 1:500 | Villus, adipose tissue, FALC |
| Alexa Fluoro 647 goat anti-rabbit antibody | | Invitrogen, CA, USA | 1:500 | Villus, adipose tissue, FALC |
| Alexa Fluoro 647 goat anti-rat antibody | | Invitrogen, CA, USA | 1:500 | Villus, adipose tissue, FALC |
| Alexa Fluoro 568 goat anti-rat antibody | | Invitrogen, CA, USA | 1:500 | Villus, adipose tissue, FALC |
| Goat anti-rat Fab fragments | | Jackson ImmunoResearch Laboratories Inc., West Grove, USA | 1:500 | FALC |
| Bodipy FA C16 fatty acid | | Invitrogen, CA, USA | 1:200 | Adipose tissue |

The tissues were imaged using a Leica SP8 inverted confocal microscope with a 20× Plan Apo CS2 NA0.75 objective controlled by LAS AF image acquisition and processing software (Leica, Wetzlar, Germany). Excitation and emission were set to 405-490 nm for Alexa 405, 495-550 nm for Alexa 488, 550-600 nm for Alexa 568 and 600-700 nm for Alexa 647. The image format was 512×512 pixels and scan frequency was 400 Hz. Z-stacks were obtained at a step size of 5.5-6 μm and images were captured as a tilescan to ensure that the lymphatic vasculature pattern in the entire tissue was captured. Captured images were analyzed using Fiji (Image J) software.

To assess the width of the intestinal villi and lacteals, three lines were drawn manually across the width of each villi/lacteal at different positions along the length of the villi or lacteal (i.e. at the base, midpoint and close to the tip), using the straight-line drawing tool that is built into the Image J software. The distance of each line was quantified and the width of the villi or lacteals taken from the average. To assess the length of the villi and lacteals, a single line was drawn manually from the tip to the base of the villi or lacteal. The measurement of this line was taken as the length of the villi/lacteal.

The number of LYVE-1+ cells (macrophages and LECs) in mesenteric adipose tissue was assessed by selecting LYVE-1+ cells that were above the threshold set as the positive signal. From this threshold the percentage area of the mesenteric adipose tissue image that stained positive for LYVE-1 was quantified. The total number of adipocytes in the same image field was counted based on the number of individual lipid droplets (as each adipocyte contains one large lipid droplet). Lipid droplets were counted in Image J using the find maxima command with a noise tolerance of 100 and exclusion of the edge maxima. This selected all positive objects that had a signal greater than background and summed the count of them. A ratio of the area of LYVE-1+ cells divided by the total number of adipocytes was then calculated for each mesenteric adipose tissue whole mount section.

To quantify mesenteric collecting lymphatic vessel branching in the visceral adipose tissue (VAT), a lymphatic vessel branching ratio was calculated as follows:

$$\text{Lymphatic vessel branching ratio} = \frac{\sum \text{length of all lymphatic vessel branches} + \text{length of main collecting lymphatic vessel}}{\text{Absolute displacement of main collecting lymphatic vessel}}$$

where the 'main collecting lymphatic vessel' was the predominant single lymphatic vessel that ran in parallel to the predominant single blood vessel in the imaged area. The 'length of all lymphatic vessel branches' was calculated from the length of lines manually traced to cover all accessory lymphatic vessels that branched out from the 'main collecting lymphatic vessel' using the freehand line tool in Image J. The 'length of main collecting lymphatic vessel' was also manually traced using the freehand line tool and calculated from the exact length of the main collecting lymphatic vessel (i.e. the traced line) including any curves. The 'absolute displacement of main collecting lymphatic vessel' was the length of a straight line drawn from one end of the 'main collecting lymphatic vessel' to the other end using the straight line drawing tool.

Example 3: Quantification of Lymph 'Leakiness' by Evans Blue Dye Lymphangiography Mesenteric lymphatic vessel drainage and the extent of lymphatic vessel leakiness were quantified using a novel Evans blue dye lymphangiography method. First, mice were anaesthetised with isoflurane gas delivered via a nose cone and their body temperature was maintained at 37° C. throughout surgery and live imaging using a heated surgical board (Ratek Instruments, Australia). All surgical instruments were immersed in 70% v/v ethanol for 30 min prior to surgery. The top skin layer and the muscle wall of the abdomen were opened with a straight 2.0-2.5 cm incision extending across the middle of the abdomen approximately 0.5 cm below the ribcage. The duodenum and jejunum were identified using the end of the stomach as a reference point. The duodenum and upper jejunum were externalised through the abdominal incision and regularly moistened with warm PBS. Peyer's patches were identified by observing the intestinal anatomy through a surgical stereomicroscope. There were typically 2-3 Peyer's patches on the duodenal and upper jejunal area, and the positions of the patches were relatively consistent across animals. A 4-5 cm segment of duodenum and/or jejunum with a Peyer's patch was then isolated by suturing both ends of the segment. Next, 5 μL of 10% Evans blue dye was injected into the uppermost superficial layer of the Peyer's patch with a steady force and at a steady rate using a 0.3 mL insulin syringe with a 31 gauge needle. Tracking of the movement of the Evans blue dye through the mesenteric lymphatic vessels and leakage into the surrounding VAT began immediately after injection. Images were taken at 2, 5, 10, 20 and 30 min post-injection. This 30 min imaging timeframe was chosen as it was found to be sufficient to observe dye drainage into the lymphatic vessel and leakage into surrounding adipose tissue. In addition, the majority of the dye at the injection site was cleared within 30 min in all mice examined. Images were captured using a Zeiss Stemi 2000-CS surgical microscope mounted with an Axiocam ERc 5s camera and AxioVision software with 2.5× magnification (Zeiss, Oberkochen, Germany).

Captured images were analyzed using Image J software. Evans blue leakage from the mesenteric lymphatic vessels into the surrounding adipose tissue was quantified at the 4 to 5 most 'leaky' sites along the lymphatic vessel at the 10 min post-injection time point. This time point was chosen for quantification because the majority of the dye was drained from the injection site into the lymphatic vessels and there was also sufficient time for the dye to leak to surrounding adipose tissue. Additionally, the intensity of the dye in the lymphatic vessel and adipose tissue at 10 min post-injection was generally at its peak and thus provided the most contrast against the background, which enabled more accurate quantification. The red channel (560 nm) of the image was used for quantification as this provided the greatest contrast against the background in adipose tissue. To quantify the degree of blue dye leakage from the lymphatic vessel to surrounding adipose tissue a straight line with thickness of ~10 pixels was drawn across the blue dye stained lymphatic vessel (perpendicular to the flow of the vessel) using the straight-line selection tool in Image J. The straight line was also extended into the surrounding adipose tissue. The straight line was recorded to the ROI Manager of Image J. Dye intensity was measured from the centre of the lymphatic vessel outwards to the surrounding adipose tissue. This resulted in a bell-shaped intensity distribution, where the greatest dye intensity was within the lymphatic vessel and levels decreased at and beyond the sides of the vessel. To enable quantification and statistical comparison of lymph leakage across different groups, the area under the curve of the dye intensity versus distance profile was calculated.

Example 4: Mesenteric Lymph Fluid Collection

The efferent mesenteric lymphatic duct was cannulated in non-fasted mice or rats between 5 am to 7 am, and lymph fluid was collected for up to 4 h post-cannulation, to ensure that the animals were in a partial post-prandial state. The only exception were the experiments to evaluate lymphatic uptake of celecoxib and celecoxib prodrug, which were instead conducted in mice that were fasted for 3-4 h prior to surgery. Fasting was preferred for the latter experiments because the mass of drug or prodrug recovered in lymph may vary with the presence of dietary lipids in the gut. Prior to surgery, animals were anaesthetised with isoflurane gas delivered through a nose cone. Animals were placed on a heated surgical board maintained at 37° C. throughout the surgical procedure and lymph collection. All surgical instruments were immersed in 70% v/v ethanol for 30 min prior to surgery. The superior efferent mesenteric lymphatic duct of rats and mice was cannulated according to previously described procedures (Trevaskis, N. L., et al. The Mesenteric Lymph Duct Cannulated Rat Model: Application to the Assessment of Intestinal Lymphatic Drug Transport. *JoVE*, e52389 (2015); and Trevaskis, N. L., et al. A Mouse Model to Evaluate the Impact of Species, Sex, and Lipid Load on Lymphatic Drug Transport. *Pharm. Res.* 30, 3254-3270 (2013).). Mesenteric lymph fluid was collected continuously into a tube containing 5 μL of 1000 IU/mL heparin in saline for up to 4 h for all experiments except for the celecoxib and prodrug lymphatic uptake experiments for which lymph fluid was collected for 6 h. The CFD and HFD rat lymph fluid was used for co-culture with 3T3-L1 adipocytes as described below. The CFD and HFD mouse lymph fluid was divided for the following assessments: (1) ELISA analysis of vascular endothelial growth factor C (VEGFc) and prostaglandin E2 (PGE2) (20-40 μL aliquots); (2) lipidomic analysis where 30-50 μL of the fresh lymph was immediately extracted with 180-200 μL 2:3 v/v methanol:chloroform with a 1 min vortex followed by snap freezing; (3) triglyceride (TG), free fatty acid (FFA), phospholipid (PL), glucose and cholesterol (Ch) concentration analysis (5 μL aliquots); (4) immune cell analysis by flow cytometry (30-50 μL fresh lymph, used immediately after collection); (5) cell culture incubation with lymphatic endothelial cells (LECs) in the migration assay described below (~100 μL fresh lymph kept at 4° C.).

Example 5: Co-Culture of 3T3-L1 Adipocytes with Mesenteric Lymph Fluid

3T3-L1 fibroblasts differentiate into pre-adipocytes (containing small intracellular lipid droplets) and mature into lipid loaded adipocytes when cultured in appropriate conditions. Thus, to generate adipocytes, 3T3-L1 fibroblasts were thawed and cultured at 37° C. in normal growth media (DMEM with 4 mM L-glutamine adjusted to contain 1.5 g/L sodium bicarbonate, 4.5 g/L glucose and 1 mM sodium pyruvate+10% v/v FBS). Medium was changed every 2-3 days. When required for experiments, cells were implanted into 12 well plates until they reached 100% confluency (~3 days). Cells were differentiated into pre-adipocytes via incubation in differentiation media for 3 days. The differentiation media consisted of 10% v/v FBS in DMEM with 1 μg/mL streptomycin, 1 μg/mL penicillin, 2 μg/mL insulin, 0.1 μg/mL dexamethasone, 500 μM 3-isobutyl-1-methylxantine (IBMX) and 0.1 mg/mL biotin. After differentiation, pre-adipocytes were incubated with post-differentiation media, which contained only 2 μg/mL insulin in normal growth media, for 3 days to further differentiate them into mature adipocytes with increased lipid droplet formation.

Figure 13:
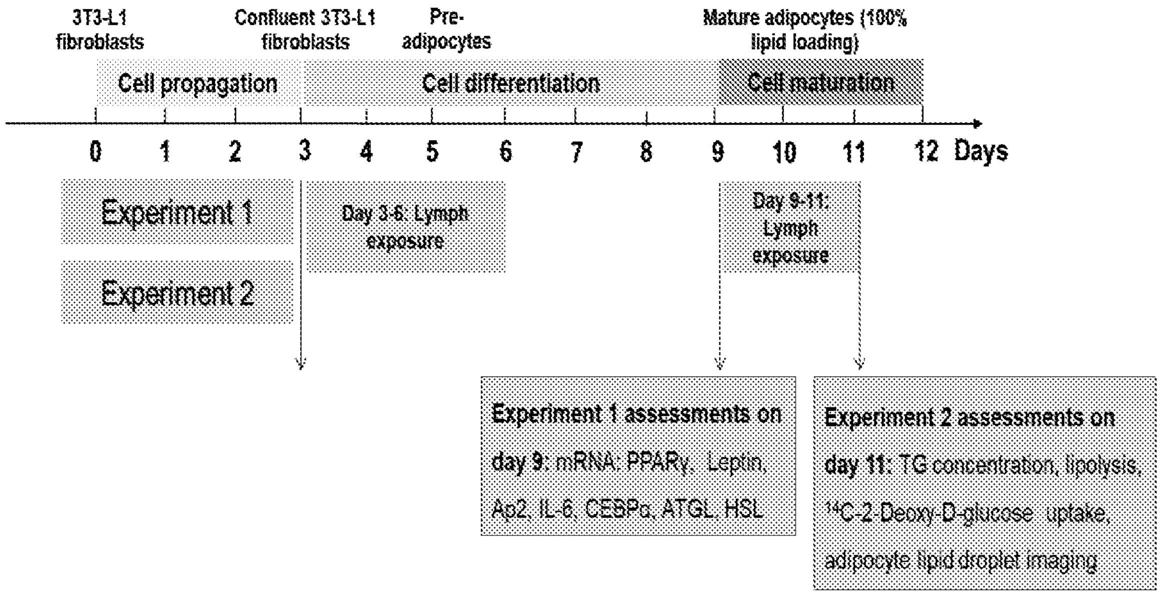
FIG. 13 shows a timeline overview of the experiments described in Example 5.

To probe the effects of mesenteric lymph fluid on adipocyte function, 3T3-L1 cells were exposed to either 2% v/v CFD-lymph in normal growth media, 2% v/v HFD-lymph in normal growth media, or normal growth media (control) for 2 or 3 days when either confluent early fibroblasts (Experiment 1, lymph exposure on day 3-6) or mature adipocytes (Experiment 2, lymph exposure on day 9-11) as shown in FIG. 13. The mesenteric lymph used in the experiments was collected from rats fed a CFD or HFD for 6-9 weeks. As shown in FIG. 13, the following changes in adipocyte function were assessed: (1) mRNA expression of markers of adipocyte differentiation i.e. adipogenesis (peroxisome proliferator-activated receptor γ (PPARγ), CCAAT/enhancer-binding protein α (CEBP/α), glyceraldehyde 3-phosphate dehydrogenase (GAPDH), leptin, adipocyte fatty acid binding protein (AP2)), inflammation (interleukin-6 (IL-6)), lipolysis enzymes (adipose triglyceride lipase (ATGL) and hormone-sensitive lipase (HSL)) and lipid storage (leptin, AP2), as measured by qPCR; (2) adipocyte morphology, including adipocyte and lipid droplet size and number, as imaged via fluorescence microscopy; (3) adipocyte TG lipolysis and ensuing release of glycerol and FFA, (4) lipid storage, with cellular TG content measured using a colorimetric kit; and (5) insulin stimulated uptake of 2-deoxy-glucose (2DG) into adipocytes.

Measurements of Adipocyte mRNA Expression of Markers of Adipogenesis, Lipolysis and Inflammation after Lymph Exposure Confluent 3T3-L1 fibroblasts were treated with lymph from day 3-6 as per the Experiment 1 protocol outlined in FIG. 13. At maturation (day 9), adipocytes were washed with PBS twice, RNA was isolated and qPCR analysis was performed, as described below.

Total RNA was isolated from cultured adipocytes using QIAzol lysis reagent. Briefly, adipocytes from a 12 well plate were homogenised in 500 μL QIAzol lysis reagent. 250 μL chloroform was added to the tube, which was then inverted 10-15 times and centrifuged at 14,000 g for 5 min to achieve phase separation. The top aqueous phase containing RNA was collected for further RNA precipitation. RNA was cleaned with 100 μL of 100% v/v isopropanol followed by centrifugation at 14,000 g for 5 min, then further cleaned with 100 μL 75% v/v ethanol in water followed by centrifugation at 14,000 g for 5 min. Any potential contaminating DNA was digested with DNase I according to the manufacturer's instructions (DNA-free™ DNA removal kit, Invitrogen, Australia).

For adipose tissue RNA extraction, tissue was homogenised and mechanically dissociated in 350 μL RLT buffer containing 1% β-mercaptoethanol. The sample was centrifuged at 14000 rpm for 3 min at room temperature, and 300 μL of the supernatant (lysate) was transferred to a 1.5 mL Eppendorf tube for further process. Equal volume (300 μL) of 70% ethanol was added to the lysate and mixed gently. The mixture was transferred to an RNeasy spin column in 600 μL volumes and centrifuged at 10000 rpm for 15 s to allow the liquid to pass through the column. The column was washed by centrifugation (10000 rpm, 15 s) with 350 μL of buffer RW1. Next, a mixture of 10 μL of DNase stock solution and 70 μL of Buffer RDD (DNase digestion buffer) was added directly to the column membrane and incubated for 15 min. The column was washed by centrifugation with buffer RW1 (10000 rpm, 15 s), and then buffer RPE (1× 10000 rpm for 15 s, 1× 10000 rpm for 2 min). Following each centrifugation wash, the flow-through from the collection tube was discarded. The RNeasy spin column was then placed into a new collection tube and centrifuged at 10000 rpm for 2 min to remove any residual flow-through. The RNeasy column was then placed into an Eppendorf tube and 14 μL of RNase free water was added directly to the membrane of the column, and the column was centrifuged at 10000 rpm for 1 min to elute the RNA. RNA was quantified using the Nanodrop ND1000 spectrophotometer (Thermo Scientific, Waltham, MA, USA), and stored at −80° C. until usage.

First strand cDNA was synthesised from the isolated RNA using an iScript cDNA synthesis kit (Bio-Rad, Australia) according to the manufacturer's instructions. Taqman primers, as listed in Table 2, and TaqMan Universal PCR Master Mix (both from Applied Biosystems, Australia) were used for detection and quantification of the genes of interest. qPCR was performed with 50-100 ng cDNA template incubated for 2 min at 50° C. and 15 min at 95° C., followed by 40 cycles at 95° C. for 15 secs and 60° C. for 1 min with a Bio-Rad Thermocycler 1000 instrument (Bio-Rad Laboratories, Australia). mRNA expression was normalized to the expression of 18s rRNA (housekeeping gene) using the ΔΔCt method.

TABLE 2

Taqman primers used for real time qPCR

| Gene | Assay ID |
|---|---|
| PPARγ | Mm01184322_m1 |
| CEBPα | Mm00514283_s1 |
| CEBPβ | Mm00843434_s1 |
| GAPDH | Mm99999915_g1 |
| IL-6 | Mm00446191_m1 |
| HSL | Mm00495359_m1 |
| ATGL | Mm00503040_m1 |
| Leptin | Mm00434759_m1 |
| FABP4 (Ap2) | Mm00445878_m1 |
| 18s rRNA | Mm03928990_g1 |

Adipocyte Morphology after Lymph Exposure

Mature adipocytes were treated with lymph from day 9-11 as per the Experiment 2 protocol in FIG. 13. At the end of the lymph treatment period (day 11), cells were fixed with 4% v/v paraformaldehyde in a 12 well plate at room temperature for 1 h, and cellular lipids were stained with 2 μg/mL Bodipy fluorescent dye (D3922) in PBS and nuclei were stained with Hoechst (R37606) at 1:200 v/v dilution in PBS for 10 min (both stains from Invitrogen, CA, USA). Adipocyte morphology (i.e. adipocyte and lipid droplet size and number) was then assessed from images taken using a Leica SP8 inverted confocal microscope under a 63× oil-immersion objective with 1.5× magnification controlled by LAS AF image acquisition and processing software (Leica, Wetzlar, Germany). Excitation and emission were set to 405-490 nm for Hoechst and 495-550 nm for Bodipy. Images were taken as a Z-stack with average height of 10-15 μm with a step size of 0.5 μm and line average of 2. An average of one 3×3 tile scan (i.e. total of 9 individual fields) was imaged per well of adipocytes. Captured images were analyzed using Fiji (Image J) software to calculate the average area per adipocyte occupied by a lipid droplet.

Adipocyte Lipolysis

Mature adipocytes were incubated with lymph from day 9-11 as per the Experiment 2 protocol outlined in FIG. 13 and at day 11 were washed twice with warm PBS followed by incubation in Krebs buffer substituted with 8 mM glucose (G8270, Sigma Aldrich, Australia) and 1% w/v BSA (A7030, Sigma Aldrich, Australia). Prior to incubation, buffers were gassed with oxygen for 20 min. Cells were incubated in the Krebs buffer for 2 h to allow FFA and glycerol release into the media, in the presence or absence of 20 μM forskolin to stimulate lipolysis via activation of adenylate cyclase. After incubation, cells were washed twice with cold PBS and lysed in 120 μL RIPA buffer (R0278, Sigma Aldrich, Australia), and the supernatant was collected for analysis of glycerol (free glycerol reagent kit, F6428, Sigma Aldrich, Australia) and protein (Pierce™ BCA protein analysis kit, 23225, ThermoFisher, MA, USA) concentration, each according to the manufacturer's protocol.

Adipocyte Intracellular TG Accumulation

Mature adipocytes were incubated with lymph from day 9-11 as per the Experiment 2 protocol in FIG. 13 and at day 11 were washed twice with cold PBS, and then resuspended in 500 μL PBS. Cells were lysed by passing them five times through a 31 gauge needle attached to an insulin syringe. TG was extracted from the cell lysate through the addition of 200 μL 2:1 chloroform:methanol followed by vortexing for 1 min. The TG extract was centrifuged at 1000 g for 10 min to achieve phase separation. The bottom (organic) layer was transferred into glass vials for evaporation under nitrogen. Samples were resuspended in 100 μL 95% v/v ethanol in water. TG concentration was assayed using a serum TG determination kit (TR0100, Sigma, Missouri, USA) according to the manufacturer's protocol.

Adipocyte Glucose Uptake

Adipocyte 2DG uptake in basal and insulin stimulated conditions was used to determine adipocyte insulin sensitivity. Mature adipocytes were incubated with lymph from day 9-11 as per the Experiment 2 protocol in FIG. 13 and on day 11 were washed twice in warm PBS. Cells were resuspended in 500 μl of oxygenated DMEM buffer supplemented with 8 mM 2DG, 2.5 mM sodium pyruvate and 1% w/v BSA with or without 10 nM insulin, and incubated for 10 min at 37° C. on a shaker (Orbital mixer incubator, Ratek). After incubation, adipocytes were treated with 10 nM insulin for 10 min (stimulated adipocytes) or not (non-stimulated adipocytes) plus 0.1 mmol/L $^{14}$C-2DG (2 mCi/mL) in DMEM buffer for quantification of glucose uptake. After incubation, cells were washed twice in cold PBS and resuspended in 200 μl 0.1% v/v triton X-100 in PBS. 30 μl of cell suspension was used to measure protein concentration (using BCA protein analysis kit, ThermoFisher, Australia) and the remaining material was added to 2 mL of scintillation fluid (ULTIMA Gold uLLT) for scintillation counting of $^{14}$C-2DG in the adipocytes (in disintegrations per min (dpm)). 2DG uptake efficiency was determined from the ratio of $^{14}$C-2DG dpm to the measured protein concentration (mg/mL).

Example 6: Quantification of Insulin-Stimulated Glucose Uptake into Isolated Mesenteric Adipose Tissue Mesenteric adipose tissue (20-40 mg) was isolated from CFD fed mice and from HFD fed mice at the leaky and non-leaky regions of lymphatic vessels, as assessed by Evans blue lymphangiography. Glucose uptake efficiency into the isolated adipose tissue was estimated using the glucose analogue $^{14}$C-2DG, as described previously but with slight modifications (Roy, D., Perreault, M. & Marette, A. Insulin stimulation of glucose uptake in skeletal muscles and adipose tissues in vivo is NO dependent. *Am. J. Physiol.* 274, E692-699 (1998) and Stone, K. P., Wanders, D., Orgeron, M., Cortez, C. C. & Gettys, T. W. Mechanisms of Increased In Vivo Insulin Sensitivity by Dietary Methionine Restriction in Mice. *Diabetes* 63, 3721-3733 (2014).). First, the adipose tissue was carefully dissected and incubated at 37° C. and 5% $CO_2$ for 30 min in a 24 well plate containing 1 ml of oxygenated DMEM buffer supplemented with 8 mM 2DG, 2.5 mM sodium pyruvate and 1% w/v BSA to normalize the metabolic condition of the tissue. After the initial incubation, adipose tissue was treated with 100 nM insulin in Krebs buffer supplemented with 8 mM 2DG, 2.5 mM sodium pyruvate and 1% w/v BSA for 20 min at 37° C. and 5% $CO_2$. Next, tissue was incubated with 0.1 mmol/L $^{14}$C-2DG (2 mCi/mL) in Krebs buffer supplemented as before with 100 nM insulin for 20 min at 37° C. and 5% $CO_2$. After incubation, the tissue was washed in cold PBS 2-3 times and then homogenised in 700 μL PBS. 2 mL of scintillation fluid (ULTIMA Gold uLLT) was added for scintillation counting on a Packard Tri-Carb 2000CA liquid scintillation analyzer (Packard, Meriden, CT). $^{14}$C-2DG uptake was determined from the ratio of disintegrations per min (dpm) to wet weight (g) of tissue.

Example 7: Quantification of Immune Cell Types in Mesenteric Lymph Fluid, Lymph Nodes, and FALCs by Flow Cytometry Mesenteric lymph fluid was collected as described above. 30-40 μL of lymph fluid was pelleted then washed once with 200 μL 2% v/v FBS in PBS before cells were stained for flow cytometry. Lymph nodes from the same animals were also collected and weighed before being passed through a 70 μm cell mesh to obtain a single-cell suspension. Cells from lymph and lymph nodes were suspended in 1 mL 2% v/v FBS in PBS and incubated with antibodies at the concentrations listed in Table 3 in the dark at 4° C. for 20 minutes. For T helper (Th) cell analysis, an aliquot of the single cell suspension from lymph and lymph nodes was stimulated with 50 ng/mL PMA and 1 μg/mL ionomycin in 0.5% v/v FBS in RPMI 1640 medium for 3.5 h in the presence of 6.6 μL of 1:100 diluted Golgi Stop (BD Biosciences, Franklin Lakes, NJ, USA). After stimulation, cells were fixed and permeabilised using the Cytofix/Cytoperm kit according to the manufacturer's protocol (554715, BD Biosciences, Franklin Lakes, NJ, USA). Cells were then stained for intracellular cytokines (Table 3) for 20 min in the dark at 4° C. Cells were analyzed using a BD FACS Canto II (BD Biosciences, Franklin Lakes, NJ, USA) and FlowJo software version 10 (Tree Star Inc., Ashland, OR, USA). All appropriate controls, including negative controls, compensation controls and fluorescence minus one (FMO) controls, were applied.

TABLE 3

Antibodies used for flow cytometry analysis of cells from mesenteric lymph fluid and lymph nodes

| Antigen | Fluorochrome | Host/Isotype | Clone | Supplier | Dilution |
|---|---|---|---|---|---|
| B220 | FITC | Rat IgG2a, kappa | RA3-6B2 | eBioscience[1] | 1:500 |
| CD11c | PE-Cyanine 7 | Armenian hamster IgG | N418 | eBioscience[1] | 1:500 |
| CD19 | APC | Rat IgG2a, kappa | 6D5 | Biolegend[2] | 1:500 |
| CD3 | eFluor 450 | Rat IgG2b, kappa | 17A2 | eBioscience[1] | 1:500 |
| CD4 | eFluor 780 | Rat IgG2a, kappa | RM4-5 | eBioscience[1] | 1:500 |
| CD4 | FITC | | | | 1:500 |
| CD44 | PE-Cyanine 5 | Rat IgG2b | 1M7 | eBioscience[1] | 1:500 |
| CD45 | FITC | Rat IgG2b, kappa | 30-F11 | Biolegend[2] | 1:500 |
| CD62L | PE | Rat IgG2a, kappa | MEL-14 | eBioscience[1] | 1:500 |
| CD8a | APC | Rat IgG2a, kappa | 53-6.7 | Biolegend[2] | 1:500 |
| CD8a | V500 | Rat IgG2a, kappa | 53-6.7 | BD Biosciences[3] | 1:200 |
| F4/80 | PE | Rat IgG2a, kappa | BM8 | Biolegend[2] | 1:500 |
| fixable viability dye | eFluor 506/780 | — | — | eBioscience[1] | 1:1000 |
| Ly6G | PE-Cyanine 7 | Rat IgG2a, kappa | 1A8 | Biolegend[2] | 1:500 |
| LYVE1 | eFluor 660 | Rat IgG1, kappa | ALY7 | eBioscience[1] | |
| NK1.1 | APC-Cyanine 7 | Mouse IgG2a, kappa | PK136 | Biolegend[2] | 1:500 |
| IL-4 | APC | Rat IgG2b, kappa | 11b11 | BD Biosciences[3] | 1:200 |
| IL-17A | PE | Rat IgG2a, kappa | TC11-18H10.1 | BD Biosciences[3] | 1:200 |
| IFNγ | PE-Cyanine 5 | Rat IgG2a, kappa | XMG1.2 | BD Biosciences[3] | 1:200 |
| IgM | eFluor 450 | Rat IgG2a, kappa | RMM-1 | Biolegend[2] | 1:500 |
| IgD | PerCp | Rat IgG2a, kappa | 11-26c.2a | Biolegend[2] | 1:500 |

[1]eBiosciences, San Diego, CA, USA
[2]BioLegend, San Diego, CA, USA
[3]BD Biosciences, NSW, Australia FALCs were cleaned of adipose tissue with fine forceps and used whole. FALCs were passed through a 70 μm cell mesh (In Vitro Technologies, Australia) to obtain a single cell suspension in 2% FBS in PBS. Cells from FALCs were incubated with antibodies at the dilutions listed in Table 4 at 4° C. in darkness for 20 minutes. After antibody incubation, cells were washed once with 200 μL 2% v/v FBS in PBS and centrifuged for 5 min at 300 g. Final cell pellets were resuspended in 200 μL 2% v/v FBS in PBS. Cells were analysed using a BD Canto II (BD Biosciences, Franklin Lakes, NJ, USA) and FlowJo software (Tree Star Inc., Ashland, OR, USA). Countbright counting beads (Invitrogen, Carlsbad, CA, USA) were added to the samples to define the absolute number of cells in the samples. All appropriate controls including negative controls, compensation controls and fluorescence minus one (FMO) controls were applied.

TABLE 4

| Antibodies used for flow cytometry analysis of cells from FALCS | | | | | |
|---|---|---|---|---|---|
| Antigen | Fluorochrome | Host/Isotype | Clone | Supplier | Dilution |
| MHCII | FITC | Rat IgG2a, kappa | M5/114.15.2 | Biolegend[2] | 1:500 |
| CD11c | PE-Cyanine 7 | Rat IgG2a, kappa | N418 | Biolegend[2] | 1:500 |
| LYVE-1 | APC | Rat IgG2a, kappa | ALY7 | eBiosciences[1] | 1:500 |
| CD3 | eFluor 450 | Rat IgG2b, kappa | 17A2 | Biolegend[2] | 1:500 |
| CD25 | eFluor 780 | Rat IgG2a, kappa | 3C7 | Biolegend[2] | 1:500 |
| Viability | eFluor 506 | — | — | eBiosciences[1] | 1:1000 |
| CD11b | PE-Cyanine 5 | Rat IgG2b | MI/70 | Biolegend[2] | 1:500 |

[1]eBiosciences, San Diego, CA, USA
[2]BioLegend, San Diego, CA, USA

Example 8: Enzyme-Linked Immunosorbent Assays (ELISAs) of Lymph and Plasma Samples Plasma and lymph were preserved at −20° C. until ELISAs were conducted. VEGFc and PGE2 concentrations were measured in lymph and plasma using ELISA kits (VEGFc, CSB-E07361m, CusaBio Life science, MD, USA and PGE2, ab133021, Abcam, Cambridge, UK). The dilution factors for PGE2 in lymph and plasma were 1:200 and 1:10, respectively. The dilution factor for VEGFc in lymph was 1:20 (HFD) or 1:5 (CFD). Insulin was measured in plasma using an ELISA kit (Crystal Chem, IL, USA). The dilution factor for insulin in plasma was 1:5. ELISA were performed according to the manufacturers' instructions without any modifications.

Example 9: Lymph and Blood Compositional Analysis, Including Lipidomics

Commercial kits for the analysis of TG (TR0100, Sigma, Missouri, USA), total cholesterol (A12216, Invitrogen, Australia) and FFA (HR Series NEFA-HR (2), 434-91795) and phospholipid (Phospholipid C kit, 997-01801) (both from Wako Pure Chemical Industries, Osaka, Japan) were used to quantify lipids in mesenteric lymph and plasma according to the manufacturers' instructions.

For lipidomics analysis, lipid was extracted from 50 μl mesenteric lymph via addition of 200 μl chloroform:methanol (1:3). Samples were vortexed for 1 h at 4° C. and then centrifuged at 16,000 g for 10 min. Supernatant was carefully transferred to another tube and stored at −80° C. until analysis. Before LCMS analysis, the extract was dried with nitrogen and reconstituted in 20 μl water and 180 μl butanol-methanol (1:1 v/v). The reconstituted extract was vortexed (Vortex mixer, Ratek) for 200 seconds with 20 cycles of 5 sec spin and 20 sec vortex. The extract was sonicated in a water bath for 1 hour which was maintained at <20° C. by sonicating the samples on ice. The samples were then centrifuged for 10 min at 16,000 g and the supernatant was transferred to LCMS vials and stored at 4° C. prior to analysis.

Lipidomics analysis was performed using reversed phase liquid chromatography and high-resolution mass spectrometry. Samples (10 μl) were injected onto a Dionex Ultimate 3000 UHPLC system (Thermo Scientific, Australia) fitted with an analytical C8 column (100×2.1 mm; 2.7 μm, Sigma Aldrich, Australia). Chromatography was performed using solvent A (2 mM formic acid, 8 mM ammonium formate, 40% v/v isopropanol) and solvent B (2 mM formic acid, 8 mM ammonium formate, 98% v/v isopropanol) as mobile phases with a 30 min gradient starting at 0% B and increasing to 35% B from 0 to 8 min, then to 50% B from 8-16 min, then to 80% B from 16-19 min, then finally to 100% B by 23 min. 100% B was maintained for a further 3 min before equilibrating to 0% by 28 min and washing for a further 2 min.

Mass spectrometry was conducted with a Q-Exactive MS (Thermo Scientific, Australia) with a heated electrospray source which operated in both positive and negative modes with rapid switching, and with a mass resolution of 140,000 from m/z 140 to 2000. The instrument was maintained and calibrated with a mass accuracy of <2 ppm. Samples were analysed in random order, and solvent blank and pooled quality control samples were analyzed at regular intervals throughout the batch.

The mass spectrometry data were then analyzed using IDEOM software. Briefly, raw files were converted to mzXML with msconvert, LC-MS peak signals were extracted with the Centwave algorithm in XCMS, samples were aligned and artefacts were filtered with mzMatch and additional data filtering and feature identification based on accurate mass was performed with IDEOM. Lipid identifications based on accurate mass are deemed level 3 identifications according to the Metabolomics Standards Initiative. Manual inspection of data resulted in exclusion of one outlier sample from each sample group, and additional manual data filtering was performed to remove lipid features that were not reliably detected across replicates. LC-MS peak height was used as the determinant for lipid abundance and data was normalised to median peak intensity. Univariate statistical analyses in IDEOM were performed using Welch's T-test ($\alpha$=0.05) and Pearson's correlation (MS Excel). Multivariate statistical analysis was performed using Metaboanalyst (Chong, J., et al. MetaboAnalyst 4.0: towards more transparent and integrative metabolomics analysis. *Nucleic Acids Res* (2018).).

Example 10: Lymphatic Endothelial Cell Preparation and Migration Assay

LECs from adult human skin (HMLEC-dLyAd) were obtained from Lonza (Australia) at the 3rd passage. Cells were thawed and expanded in a T-75 flask at a minimum density of 500,000 cells per flask. Cells were grown in EGM-2MV BulletKit™ medium (CC-3162, Lonza, Australia), which consisted of EBM-2 basal medium supplemented with an EGM-2 SingleQuots™ kit (Lonza, Australia). Flasks were incubated at 37° C. and 5% $CO_2$, and media was changed 24 h after seeding and then every 48 h. Cells were grown to 70-80% confluence and split every 4-5 days. For all experiments, cells were seeded onto plates or coverslips pre-coated with rat tail collagen Type I (50 μg/ml) for 1 h at 37° C. Cells were allowed to grow to 100% confluence (which typically occurred 1.5-2 days after seeding in a cell culture plate) prior to the start of experiments.

Once the LECs reached confluence, the impact of lymph fluid on LEC migration was assessed using a standard scratch assay. To achieve this, primary LECs were seeded in a 24 well plate and grown to confluence in EGM-2MV BulletKit™ media (standard LEC growth media) to form a uniform monolayer. The LECs were then starved in EBM media supplemented with only 0.5% w/v FBS for 6 hours to overnight. Cell scratching was performed using a 200 μL pipette tip, and cells were then incubated for up to 30 hours in 0.5% FBS w/v in EBM media with or without 2% lymph from CFD-fed and HFD-fed mice. The VEGFR3 kinase inhibitor MAZ51 (5 μM) or the COX-2 inhibitor celecoxib (20 μM) were also added to LECs that were treated with HFD-lymph. Images of LEC migration were captured hourly using an Operetta high-content imaging system (PerkinElmer) with a 10× Plan Apo NA0.3 objective.

Images taken at several time points after wounding (0, 12 and 24 hours) were analyzed using the Fiji distribution of ImageJ to determine the rate of LEC migration over the area of the scratched wound. To enable quantification of the area of the scratch wound, the brightness and contrast of the images was first adjusted to improve the visibility. An outline of the wound was manually drawn and the area of the wound was quantified at each time point. LEC migration was quantified using the standard equation: % Scratched Area Recovered=100%−% remaining scratch area (i.e. area without cells) at each time point, and the results were plotted over time to generate a migration rate profile.

Example 11: Mesenteric Lymphatic Uptake and Systemic Exposure of Celecoxib and Prodrug Compound I-1

Formulation Preparation

To evaluate the lymphatic uptake of celecoxib and the celecoxib prodrug, lipid based formulations of celecoxib or celecoxib prodrug were prepared as described previously (Han, S., et al. Targeted delivery of a model immunomodulator to the lymphatic system: Comparison of alkyl ester versus triglyceride mimetic lipid prodrug strategies. *J Control Release.* 177, 1-10 (2014).). Briefly, 6.67 mg/kg of celecoxib or celecoxib prodrug Compound I-1, 133 mg/kg oleic acid, and 73.3 mg/kg Tween 80 were mixed in a glass vial and incubated at 37° C. overnight to equilibrate. An aqueous phase consisting of 0.5 mL PBS (pH 7.4) was subsequently added to the lipid phase and the formulation was emulsified by ultrasonication with a Misonix XL 2020 ultrasonic processor (Misonix, Farmingdale, NY, USA) equipped with a 3.2 mm microprobe tip running at an amplitude of 240 μM and frequency of 20 kHz for 2 min at room temperature.

To evaluate the systemic exposure of celecoxib and celecoxib prodrug Compound I-1, 29 mg/kg celecoxib or celecoxib prodrug (equivalent to 8.3 mg/kg celecoxib) were administered in a self-emulsifying lipid-based formulation consisting of oleic acid (Sigma Aldrich, Australia)/Cremophor RH40 (Sigma Aldrich, Australia)/ethanol (40:52.6:7.4, w/w/w). Drug and prodrug concentrations in the formulations were confirmed using HPLC-MS/MS as described below.

In Vivo Lymph and Plasma Pharmacokinetic Study Design

To evaluate lymphatic uptake of celecoxib and celecoxib prodrug Compound I-1 in mice, the mesenteric lymph duct was cannulated as described above and the duodenum was cannulated for drug administration and rehydration. Mice remained anaesthetised with isoflurane delivered via a nose cone throughout the surgery and experiment as lymph collection was too difficult in conscious animals. Celecoxib and celecoxib prodrug lipid base formulations were administered via intra-duodenal infusion over 1 h at a rate of 0.5 mL/h followed by rehydration with normal saline at a rate of 0.3 mL/h. Lymph was collected every hour for up to 6 h post-dosing and transferred to pre-weighed tubes containing 5 μL of 1000 IU/mL heparin. Aliquots (20 μL) of hourly lymph samples were stored at −20° C. prior to assay of drug and/or prodrug concentrations via HPLC-MS/MS, as below.

In addition to evaluating lymph uptake of celecoxib and celecoxib prodrug, a pharmacokinetic dose-determining study was conducted to determine a dose of celecoxib and celecoxib prodrug that produce higher lymphatic uptake but lower systemic plasma celecoxib exposure (i.e. lower plasma concentrations over time) after administration of the prodrug. For these dose-determining studies, 29 mg/kg celecoxib or celecoxib prodrug (equivalent to 8.3 mg/kg celecoxib) in the lipid-based formulation (as described above) were administered via oral gavage. Blood samples (100 μL) were then collected via a cheek bleed at time points 0, 0.5, 1, 1.5, 2, 3 or 5 h from different mice after celecoxib or prodrug administration. Plasma was separated from the blood via centrifugation at 2,000 g for 5 min and then stored at −20° C. prior to assay of drug and/or prodrug concentrations via HPLC-MS/MS.

Preparation of Lymph and Plasma Samples for HPLC-MS/MS Analysis

For HPLC-MS/MS analysis of celecoxib in lymph, 250 μL acetonitrile was added to 20 μL lymph samples and 5 μL of a 1 μg/mL solution of internal standard (5,5-diethyl-1,3-diphenyl-2-iminobarbituric acid) in acetonitrile. Samples were vortexed for 30 seconds and centrifuged at 4,500 g for 5 min, and 80 μL supernatant was then transferred to a HPLC vial for analysis.

For HPLC-MS/MS analysis of celecoxib prodrug Compound I-1 in lymph, 5 μL of a 1 μg/mL solution of internal standard (5,5-diethyl-1,3-diphenyl-2-iminobarbituric acid) in acetonitrile was added to 20 μL lymph samples. To quantify total celecoxib derivatives in lymph after administration of the glyceride prodrug an in vitro hydrolysis method was developed to liberate the celecoxib from the glyceride backbone of the prodrug for quantitation. (This was conducted because the glyceride-based prodrug of celecoxib may undergo hydrolysis in the gastrointestinal tract followed by resynthesis with fatty acids in the enterocyte to generate a variety of glyceride derivatives of celecoxib in lymph, with different fatty acids attached, that could not be quantified individually due to lack of reference standards.) For the in vitro hydrolysis method, 140 μL of 0.5 M NaOH in 1:1 v/v ethanol:water was added to 20 μL lymph and heated at 60° C. for 20 min. Subsequently, 70 μL of 1M HCL in water was added to each sample to terminate hydrolysis. After vortexing for 0.5 min, a 150 μL aliquot of the sample was diluted with 200 μL of 80% v/v acetonitrile in 0.1% v/v formic acid in Milli-Q water. Samples were vortexed for a further 0.5 min followed by centrifugation at 4,500 g for 5 min, and 80 μL supernatant was assayed by HPLC-MS for detection of celecoxib liberated from the prodrug.

For HPLC-MS/MS analysis of celecoxib in plasma after dosing celecoxib or celecoxib prodrug Compound I-1, 200 μL acetonitrile was added to 20 μL samples of plasma and 5 μL of a 1 μg/mL solution of internal standard (5,5-diethyl-1,3-diphenyl-2-iminobarbituric acid) in acetonitrile. Samples were vortexed for 30 seconds and centrifuged at 4,500 g for 5 min, and 80 μL supernatant was analyzed for celecoxib concentration by HPLC-MS. Celecoxib might only be active in plasma and systemically after liberation from the prodrug, hence only the plasma concentration of celecoxib (and not glyceride-esterified celecoxib) was determined after the administration of celecoxib and celecoxib prodrug.

HPLC-MS/MS Analysis of Celecoxib and Celecoxib Prodrug Compound I-1

HPLC-MS/MS analysis of celecoxib and celecoxib prodrug was performed using a Shimadzu LC-MS 8050 system (Shimadzu Scientific Instruments, Kyoto, Japan), which consisted of a CBM-20A system controller, a DGU-20A5R solvent degasser, two LC-30AD pumps, a SIL-30AC autosampler, a CTO-20AC column oven (held at 40° C.), and a triple quadrupole mass spectrometer with an electrospray ionization interface (ESI). The desolvation line (DL) and the heat block were maintained at 250° C. and 400° C., respectively. Interface and detector voltages were 4.0 kV and 2.3 kV, respectively. The nebulizing gas flow rate and drying gas flow rate were 3 L/min and 10 L/min, respectively. 10 μL samples were injected onto a Ascentis C18 column (2.7 μm particle size, 50 mm×2.10 mm, Supelco, United States) and the mobile phase flow rate was 0.3 mL/min. Mobile phase A (MPA) was 100% v/v milli Q water with 0.1% formic acid and mobile phase B (MPB) was 100% v/v methanol with 0.1% formic acid. The mobile phase gradient sequence v/v was initiated with 50% MPB, then linearly increased to 90% MPB over 1.2 min and held for 0.5 min, then returned to 50% MPB over 0.8 min and held for 1.5 min leading to a total 4 min run time. Ion transitions for celecoxib and internal standard were 382.10-361.90 m/z and 336.2-195.0 m/z. Celecoxib and internal standard (5,5-diethyl-1,3-diphenyl-2-iminobarbituric acid) eluted at 1.8 min and 1.6 min, respectively.

The HPLC-MS/MS assay for celecoxib and internal standard in lymph and plasma samples was validated via an assay of replicate (n=3-5) quality control samples at low, medium and high concentrations. The assays were accurate (within 10-15% of target concentration) and precise (coefficient of variation<10%) for celecoxib concentrations ranging from 0.25 to 20 μg/mL in plasma, and 0.25 to 20 μg/mL (after celecoxib administration) or 2.5 to 80 μg/mL (total celecoxib derivatives after celecoxib prodrug administration) in lymph samples.

We claim:

1. A method of treating or preventing obesity, insulin resistance, hyperinsulinemia, or type 2 diabetes in a patient in need thereof, comprising administering to the patient an effective amount of a lipid prodrug of Formula I:

I

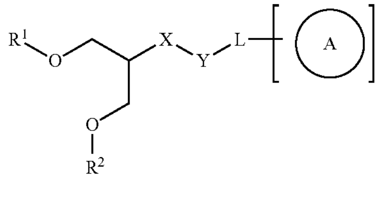

or a pharmaceutically acceptable salt thereof, wherein:

$R^1$ and $R^2$ are each independently hydrogen, an acid-labile group, a lipid, or —C(O)$R^3$;

each $R^3$ is independently a saturated or unsaturated, straight or branched, optionally substituted $C_{1-37}$ hydrocarbon chain;

X is —O—, —NR—, —S—, —O($C_{1-6}$ aliphatic)-O—, —O($C_{1-6}$ aliphatic)-S—, —O($C_{1-6}$ aliphatic)-NR—, —S($C_{1-6}$ aliphatic)-O—, —S($C_{1-6}$ aliphatic)-S—, —S($C_{1-6}$ aliphatic)-NR—, —NR($C_{1-6}$ aliphatic)-O—, —NR($C_{1-6}$ aliphatic)-S—, or —NR($C_{1-6}$ aliphatic)-NR—, wherein 0-2 methylene units of the $C_{1-6}$ aliphatic group are independently and optionally replaced with —O—, —NR—, or —S— and the $C_{1-6}$ aliphatic group is independently and optionally substituted with 1, 2, or 3 deuterium or halogen atoms;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

Y is absent or is —C(O)—, —C(NR)—, or —C(S)—;

L is a covalent bond or a bivalent, saturated or unsaturated, straight or branched, optionally substituted bivalent $C_{3-30}$ hydrocarbon chain, wherein 0-8 methylene units of L are independently replaced by -Cy-, —O—, —NR—, —S—, —OC(O)—, —C(O)O—, —C(O)—, —S(O)—, —S(O)$_2$—, —C(S)—, —NRS(O)$_2$—, —S(O)$_2$NR—, —NRC(O)—, —C(O)NR—, —OC(O)NR—, —NRC(O)O—, or an amino acid; and wherein 1 methylene unit of L is optionally replaced with -M-; or L is

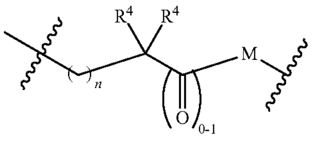

,

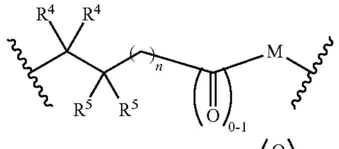

, or

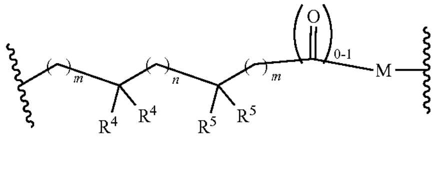

, wherein either the right-hand side or left-hand side of L is attached to A;

wherein M is selected from the group consisting of:

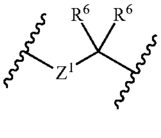

,

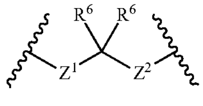

,

-continued

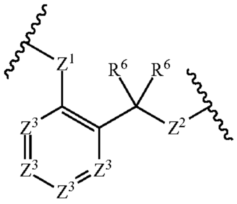,

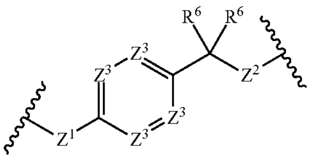,

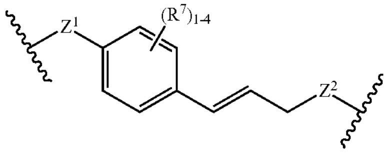,

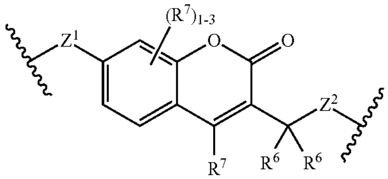,

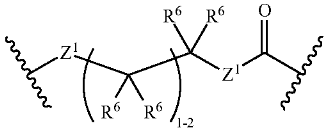,

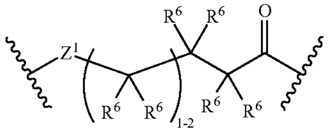,

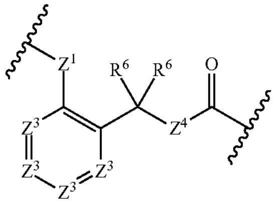, and

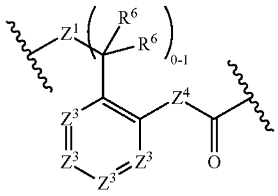, wherein each $R^6$ is independently selected from hydrogen, deuterium, $C_{1-10}$ aliphatic, halogen, or —CN;

each $R^7$ is independently selected from hydrogen, deuterium, halogen, —CN, —OR, —$NR_2$, —$NO_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a $C_{1-6}$ aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the $C_{1-6}$ aliphatic is optionally substituted with 1, 2, 3, 4, 5, or 6 deuterium or halogen atoms;

each $Z^1$ is independently selected from —O—, —NR—, or —S—;

each $Z^2$ is independently selected from —O—, —NR—, —S—, —OC(O)—, —NRC(O)O—, or —OC(O)NR—;

each $Z^3$ is independently selected from =N— or =C($R^7$)—; and each $Z^4$ is independently selected from —O—, —NR—, —S—, —C($R^6$)$_2$—, or a covalent bond;

each -Cy- is independently an optionally substituted 3-6 membered bivalent saturated, partially unsaturated, or aromatic ring having 0-4 heteroatoms independently selected from nitrogen, oxygen, or sulfur;

each $R^4$ and $R^5$ is independently hydrogen, deuterium, halogen, —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or a C1-6 aliphatic group optionally substituted with —CN, —OR, —$NR_2$, —SR, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur, or the C1-6 aliphatic is optionally substituted with 1, 2, 3, 4, 5, or 6 deuterium or halogen atoms; or two instances of $R^4$ or $R^5$ attached to the same carbon atom, taken together with the carbon atom to which they are attached, form a 3-6 membered saturated monocyclic carbocyclic ring or 3-6 membered saturated heterocyclic ring having 1-2 heteroatoms independently selected from nitrogen, oxygen, or sulfur;

n is 0-18;

each m is independently 0-6; and

A is a COX-2 inhibitor.

2. The method of claim 1, wherein $R^1$ and $R^2$ are —C(O)$R^3$.

3. The method of claim 2, wherein each $R^3$ is independently a saturated or unsaturated, unbranched C2-37 hydrocarbon chain.

4. The method of claim 1, wherein X is —O—.

5. The method of claim 1, wherein Y is —C(O)—.

6. The method of claim 1, wherein the lipid prodrug is of Formula IX-c:

IX-c

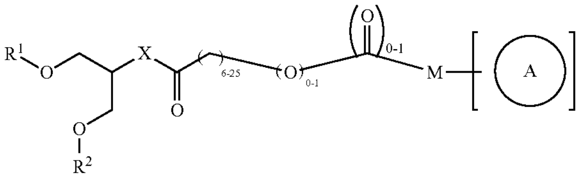

or a pharmaceutically acceptable salt thereof;

wherein M is selected from the group consisting of:

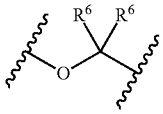,

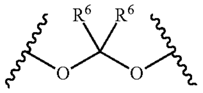,

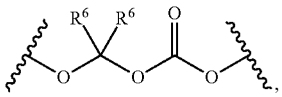,

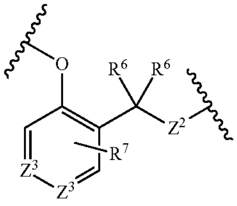,

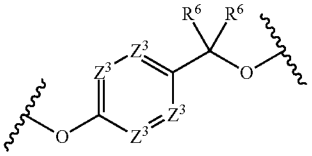,

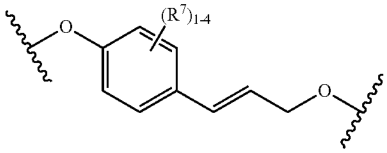,

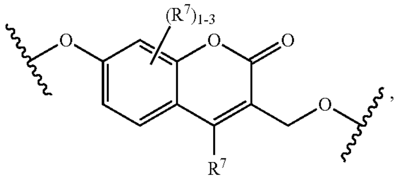,

-continued

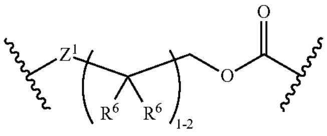,

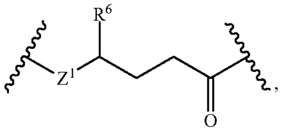,

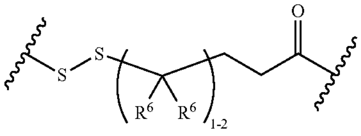,

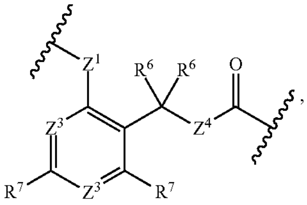, and

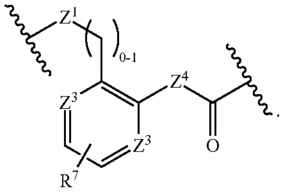.

7. The method of claim 1, wherein the lipid prodrug is delivered selectively to the lymphatic system of the patient.

8. The method of claim 1, wherein the lipid prodrug is administered orally.

9. The method of claim 1, wherein the method further comprises a reduction in mesenteric lymphatic dysfunction, visceral obesity, inflammation, glucose intolerance, and/or insulin resistance associated with obesity.

10. The method of claim 1, wherein the method further comprises reducing an aspect of obesity-associated mesenteric lymphatic dysfunction in the patient.

* * * * *